US005965796A

United States Patent [19]
Meagher et al.

[11] Patent Number: 5,965,796
[45] Date of Patent: Oct. 12, 1999

[54] METAL RESISTANCE SEQUENCES AND TRANSGENIC PLANTS

[75] Inventors: Richard Brian Meagher; Anne O. Summers; Clayton L. Rugh, all of Athens, Ga.

[73] Assignee: University of Georgia Research Foundation Inc., Athens, Ga.

[21] Appl. No.: 08/878,957

[22] Filed: Jun. 19, 1997

Related U.S. Application Data

[63] Continuation-in-part of application No. 08/427,097, Apr. 21, 1995, Pat. No. 5,668,294.

[51] Int. Cl.$^6$ .......................... C12N 15/29; C12N 15/82; A01H 4/00; A01H 5/00
[52] U.S. Cl. .......................... 800/298; 800/278; 800/295; 800/288; 435/69.1; 435/468; 435/419; 435/320.1; 536/23.2; 536/24.1; 536/23.7
[58] Field of Search .............................. 800/265, DIG. 9, 800/DIG. 52, 278, 295, 298; 435/69.1, 172.3, 320.1, 419, 468; 536/23.2, 24.1, 23.7

[56] References Cited

U.S. PATENT DOCUMENTS

| | | | |
|---|---|---|---|
| 4,849,355 | 7/1989 | Wong | 435/172.3 |
| 5,364,451 | 11/1994 | Raskin et al. . | |
| 5,380,381 | 1/1995 | Adang et al. | 536/23.71 |
| 5,668,294 | 9/1997 | Meagher et al. . | |

OTHER PUBLICATIONS

Thompson. PhD. Dissertation, University of Georgia, 1990.
Murray et al. Nucleic Acids Research vol. 17 No. 2, 1989.
Summers et al. Ann. Rev. Microbiol. 40: 607–634, 1986.
Stack, N.M. (1992) The Reconstruction of the Bacterial Gene merA,, BS Thesis, University of Georgia.
Meagher, R.B. (1994) "Phyto–remediadtion of heavy metal ion toxicity: A highly modified bacterial MerA gene confers mercuric ion resistance to transgenic Arabidopsis plants," Abstract of presentation to Dept. of Energy Phyto–remediation Research Workshop, Santa Rosa, California, Jul. 25–26, 1994.
Wilde et al. (1994) In vitro Cellular & Developmental Biology Animal 30A (3 part 2), p. 60.
Rugh et al. (1994) "Ionic Mercury Detoxification by Transgenic Plants," poster abstract presented at American Society of Plant Physiology Annual Meeting, Portland, Oregon, Jul. 30–Aug. 3, 1994.
Thompson, D.M. (1990) *Transcriptional and Post–transcriptional Regulation of the Genes Encoding the Small Subunit of Rubulose–1, 5–Bisphosphate Carboxylase*, Ph.D. Thesis, University of Georgia, Athens, Georgia.
Grill et al. (1987) *Proc. Natl. Acad. Sci. USA* 84:439–443.
Lefebvre et al. (1987) *Biotechnology* 5:1053–1056.
Gilbert and Summers (1988) *Plasmid* 20:127–136.
Begley et al. (1986) *Biochemistry* 25:7186–7192.
Begley et al. (1986) *Biochemistry* 25:7192–7200.
Summers, A.O. (1986) *Ann. Rev. Microbiology* 40:607–634.
Summers and Sugarman (1974) *Journal of Bacteriology* 119:242–249.
Rinderle et al. (1983) *Biochemistry* 22:869–876.
Barrineau et al. (1984) *Journal of Molecular and Applied Genetics* 2:601–619.
McClelland and Ivarie (1982) *Nucleic Acids Research* 10:7865–7877.
Murray et al. (1989) *Nucleic Acids Research* 17:477–494.
Brown et al. (1983) *Biochemistry* 22: 4089–4095.
Misra et al. (1985) *Gene* 34:253–262.
Stormo et al. (1982) *Nucleic Acids Res.* 10:2971–2996.
Heidecker and Messing (1986) *Ann. Rev. Plant Physiol.* 37:439–466.
Foster, T.J. (1983) *Microbiol. Rev.* 47:361–409.
Rensing et al. (1992) *Journal of Bacteriology* 174:1288–1292.
Scheller et al. (1987) *Plant Physiology* 85:1031–1035.
Barkay et al. (1992) *Biodegradation* 3:147–159.
Brunker et al. (1966) *Mol. Gen. Genet.* 251:307–315.
Clark et al. (1977) *J. of Bacteriology* 132(1):186–196.
Dacey, J.W. (1980) *Science* 210:1017–1019.
Dacey, J.W. (1981) *Ecology* 62:1137.
Gilbert, et al. (1988) *Plasmid* 20:127–136.
Ogawa et al. (1984) *Gene* 32:311–320.
Robinson & Tuovinen (1984) *Microbiol Reviews* 48:95–124.
Rugh et al. (1996) *Proc. Natl. Acad. Sci. USA* 93:3182–3187.

*Primary Examiner*—Lynette F. Smith
*Assistant Examiner*—Thomas Haas
*Attorney, Agent, or Firm*—Greenlee Winner and Sullivan PC

[57] ABSTRACT

The present invention provides nucleic acid sequences encoding a metal ion resistance protein, which are expressible in plant cells. The metal resistance protein provides for the enzymatic reduction of metal ions including but not limited to divalent Cu, divalent mercury, trivalent gold, divalent cadmium, lead ions and monovalent silver ions. Transgenic plants which express these coding sequences exhibit increased resistance to metal ions in the environment as compared with plants which have not been so genetically modified. Transgenic plants with improved resistance to organometals including alkylmercury compounds, among others, are provided by the further inclusion of plant-expressible organometal lyase coding sequences, as specifically exemplified by the plant-expressible merB coding sequence. Furthermore, these transgenic plants which have been genetically modified to express the metal resistance coding sequences of the present invention can participate in the bioremediation of metal contamination via the enzymatic reduction of metal ions. Transgenic plants resistant to organometals can further mediate remediation of organic metal compounds, for example, alkylmetal compounds including but not limited to methyl mercury, methyl lead compounds, methyl cadmium and methyl arsenic compounds, in the environment by causing the freeing of mercuric or other metal ions and the reduction of the ionic mercury or other metal ions to the less toxic elemental mercury or other metals.

30 Claims, 8 Drawing Sheets

```
5'S
        10           20           30           40           50         59
CTAGAACTAG TGGATCCCTA GATCTAAGAA GGAACCACA ATG AGC ACT CTC AAA ATC AC-3'
           BamHI      BglII    S.D.        MET           merA
                      STOP     P.T.

3'N
         10           20         30     36
TATCGAATTC CTGCAGCCTC ACCCGGCGCA GCAGGA 3'
   EcoRI   PstI         MerA homology
```

282-312A & 307-339S

```
              285                   290                   295                   300
    Leu Glu Leu Ala Gln Ala Phe Ala Arg Leu Gly Ala Lys Val Thr Ile Leu Ala Arg
5'-ctt gaa ctt gcc cag gcc ttt gca cgt ctt ggt gct aaa gtg acc att ctt gca cgc
5'-             G   C   C   A   C   A   G   G           G   C   G   T
3'-GAA CTT GAA CGG GTC CGG AAA CGT GCA GAA CCA CGA TTT CAC TGG TAA GAA CGT GCG
   merA homology
              305                   310                   315                   320
Ser Thr Leu Phe Phe Arg Glu Asp Pro Ala Ile Gly Glu Ala Val Thr Ala Ala Phe Arg
tcc act ctc ttc ttt cgt GAA GAC CCA GCT ATA GGT GAA GCT GTT ACT GCT GCA TTT CGC
AG  G   G       C   C       overlap region       C           C   G           C
AGG TGA GAG AAG AAA GCA CTT CTG GGT CGA TAT CC-5'

325                   330                   335            339
Met Glu Gly Ile Glu Val Arg Glu His Thr Gln Ala Ser Gln Val Ala Tyr Ile Asn
ATG GAA GGC ATT GAA GTG CGT GAG CAT ACT CAA GCA AGC CAA GTT GCC TAT ATC AAT-3'
        G       C   G       A G   A   C   C   G   C           G   C   G       -3'
                                                                    merA homology
```

FIG. 1C

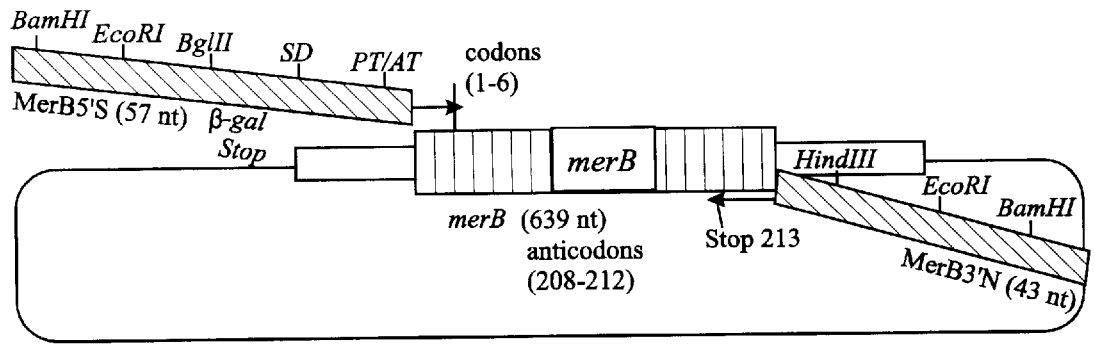

pCT12 contains a 1.5 kb *EcoRI* fragment from a *S. typhimurium* broad spectrum mercury resistance plasmid.

1. PCR amplify 639 bp merB coding sequence with MerB5'S and MerB3'N primers.
2. *BamHI-HindIII* cloning into pBS-SK.

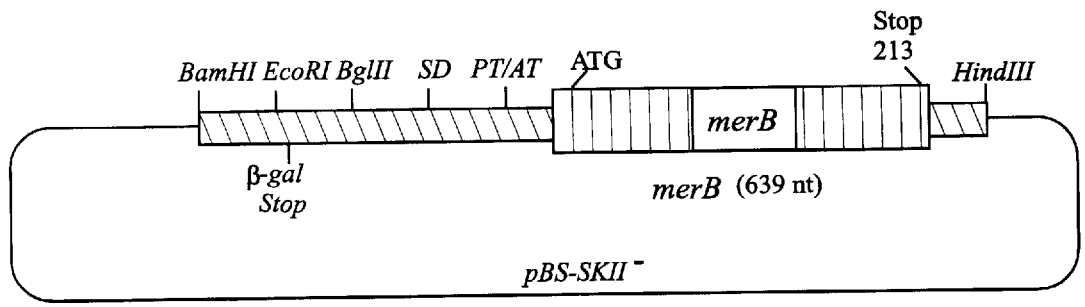

A clone showing activity toward PMA is subcloned into a plant expression vector.

Plant expression: *BamHI/PstI* (pBS-SK site) cloning between 35Sp and NOS3' in binary vector.

Animal Expression: *BamHI-HindIII* cloning into pBC-CMV for fish experiments.

FIG. 4

METAL RESISTANCE SEQUENCES AND TRANSGENIC PLANTS

CROSS-REFERENCE TO RELATED APPLICATIONS

This application is a Continuation-in-Part of U.S. patent application Ser. No. 08/427,097, filed Apr. 21, 1995, issued as U.S. Pat. No. 5,668,294, on Sep. 16, 1997 which is incorporated by reference herein in its entirety.

ACKNOWLEDGEMENT OF FEDERAL RESEARCH SUPPORT

This invention was made in part with funding from the United States Department of Energy. Accordingly, the United States government may have certain rights in this invention.

BACKGROUND OF THE INVENTION

The field of this invention is the area of plant molecular biology, and it relates in particular, to metal and organometal resistance genes functional in plants, transgenic plants containing same, and methods for remediation of environmental metal and organometal contamination using the transgenic plants of the present invention, especially using plants which detoxify organomercurial compounds.

Contamination of the environment with metal ions and/or organic, hydroxide and thiol derivatives of metals has increased over the last several decades, with toxic levels of the contaminants being reached in air, water and/or soil in certain locations. Contamination may stem from human and industrial sources, or in certain locales, the soil is contaminated naturally with such toxic metals as arsenic, cadmium, copper, cobalt, lead, mercury, selenium and/or zinc.

Mercury is often found in soil, aquatic and marine sediments as thiol salts, as chelates with acidic humic substances, as methylmercury and to a lesser extent other organomercurials, as hydroxides and as free $Hg^{++}$. Mercury cycles through the aqueous phase and into the atmosphere as volatile elemental Hg and methylmercury, and is then oxidized and washed by rain into the marine environment [Barkay et al. (1992) *Biodegradation* 3:147–159]. Some bacteria in soil and sediments can detoxify ionic mercury by reducing it to its metallic form in an NADPH-coupled reaction, which is efficiently catalyzed by mercuric ion reductase.

Mercury is also often found bound in the form of organomercurial compounds in contaminated animals and microbes [Barkay et al. (1992) supra; Robinson and Tuovinen (1984) *Microbiological Reviews* 48:95–124]. Sulfate-reducing bacteria living in the aerobic-anaerobic interface in contaminated environments can convert mercuric ion to methyl mercury. In fish, where mercury toxicity is well studied, most of the tissue-associated mercury is found as methylmercury, and its production may be the product of nonenzymatic and enzymatic reaction of $Hg^{++}$ with methyl-B12 [Pan Hou and Imura (1987) *Arch. Microbiol.* 131:176–177]. The prevailing theory, supported by convincing evidence, is that most methyl mercury is produced catalytically by sulfate-reducing bacteria living at the aerobic/anaerobic interface (Choi et al. (1994) *Appl. Environ. Micro.* 60, 1342–1346; Choi et al., (1994) *Appl. Env. Microbiol.* 60, 4072–4077). This activity is particularly high in aquatic environments, and hence the well-publicized link to the aquatic food chain (see below). Although both the mono- ($CH_3Hg^+$) and dimethyl ($Hg(CH_3)_2$) forms of methyl mercury are extremely toxic (Clarkson, T. W. (1994) In: *Mercury Pollution Integration and Synthesis*, C. J. Watras, and J. W. Huckabee, eds., Lewis Publishers Ann Arbor, Mich., pp. 631–642), the latter is very mobile in both liquid and gaseous phases and is more easily transported through cell membranes than thiol bound Hg(II) or free mercury ion. This mobility is apparently what makes methyl mercury such an environmental hazard. High levels of both thiol bound Hg(II) and methy mercury are found in organisms—worms, shrimp, crabs, bottom-feeding fish—that come in direct contact with contaminated sediment, but relatively little Hg(II) is found further up the food chain. However, methyl mercury is the principal mercury compound that is concentrated or "biomagnified" up the food chain from bacteria living on detritus at the sediment-water interface to bottom feeders and then on to fish, birds, and mammals (Gardner et al. (1978) *Environ. Pollut.* 15, 243–251). Methyl mercury has had a tragic impact on humans and animals, and it is often lethal. The first to show symptoms in the infamous Minamata Bay incident (D'Itri and D'Itri (1978) *Environ. Management* 2, 3–16) were birds and cats and then humans. The mercury found in all three species was be traced directly to methyl mercury-contaminated fish in the bay. The characterized neurological diseases and proposed immunological diseases produced by methyl mercury in animals and humans are so far untreatable. Methylmercury is volatile, and both mono- and dimethylmercury are extremely toxic [D'Itri and D'Itri (1987) *Environ. Management* 2:3–16].

The bacterial gene merA used by the present inventors is derived from the transposon Tn21, which was originally isolated from the Incompatibility Group IncFII resistance plasmid NR1 [see e.g., Gilbert and Summers (1988) *Plasmid* 20:127–136]. The product of the bacterial merA gene is mercuric ion reductase (MerA). MerA can detoxify ionic mercury by reducing it to its less toxic (insoluble and volatile) elemental form ($Hg^0$). MerA belongs to a family of reductase enzymes which are related in their primary structures. As a family, these reductases act on a wide variety of organic and thiol substrates in addition to the thiol salts of divalent Hg.

Certain bacterial mer operons also encode an organomercurial lyase (MerB, methylmercury lyase, R831b merB gene product) which catalyzes the protonolytic cleavage of carbon-mercury bonds, e.g., $RCH_2Hg^+ \rightarrow Hg^{++} + RCH_3$, and together with MerA, produces what is termed broad spectrum mercury resistance (resistance to both thiolmercury and organomercurials including alkylmercury compounds and resistance to mercuric ion). The MerB protein cleaves a variety of carbon-mercury compounds, from methylmercury to long chain hydrocarbon and aromatic derivatives [Begley et al. (1986a) *Biochemistry* 25:7186–7192; Begley et al. (1986b) ibid. 7192–7200]. This process removes methylmercury or other organomercurials and then metallic mercury from the environment.

Additional genes which often occur within bacterial mer operons include merT (mercury transport through the cell membrane) and merP (mercury sequestration in the periplasmic space of gram-negative bacteria). Mercury resistance genes are reviewed in Summers, A. O. (1986) *Ann. Rev. Microbiology* 40:607–634.

Regions which are naturally contaminated with heavy metals are often characterized by scrubby heavy-metal tolerant vegetation [Brooks and Malaisse (1985) *The Heavy Metal-tolerant Flora of South Central Africa*, A.A. Balkema Press, Boston, Mass.; Wild, H. (1978) "The Vegetation of Heavy Metal and Other Toxic Soils," in *Biogeography and Ecology of Southern Africa*, Wergren, M. J. H., ed, Junk, The Hague, Netherlands]. Certain of these naturally occurring metal-resistant plants hyperaccumulate large amounts of heavy metals. These plants have been found in a variety of habitats, but often they exhibit bizarre metal ion requirements, grow poorly in less exotic habitats, and are of little direct economic value as crop or forest species.

There is a long felt need in the art for the in situ remediation of toxic metal ions and especially toxic organometal compounds (e.g., alkyl and/or aryl metal adducts). The present invention enables phytoremediation and/or revegetation of contaminated environments via the plant-expressible organometal lyase coding sequences, especially organomercurial lyases and mercuric ion reductase, alone or in combination with plant-expressible metal ion reductases, as disclosed herein.

SUMMARY OF THE INVENTION

The present invention provides plant-expressible coding sequences which mediate resistance to and detoxification of toxic organometal compounds, and optionally, plant-expressible toxic metal ion reductase coding sequences as well, in transgenic plants or plant cells which express these coding sequences encoding organometal lyase. Desirably these sequences are those of organomercury lyase and mercury (ion) reductase. Preferably the coding sequence is that of plant-expressible merB (which encodes organomercury lyase). The specifically exemplified merB coding sequence is expressible in plants when operably linked to transcription and translation control sequences which are functional in plant cells. The expression of the plant-expressible merB in plants confers to resistance to and/or the ability to detoxify organomercurials including, but not limited to, alkylmercury compounds wherein the alkyl group is either straight chain or branched, alkenyl mercury compounds, allyl mercury, alkynyl mercury compounds, aromatic mercury compounds, wherein there are from one to about 6 aromatic rings, and other organomercurials including but not limited to humic acid-containing mercury compounds. The exemplified MerB protein also mediates resistance to and/or detoxifies organo-metals including, but not limited to, organic lead, organic cadmium and organic arsenic compounds, where those organometals can be alkyl, aklenyl, alkynyl or aromatic metal compounds.

As specifically exemplified, the plant-expressible metal ion reductase/resistance coding sequences include merApe9, merApe20, merApe29, merApe38, merApe47 and merApe100, as disclosed herein (See FIGS. 1–2 and Tables 4–10).

Another aspect of the present invention are plant-expressible organometal resistance coding sequences operably linked to transcriptional and translational control sequences which are functional in plants. Preferably the coding sequence is that of plant-expressible merB (which encodes organomercury lyase) (see, e.g., Table 11).

Where resistance to and/or detoxification of organomercurials and resistance to and reduction of mercuric ion is also desired, the plant also contains a plant-expressible gene encoding metal ion (especially mercury) ion reductase, preferably the plant-expressible metal resistance/metal coding sequences include, but are not limited to, merApe9, merApe20, merApe29, merApe38, merApe47 or merApe100, as disclosed herein (See FIGS. 1–2) and a plant-expressible merB sequence (see Table 11, SEQ ID NOs:33–34).

A further aspect of the present invention are transgenic plant cells, plant tissue and plants which have been genetically engineered to contain and express a plant-expressible organometal lyase coding sequence operably linked to transcriptional and translational control sequences which are functional in plants. Preferably the coding sequence is that of a plant-expressible merB. Where resistance to and reduction of mercuric ion is also desired, the plant should also contain and express a metal ion reductase coding sequence, for example, a plant expressible mercury reductase sequence. As specifically exemplified, the plant-expressible mercury resistance/reductase coding sequences include merApe9, merApe20, merApe29, merApe38, merApe47 or merApe100, as disclosed herein (See FIGS. 1–2). Plants expressing both the metal ion reductase and the organometal lyase can be produced by traditional plant breeding crosses of plants genetically engineered to contain and express single plant-expressible metal resistance coding sequences or by genetically engineering a plant in one or more steps to contain both types of plant-expressible sequences.

Also provided by the present invention are methods for effecting organometal resistance and/or detoxification in plants, plant cells or plant tissue, by stably transforming a plant to contain and express a nucleotide sequence of a plant-expressible organometal resistance coding sequences operably linked to transcriptional and translational control sequences which are functional in plants, plant cells and plant tissue. Desirably, that organometal lyase coding sequence encodes a organomercury lyase; a preferred coding sequence is that of the plant expressible merB as specifically exemplified in Table 11, nucleotides 40–678. See also SEQ ID NOs:33–34. Where resistance to and reduction of mercuric ion is also desired, the plant also contains and expresses a plant-expressible metal ion reductase such as mercury reductase. The merBpe can be used as a selective marker in transformation of plant cells and plant tissue. Selection for transformed cells and/or transformed plant tissue can be carried out on media containing an organomercurial which prevents growth or survival of plant cells or tissues which do not express the MerB protein. For example, 1–3 $\mu$M phenylmercuric acetate can be used to select plant cells or tissue genetically engineered to contain and express a merB coding sequence. Optionally, the merBpe can be used in conjunction with a plant-expressible merA. Preferably the coding sequence is that of a plant-expressible merA (which encodes mercury reductase). As specifically exemplified, the plant-expressible metal resistance coding sequences are include merApe9, merApe20, merApe29, merApe38, merApe47 and merApe100, as disclosed herein (See FIGS. 1–2, Tables 4–10).

A further aspect of the invention are plant-expressible nucleotide sequences which mediate resistance to and/or detoxification of organomercurial compounds in conjunction with the plant-expressible metal resistance/reductase coding sequences of the present invention. As specifically exemplified herein, the coding sequence mediating organometal resistance is that of merB, which encodes methylmercury lyase, which has been adapted for plant gene expression as disclosed herein (See FIG. 4).

BRIEF DESCRIPTION OF THE DRAWINGS

FIGS. 1A–1D illustrates the construction of merApe9 by overlap extension polymerase chain reaction (OE PCR). The primers used to prepare the "a" and "b" fragments are shown below the merA map. The "a" and "b" fragments were joined in a PCR reaction using the "a" and "b" fragments as templates and the 5'S and 3'N primers. Primer sequences are given in Table 2 hereinbelow. pNS2 contains modified 5' and 3' flanking sequences with bacterial ribosome binding sites (SD) and consensus plant translation signals (PT) as well as restriction sites to be used in subsequent cloning experiments.

FIG. 4 presents a schematic for PCR modification and cloning of merB to make merBpe. The merB coding sequence contained on a fragment of the mer operon in pCT12 (subcloned from R831b) was PCR amplified with long mutagenic primers that altered its 5' and 3' flanking sequences immediately adjacent to its start and stop codon. This fragment was cut with BamHI and HindIII and cloned into the corresponding replacement region of pBSKII under control of the bacterial lac operator-promoter region. Synthetic bacterial translation signals (SD—Shine Delgarno), plant and animal consensus translation signals (PT/AT), a stop codon to end β-gal translation, and appropriate restriction endonuclease cloning sites were introduced from the primers.

DETAILED DESCRIPTION OF THE INVENTION

Figures 1A, 1B:
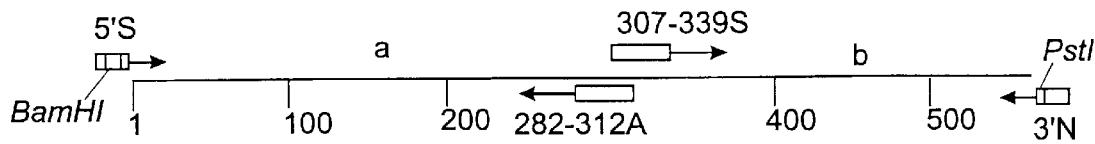

Because metal contamination of the environment is a problem, it is imperative that modern technology provide solutions which are economical in terms of money and natural resources and which are also safe for the environment.

As used herein, the term "metal ion resistance" means that a non-naturally occurring organism is not inhibited by the presence of at least one of divalent cations of mercury, cadmium, cobalt, trivalent cations of gold, and monovalent silver ion, at concentrations (levels) at which a naturally occurring (wild-type) counterpart of the non-naturally occurring organism is inhibited or exhibits symptoms of toxicity. Resistance is achieved by rendering the metal ion less toxic. It is not intended that the term metal resistance refer to resistance to unlimited concentration of metal ions, but rather the term is relative in that it relies on comparison to the properties of a parental strain.

A "metal resistance ion coding sequence" is one which encodes a protein capable of mediating resistance to and/or detoxification of at least one metal ion, including, but not limited to, divalent cations of mercury, nickel, cobalt, trivalent cations of gold, and by monovalent cations of silver. Also within the scope of this definition are mutant sequences which determine proteins capable of mediating resistance to divalent cations of lead, cadmium and copper.

An "organomercurial resistance coding sequence" is one whose protein product mediates resistance to and/or detoxification of such organic mercury compounds as alkylmercurials, alkenylmercurials, alkynylmercurials, and certain aromatic mercurials, typically in conjunction with a metal resistance gene such as merA. As specifically exemplified herein, the organomercurial resistance gene is the methylmercury lyase gene merB) and its gene product confers resistance to organomercurial compounds such as alkylmercury compounds (including but not limited to methylmercury, ethylmercury, propionylmercury), alkenylmercurials, alkynylmercurials, and aromatic mercurials including, but not limited to, p-chloromercuribenzoate (PCMB), phenyl mercury acetate (PMA), and certain other organomercurials such as humic acid complexes, especially in conjunction with the merA gene product (mercury ion reductase) in bacteria. The MerB protein also confers resistance to and/or detoxification of organometals, including but not limited to, organocadmium, organoarsenic and organolead, in the forms (alkyl, etc) corresponding to those set forth for mercurials. Surprisingly, plants genetically engineered to contain and express the merB coding sequence alone are resistant to organomercurial compounds.

With respect to a coding sequence, the term "plant-expressible" means that a coding sequence (nucleotide sequence) can be efficiently expressed by plant cells, tissue and whole plants. The art understands that a plant-expressible coding sequence has a GC composition consistent with good gene expression in plant cells, a sufficiently low CpG content so that expression of that coding sequence is not restricted by plant cells, and codon usage which is consistent with that of plant genes. Where it is desired that the properties of the plant-expressible metal or organometal resistance gene are identical to those of the naturally occurring metal or organometal resistance gene, the plant-expressible homolog will have a synonymous coding sequence or a substantially synonymous coding sequence. A substantially synonymous coding sequence is one in which there are one or more codons which encode a similar amino acid to a comparison sequence, or if the amino acid substituted is not similar in properties to the one it replaces, that change has no significant effect on enzymatic activity for at least one substrate of that enzyme. As discussed hereinbelow, it is well understood that in most cases, there is some flexibility in amino acid sequence such that function is not significantly changed. The skilled artisan understands such conservative changes in amino acid sequence, and the resultant similar protein can be readily tested without the expense of undue experimentation using procedures such as those disclosed herein. Where it is desired that the plant-expressible gene have different properties, there can be variation in the amino acid sequence as compared to the wild-type gene, and the properties of metal resistance can be readily determined as described herein, again without the expense of undue experimentation. It is further well understood in the art that a plant expressible coding sequence must be operably linked to transcriptional and translational control sequences which are functional in plant cells, plant tissue and plants.

"Plant-expressible transcriptional and translational regulatory sequences" are those which can function in plants, plant tissue and plant cells to effect the transcriptional and translational expression of the nucleotide sequences with which they are associated. Included are 5' sequences to a target sequence to be expressed which qualitatively control gene expression (turn on or off gene expression in response to environmental signals such as light, or in a tissue-specific manner) and quantitative regulatory sequences which advantageously increase the level of downstream gene expression. An example of a sequence motif which serves as a translational control sequence is that of the ribosome binding site sequence. Polyadenylation signals are examples of transcription regulatory sequences positioned downstream of a target sequence, and there are several well known in the art of plant molecular biology; these include the 3' flanking sequences of the nos gene.

A "non-naturally occurring recombinant nucleic acid molecule", e.g., a recombinant DNA molecule, is one which does not occur in nature; i.e., it is produced either by natural processes using methods known to the art but is directed by man to produce a desired result, or it has been artificially produced from parts derived from heterologous sources, which parts may be naturally occurring or chemically synthesized molecules or portions thereof, and wherein those parts have been joined by ligation or other means known to the art.

A "transgenic plant" is one which has been genetically modified to contain and express heterologous DNA sequences, either as regulatory RNA molecules or as proteins. As specifically exemplified herein, a transgenic plant is genetically modified to contain and express at least one heterologous DNA sequence operably linked to and under the regulatory control of transcriptional control sequences which function in plant cells or tissue or in whole plants. As used herein, a transgenic plant also refers to progeny of the initial transgenic plant where those progeny contain and are capable of expressing the heterologous coding sequence under the regulatory control of the plant-expressible transcription control sequences described herein. Seeds containing transgenic embryos are encompassed within this definition as are cuttings and other plant materials for vegetative propagation of a transgenic plant.

When plant expression of a heterologous gene or coding sequence of interest is desired, that coding sequence is operably linked in the sense orientation to a suitable promoter and advantageously under the regulatory control of DNA sequences which quantitatively regulate transcription of a downstream sequence in plant cells or tissue or in planta, in the same orientation as the promoter, so that a sense (i.e., functional for translational expression) mRNA is produced. A transcription termination signal, for example, as polyadenylation signal, functional in a plant cell is advantageously placed downstream of the metal or organometal resistance coding sequence, and a selectable marker which can be expressed in a plant, can be covalently linked to the inducible expression unit so that after this DNA molecule is introduced into a plant cell or tissue, its presence can be selected and plant cells or tissue not so transformed will be killed or prevented from growing. In the present invention, the mercury resistance coding sequence can serve as a selectable marker for transformation of plant cells or tissue. Where constitutive gene expression is desired, suitable plant-expressible promoters include the 35S or 19S promoters of Cauliflower Mosaic Virus, the nos, ocs or mas promoters of *Agrobacterium tumefaciens* Ti plasmids, and others known to the art. Where tissue specific expression of the plant-expressible metal resistance coding sequence is desired, the skilled artisan will choose from a number of well-known sequences to mediate that form of gene expression. Environmentally regulated promoters are also well known in the art, and the skilled artisan can choose from well known transcription regulatory sequences to achieve the desired result.

Plants have a number of advantages as agents for a metal remediation strategy. First, plants have the genetic capacity (using hundreds, even thousands, of genes) to extract at least 16 metal cation and oxyanion nutrients from the soil and ground water. This capacity can be chemically and genetically manipulated to extract environmental pollutants. Second, plants have extensive root systems to help in this mining effort; typical estimates are as high as $100\times10^6$ miles of roots per acre [Dittmer, H. J. (1937) *Amer. J. Botany* 24:417–420]. The root systems of various macrophytes can reach up to 40 feet into the soil. In addition, plants are photosynthetic and govern as much as 80% of the available energy at any given time in most ecosystems. Through photosystem I (a system not found in photosynthetic bacteria), they use light energy to generate large amounts of reducing power (as NADPH) that can be used to efficiently reduce metal ions. Plants photosynthetically fix $CO_2$ and reduce it to make their own carbon/energy source. This reduced carbon energy is used by plant roots to live heterotrophically. This redox power can also be used to reduce toxic metal ions like Hg(II) [Rugh et al. (1996) supra]. Many plants can produce large amounts of biomass annually with the potential both to enrich contaminated soil with carbon and nutrients and/or remove metal ions from the soil.

An additional benefit of the metal resistant plants is their ability to harvest metals; precious and semi-precious metals can be reduced and thereby trapped in plant tissues. These metals include can include gold, silver, platinum, rhenium, copper, palladium, nickel, zinc and cadmium, where the corresponding metal ions are reduced by the metal resistance gene product in those plants.

The metal resistance protein (MerA protein, mercuric ion reductase) is exemplified by that from Tn21, a bacterial mercury resistance transposon originally isolated from the IncFII plasmid NR1. The amino acid sequence is given in SEQ ID NO:2. In addition to reducing mercuric ions, the Tn21 MerA reduces trivalent gold and monovalent silver cations [Summers and Sugarman (1974) *Journal of Bacteriology* 119:242–249]. Monovalent silver and certain divalent metal cations have been shown to be competitive inhibitors of mercuric ion reduction in vitro [Rinderle et al. (1983) *Biochemistry* 22:869–876]. Data obtained by the present inventors indicate that MerA mediates resistance to trivalent gold, divalent cobalt, divalent copper and divalent nickel cations as well as divalent ionic mercury.

Because mercury resistant plants are desirable for their potential roles in revegetation of contaminated soils (e.g., subsequent to mining operations) and/or bioremediation of soils and/or aquatic environments contaminated with ionic mercury, the naturally occurring merA coding sequence derived from the bacterial transposon Tn21 was incorporated in transgenic plants under the regulatory control of the Cauliflower Mosaic Virus 35S plant-expressible promoter. Functional MerA protein was expressed in transgenic plants only after extensive modification of the coding sequence to reduce the GC content and to conform codon usage to that commonly used in plants and transcriptional and translational control sequences (see hereinbelow).

Examination of the merA coding sequence [Barrineau et al. (1984) *Journal of Molecular and Applied Genetics* 2:601–619] revealed that the 1695 nucleotide open reading frame contains 67% G+C and 218 CpG dinucleotides. Those CpG dinucleotides and codons skewed for G or C in the third nucleotide are uncommon in plants [McClelland and Ivarie (1982) *Nucleic Acids Research* 10:1865–7877; Murray et al. (1989) *Nucleic Acids Research* 17:477–494] as well as in *Escherichia coli* [Phillips and Kushner (1987) *Journal of Biological Chemistry* 262:455–459]. Raina et al. (1993) *Proc.Natl. Acad. Sci. USA* 90:6355–6359 have reported that plant promoters are often hypermethylated and turned off when adjacent to CpG-rich sequences.

Figure 1D:
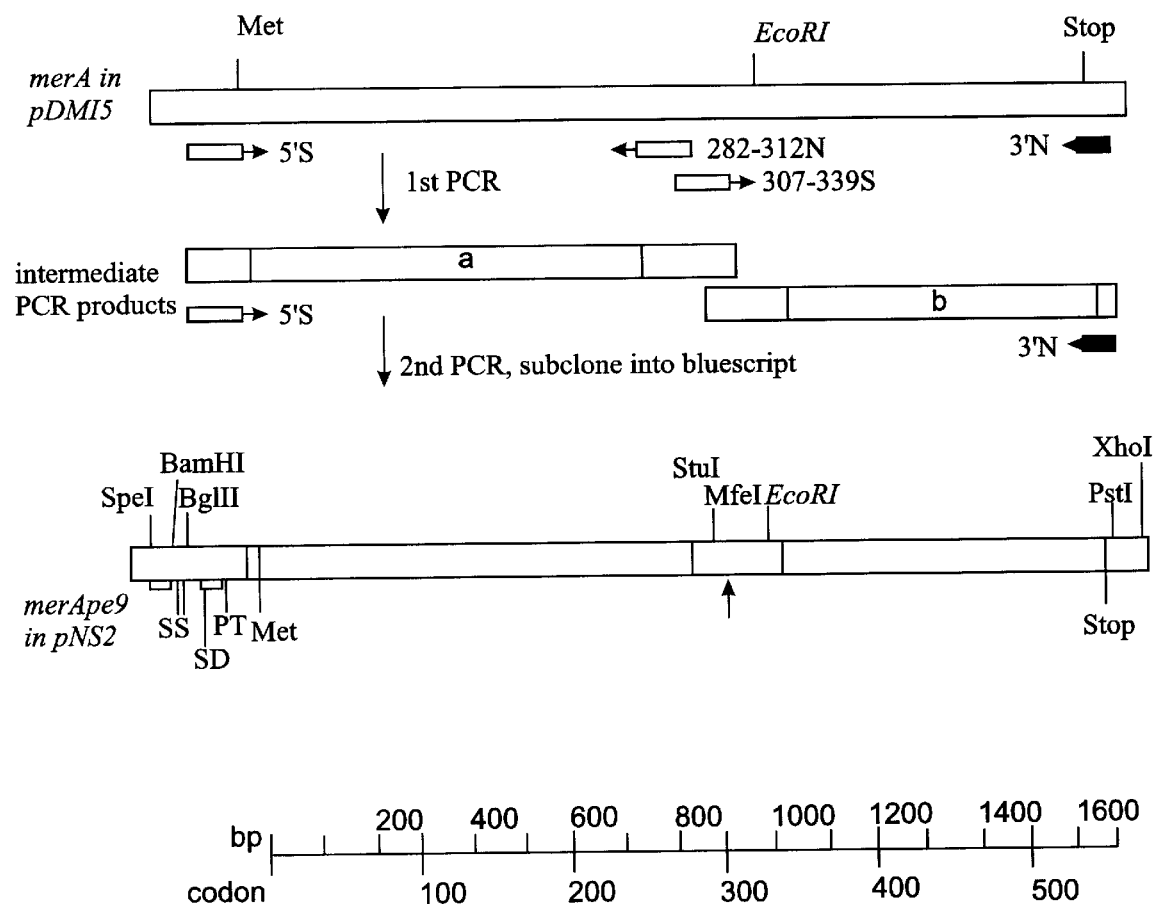

The present inventors have constructed DNA sequences which encode a metal ion resistance protein which is expressed in plant cells. As specifically exemplified, these modified sequences are presented in FIGS. 1 and 2. The deduced amino acid sequence for the naturally occurring heavy metal resistance protein MerA (mercury ion reductase) is given in SEQ ID NO:2. The open reading frame extends from an ATG beginning at nucleotide 14 through the stop codon ending at nucleotide 1708 in SEQ ID NO:1. Sequences for MerApe 9, MerApe 20, MerApe29, MerApe 38, MerApe 48 and MerApe100 are provided herein.

The function of the MerA proteins synthesized by *E. coli* cells expressing the merApe9 and merApe38 sequences are reflected in the mercury resistance phenotypes of strains carrying pNS2 and pNS5 (See Table 1 and Example 6). *E. coli* cells which express all of the mer operon except a functional reductase (merA) exhibit mercury hypersensitivity. A culture of isogenic *E. coli* hypersensitive to mercury which contains pBluescript without insert served as a negative control. Control cells were hypersensitive to mercuric ion and totally inactive in the reduction of mercuric ions.

Figure 3:
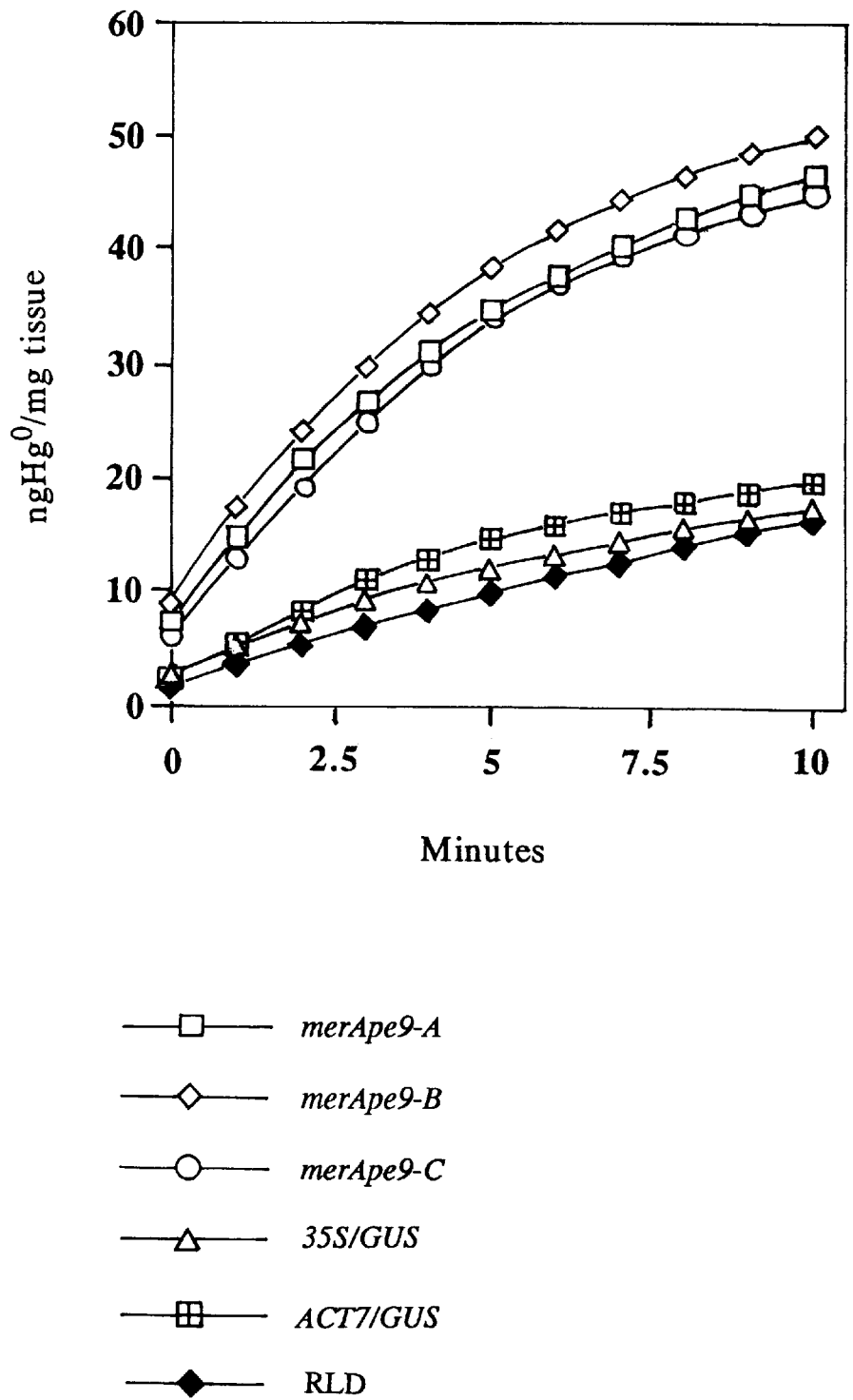
FIG. 3 illustrates the evolution of $Hg^0$ with time in control *Arabidopsis thaliana* var. RLD plants, and representative transgenic plants expressing merApe9. (Mercury evolution by transgenic plants expressing merApe 9: -□- merApe9-A, -◇- merApe9-B, -○- merApe9-C; -◆- *A. thaliana* RLD control, -△- transgenic plant expressing GUS gene under CaMV 35S promoter control, -▫-transgenic plant expressing GUS under control of Actin 7 promoter).
Figure 5A:
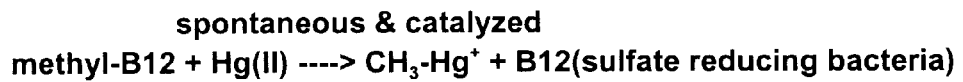
FIG. 5 illustrates reactions involving ionic and methyl mercury. Mono-methyl mercury is formed catalytically from Hg(II) by sulfate-reducing bacteria living in the anaerobic-aerobic interphase at these sites. Organomercury lyase (MerB) catalyzes the protonolysis of organomercury compounds like MeHg or benzyl mercury to release free mercury ions (Hg(II)). In addition, MerB protonolyzes the carbon-mercury bond of a wide range of organic mercury compounds (e.g., ethyl mercury, vinyl mercury, propenyl mercury, and phenyl mercury), freeing the mercuric ion, Hg(II) [Begley et al. (1986a) supra; Begley et al. (1986b) supra]. Ionic mercury reacts rapidly with the sulfhydryl groups on any available thio-organic compound, forming very stable thiol salts, e.g., $(RS)_2Hg$. Mercuric ion reductase (MerA) removes mercury from these stable thiol-salts by electrochemically reducing it to the less toxic, relatively volatile metallic mercury Hg(0) in an NADPH-coupled redox reaction [Walsh et al. (1987) *Flavins and Flavoproteins: Proceedings of the Ninth International Symposium*. pp. 13–28].
Figure 5B:
Figure 5C:
Figure 5D:
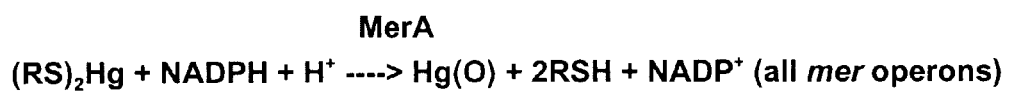

Transgenic plant tissue containing and expressing the merApe9 coding sequence mediated the evolution of elemental mercury at levels significantly greater than for control plant tissue (See FIG. 3 and Example 7). 10 mg of transgenic MerA$^+$ seedling tissue evolved about 500 ng Hg$^0$ during the 10 minute assay period. Control untransformed plants and transgenic plants expressing the unrelated β-glucuronidase (GUS) gene under the control of the CaMV 35S promoter or the Actin7 promoter did not evolve significant amounts of elemental mercury during the incubation period (<1 ng Hg$^0$/50 mg plant tissue/10 min).

It is understood that nucleic acid sequences other than that of SEQ ID NO:1, from nucleotide 14 through nucleotide 1708, or merApe20, merApe29, merApe38, merApe47 or merApe100 will function as coding sequences synonymous with the exemplified merApe9 coding sequence. Nucleic acid sequences are synonymous if the amino acid sequences encoded by those nucleic acid sequences are the same. The degeneracy of the genetic code is well known to the art; i.e., for many amino acids, there is more than one nucleotide triplet which serves as the codon for the amino acid; for expression in plant cells or tissue it is desired that codon usage reflect that of plant genes and that CpG dinucleotides be kept low in frequency in the coding sequence. It is also well known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Vol. 5, Suppl. 3, pp. 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

PCR was used to amplify the MerB coding region SEQ ID NO:15 from within a cloned fragment of the mer operon isolated from the broad host range plasmid R831b. We constructed a modified merB gene, merBpe, in which the 5' region immediately upstream from the initiator ATG codon was replaced with consensus plant and *E. coli* translation signals similar to those designed in Rugh et al. (1996) supra. Appropriate restriction sites were added to both flanking regions, as shown in FIG. 4. The PCR product was cloned into an *E. coli* expression vector under control of the *E. coli* lac promoter. The ligation mix was transformed into a "wild type" *E. coli* strain, SK1592, containing the pDU202 plasmid, which encodes a wild-type, narrow spectrum resistance operon (i.e., it encodes a mercuric ion reductase and confers resistance to Hg(II) but not to organomercurial compounds). Ampicillin-resistant transformants were selected and screened for organomercurial resistance.

The functionality of the merBpe construct in pmerBpe was confirmed by assaying for organomercury lyase activity in *E. coli*. The size of the zone of sensitivity around disks containing phenylmercury acetate (PMA) are shown for various strains in Table 2. The parent E. coli strain, SK1592, with both pDU202 and a control pBluescript vector plasmid [Barrineau and Summers (1983) Gene 25:209–221] was very sensitive to PMA, producing a large ring of growth inhibition with organomercurials like PMA (PMA, 23 mm; PMCB 13 mm). This strain can reduce thiol-bound Hg(II) in the cell because it has a functional merA gene, but it cannot break down organomercurials such as PMA. When this strain contained the pmerBpe plasmid instead of the control vector, it showed high levels of organomercurial resistance (PMA, 9 mm; PCMB, 10 mm). These results demonstrated that merBpe encoded a fully functional organomercurial lyase. We note that the product of MerB action on PCMB is still an antibacterial agent, chlorobenzoate; thus, the resistance due to removal of mercury from this organomercurial compound is somewhat limited in the bacterial host cell. DNA sequence analysis confirmed that pmerBpe encodes a normal MerB the protein coding region and contains the correctly modified flanking sequences.

The merBpe sequence was subcloned as a BamHI/XhoI fragment into the commercially available plant expression vector, pVST1, to make pVSTmerB. In this construct, the merBpe gene was under control of the constitutive plant CaMV 35S promoter and plant NOS 3' polyadenylation signals in a T-DNA binary vector. Using an *Agrobacterium tumefaciens* bacterial host to mediate plant cell transformation, this construct was transformed into Arabidopsis (RLD) with selection for the kanamycin resistance marker linked to merBpe. Plantlets from the various transgenic shoots (T0 generation) were transferred to soil, fed topically, allowed to set seed (T1 generation) [An et al. (1996) Plant Cell 8:15–30].

Second generation (T1) seeds, seedlings, and plants from several independent transgenic lines expressing merBpe were resistant to 1–3 $\mu$M PMA in the growth media. Typically 50–75% of the seeds from most merBpe lines germinated at these concentrations. On PMA-containing agar they grew at rates comparable to those for controls germinated in the absence of any selective agent. Seeds, seedlings, or mature plants from non-transgenic controls (RLD), transgenic lines containing other unrelated T-DNA constructs and lines expressing merApe9 [Rugh et al. (1996) supra], the mercuric ion reductase did not germinate and/or died shortly after germination on 1 $\mu$M or greater concentrations of PMA. Even at concentrations of PMA that killed 100% of all RLD seeds, seedlings, and juvenile plants, the transgenic merBpe-expressing lines showed vigorous root growth. Alternatively, and in an independent experiment, plantlets derived from transgenic shoots were selected directly on 1 $\mu$M PMA.

Figure 6A:
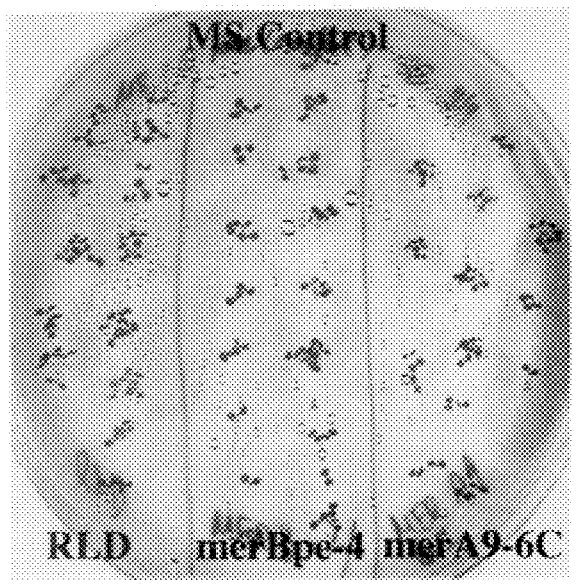
FIG. 6 shows that transgenic Arabidopsis plants grow well on toxic levels of organic mercury. The synthetic BamHI site from the merB5'S oligonucleotide and a XhoI site in the plasmid multilinker flanking the 3' end of merApe9 in the pNS2 plasmid clone (see materials and methods) were cleaved and the resulting fragment was ligated into the BamHI/XhoI replacement region of the T-DNA binary plant expression vector PVSTI [Malik and Wahab (1993) *J. Plant Biochem. Biotech.* 2:69–70]. This placed the merB under control of the constitutive CaMV 35S promoter and used the NOS 3' polyadenylation signals to make a 35S/merBpe/nos construct (see FIG. 4). Second generation (T1) seeds from RLD plants transformed with this merB construct, RLD control plants and plants expressing merApe9 alone were plated on normal MS media A. and B. MS media containing 2 μM PMA and grown for two weeks. Left—Transgenic line expressing merApe9 [Rugh et al. (1996) *Proc. Natl. Acad. Sci. USA* 93:3182–3187]. Center—transgenic line expressing merBpe. Right—RLD parent line.
Figure 6B:
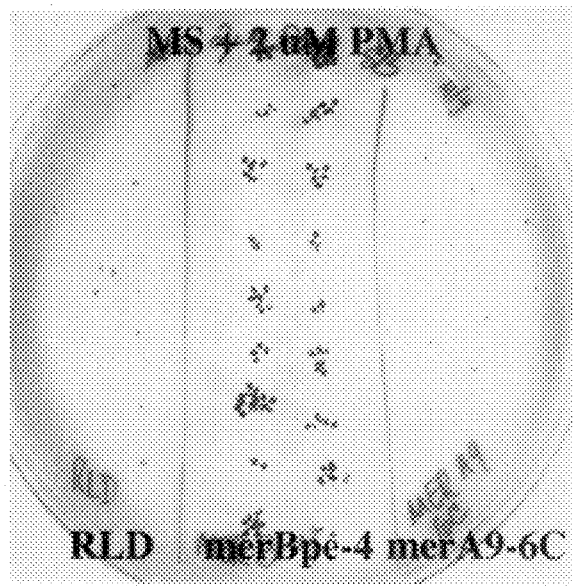

Mono methyl mercury (MeHg+) is the major form of environmental mercury that is biomagnified up the food chain. Although the MerB enzyme has a broad substrate range for organic mercury compounds, the enzyme is significantly less efficient at catalyzing the breakdown of MeHg+ than of PMA. Therefore, we assayed the resistance of plants to this environmentally important compound. Second generation (T1) seeds, seedlings, and plants from several independent transgenic Arabidopsis plant lines expressing merBpe were resistant to 1–3 $\mu$M methyl mercury chloride incorporated into the growth medium as are shown in FIG. 6. The results were different from those on PMA in that 50–75% of the control and experimental lines germinated at these concentrations of methyl mercury chloride and all grew similarly for about one week. After 10 days the RLD controls and merApe9-expressing plants turned yellow, and after two weeks these plants then turned white and died. At these concentrations the merBpe-expressing plants grew at rates comparable to unchallenged controls, and they continued to grow normally until they set flowers and seed. In addition, the transgenic merBpe-expressing lines showed vigorous root growth with 1–3 $\mu$M methyl mercury chloride in the agar medium.

MerB-expressing plants can be used in the remediation of a mercury-contaminated aquatic (or soil) ecosystem to block the biomagnification of methyl mercury up the food chain. Aquatic grasses and deep-rooted trees like cottonwood and sweetgum, which inhabit bottom lands, can be engineered to express merB. These species have roots that grow in the same general area of the sediment as sulfate-reducing bacteria. As the transgenic plant roots take up methyl mercury, MerB breaks the carbon mercury bond to produce Hg(II). Hg(II) is a highly reactive metal ion and should end up sequestered in plant tissues bound to various thiol groups. Desirably, the merB-expressing plants also contain and express an appropriately modified (for expression in plant cells) merA gene.

In plants also expressing merA, the mercuric ion reductase, Hg(II) produced from the MerB reaction and additional Hg(II) taken up from the environment through its normal mining of nutrients is reduced to Hg(0). Hg(0) is released directly from the roots or transpired up the vascular system of the plant, as are waste gasses like $CO_2$ from some plants [Dacey, J. W. (1980) Science 210: 1017–1019; Dacey, J. W. (1981) Ecology 62:1137; Raven et al. (1986) In: *Biology of Plants*, Worth Publishers, N.Y., p.775]. By lowering the total levels in the ecosystem, less methyl mercury will be produced by sulfate-reducing bacteria. Using the MerA and MerB together in transgenic plants at contaminated sites lowers total Hg(II) levels and destroys environmental methyl mercury, thus preventing a large portion of the methyl mercury from moving through the environment.

The Hg(0) entering the environment joins the enormous and stable pool of Hg(0) in the atmosphere (Nriagu (1979) In: The Biogeochemistry of Mercury in the Environment, (New York: Elsevier) with half life of over one year. Because Hg(0) is not easily returned to earth, this pool is not thought to contribute less significantly to manmade contamination of the environment. In contrast, atmospheric Hg(II) species (i.e., mercury released from coal burning or methyl mercury released naturally) are rapidly returned to earth by rain and dry deposition with a half-life of about 1–2 weeks. Thus, volatilization of relatively small amounts of Hg(0) with good air circulation effectively removes mercury from terrestrial and aquatic environments.

Once a transgenic plant population expressing MerA and MerB is established, these plants efficiently process mercury. Over the subsequent few decades these plants remove or detoxify most mercury from at a site. Relying only on currently available biological and chemical processing, the efflux rates of Hg(0) from mercury contaminated sites are extremely slow. At one such government site it is estimated that only 10 kg of the 80,000 kg present in the soil is released as Hg(0) per year (Lindberg et al. (1995) Environ. Sci. Tech. 29, 126–135). The levels of atmospheric mercury at this and most sites (4–10 ug/m$^3$) are 10,000 fold below what the EPA/OSHA recommend as the maximimum allowable levels (U.S. Public Health Service (1994) Toxicological Profile for Mercury. In: *Regulations and Advisories*, U.S. Public Health Service, Washington, D.C., pp. 261–269). Even if transgenic plants at this site increased the efflux rate of metallic mercury 200 times, the level of atmospheric mercury would still be 50 fold below these allowable levels.

The transgenic plants of the present invention allow the efficient removal of toxic metal compounds such as methyl mercury and ionic mercury from soil, sediment, and aquatic environments, thus meeting a longfelt need for efficient bioremediation of metal and organometal contaminated sites.

A plant-expressible transcription and translation regulatory sequence can be operably linked to any promoter sequence functional in plants as understood by the skilled artisan; where a regulatory element is to be coupled to a promoter, generally a truncated (or minimal) promoter is used, for example, the truncated 35S promoter of Cauliflower Mosaic Virus, CaMV). Truncated versions of other constitutive promoters can also be used to provide CAAT and TATA-homologous regions; such promoter sequences can be derived from those of A. tumefaciens T-DNA genes such as nos, ocs and mas and plant virus genes such as the CaMV 19S gene. It will be understood that the goals of a skilled artisan will determine the choice of particular transcriptional (and translational) regulatory sequences. Translational control sequences specifically exemplified herein are the nucleotides between 8 and 13 upstream of the ATG translation start codon for bacterial signals and from nucleotides 1 to 7 upstream of the ATG translation start codon for plants (See FIG. 1B)

A minimal promoter contains the DNA sequence signals necessary for RNA polymerase binding and initiation of transcription. For RNA polymerase II promoters the promoter is identified by a TATA-homologous sequences motif about 20 to 50 bp upstream of the transcription start site and a CAAT-homologous sequence motif about 50 to 120 bp upstream of the transcription start site. By convention, the skilled artisan often numbers the nucleotides upstream of the transcription start with increasingly large numbers extending upstream of (in the 5' direction) from the start site. Generally, transcription directed by a minimal promoter is low and does not respond either positively or negatively to environmental or developmental signals in plant tissue. An exemplary minimal promoter suitable for use in plants is the truncated CaMV 35S promoter, which contains the regions from −90 to +8 of the 35S gene. Where a minimal promoter is used, it is desired that for high levels of gene expression, transcription regulatory sequences which upregulate the levels of gene expression be operably linked thereto. Such quantitative regulatory sequences are exemplified by transcription enhancing regulatory sequences such as enhancers.

Operably linking transcription and translation regulatory sequences upstream of a promoter functional in a plant cell allows the expression of the organometal and/or metal resistance coding sequence operably fused just downstream of the promoter, and the skilled artisan understands spacing requirements and ribosome binding site requirements for translational expression of the coding sequence. The metal resistance coding sequence preferably encodes the merA protein of Tn21, as exemplified by the amino acid sequence in SEQ ID NO:2 and the organometal resistance coding sequence preferably encodes the organomercury lyase having the amino acid sequence as given in Table 11.

In plants, the constitutive plant-expressible transcription and translation regulatory element effects the expression of a downstream plant-expressible metal resistance coding sequence. Data is presented for metal resistance in Arabidopsis thaliana genetically engineered to contain and express a plant-expressible merA coding sequence, in particular, merApe9. See also SEQ ID NO:15. Other plant-expressible metal resistance coding sequences provided by the present invention include merApe20, merApe29, merApe38, merApe47 and merApe100. See also SEQ ID NOs:27, 29, 13, 19 and 31. When resistance to organomercurials is desired plants are genetically engineered to contain and express a plant-expressible merB coding sequence in addition to a plant-expressible merA sequence. Similar results are obtained in other plants, including monocots, dicots and gymnosperms, after stable transformation, as for the Arabidopsis thaliana experiments described herein.

Coding sequences suitable for expression in a plant are operably linked downstream of a constitutive or a regulated promoter construct. Transgenic plants can be constructed using the chimeric gene consisting essentially of the promoter, any additional transcription enhancing sequences, and the desired mercury resistance coding sequence including the necessary sequence signals for its translation.

Alternative plant-expressible metal resistance and organomercury resistance coding sequences which can be expressed include those from merA genes from Tn501 and plasmid R100 [Brown et al. (1983) Biochemistry 22:4089–4095; Misra et al. (1985) Gene 34:253–262] and the merB gene from R831b.

Additionally, or alternatively, induction of the regulated construct can be induced, for example, by treating the transgenic plant or tissue with an inducer suitable for regulating expression of the plant-expressible metal ion or organometal resistance coding sequences of the present invention. The expression of the metal and/or organometal resistance coding sequence can also be regulated by tissue specific transcription regulatory sequences.

A transgenic plant can be produced by any means known to the art, including but not limited to Agrobacterium tumefaciens-mediated DNA transfer, preferably with a disarmed T-DNA vector, electroporation, direct DNA transfer, and particle bombardment and subsequent selection and regeneration [see Davey et al. (1989) Plant Mol. Biol. 13:275; Walden and Schell (1990) Eur. J. Biochem. 192:563; Joersbo and Burnstedt (1991) Physiol. Plant. 81:256; Potrykus (1991) Annu. Rev. Plant Physiol. Plant Mol. Biol. 42:205; Gasser and Fraley (1989) Sci. 244:1293; Leemans (1993) Bio/Technology. 11:522; Beck et al. (1993) Bio/Technology. 11:1524; Koziel et al. (1993) Bio/Technology. 11:194; Vasil et al. (1993) Bio/Technology. 11:1533]. Techniques are well known to the art for the introduction of DNA into monocots as well as dicots, as are the techniques for culturing such plant tissues and regenerating those tissues. Monocots which have been successfully transformed and regenerated include wheat, corn, rye, rice and asparagus. Transformation and regeneration can also be applied to aquatic, salt marsh, and estuarine grasses, including Spartina. For efficient regeneration of transgenic plants, it is desired that the plant tissue used in the transformation possess a high capacity to produce shoots. For example, aspen stem sections have good regeneration capacity. [Devillard, C. III et al. (1992) C.R. Acad. Sci. Ser. VIE 314: 291–298K; Nilsson et al. (1992) Transgenic Research 1: 209–220; Tsai et al. (1994) Plant Cell Rep. 14: 94–97] Poplars have been successfully transformed [Wilde et al. (1992) Plant Physiol. 98:114–120].

Techniques for introducing and selecting for the presence of heterologous DNA in plant tissue are well known. For example, A. tumefaciens-mediated DNA transfer into plant tissue, followed by selection and growth in vitro and subsequent regeneration of the transformed plant tissue to a plant is well known for a variety of plants.

Other techniques for genetically engineering plant tissue to contain an expression cassette comprising a promoter and associated transcription regulatory sequences fused to the metal resistance coding sequence and optionally containing a transcription termination region are to be integrated into the plant cell genome by electroporation, co-cultivation, microinjection, particle bombardment and other techniques known to the art. The metal resistance plant expression cassette further contains a marker allowing selection of the expression cassette in the plant cell, e.g., genes carrying resistance to an antibiotic such as kanamycin, hygromycin, gentamicin, or bleomycin. The marker allows for selection of successfully transformed plant cells growing in the medium containing certain antibiotics because they will carry the expression cassette with resistance gene to the antibiotic.

The following examples use many techniques well known and accessible to those skilled in the arts of molecular biology, in the manipulation of recombinant DNA in plant tissue and in the culture and regeneration of transgenic plants. Enzymes are obtained from commercial sources and are used according to the vendors' recommendations or other variations known to the art. Reagents, buffers and culture conditions are also known to the art. References providing standard molecular biological procedures include Sambrook et al. (1989) *Molecular Cloning*, second edition, Cold Spring Harbor Laboratory, Plainview, N.Y., R. Wu (ed.) (1993) *Methods in Enzymology* 218, Wu et al. (eds.) *Methods in Enzymology* 100, 101, Glover (ed.) (1985) *DNA Cloning*, Vols. I and II, IRL Press, Oxford, UK; and Hames and Higgins (eds.) (1985) *Nucleic Acid Hybridization*, IRL Press, Oxford, UK. References related to the manipulation and transformation of plant tissue include R. A. Dixon (ed.) (1985) *Plant Cell Culture: A Practical Approach*, IRL Press, Oxford, UK; Schuler and Zielinski (1989) *Methods in Plant Molecular Biology*, Academic Press, San Diego, Calif.; Weissbach and Weissbach (eds.) (1988) *Methods for Plant Molecular Biology*, Academic Press, San Diego, Calif.; I. Potrykus (1991) *Ann. Rev. Plant Physiol. Plant Mol. Biol.* 42:205; Weising et al. (1988) *Annu. Rev. Genet.* 22:421, van Wordragen et al. (1992) *Plant Mol. Biol. Rep.* 19:12, Davey et al. (1989) *Plant Mol. Biol.* 13:273, Walden and Schell (1990) *Eur. J. Biochem.* 192:563, Joersbo and Brunstedt (1991) *Physiol. Plant.* 81:256 and references cited in those references. Abbreviations and nomenclature, where employed, are deemed standard in the filed and are commonly used in professional journals such as those cited herein.

All references cited in the present application are expressly incorporated by reference herein.

The following examples are provided for illustrative proposes are not intended to limit the scope of the invention as claimed herein. Any variations in the exemplified compositions and methods which occur to the skilled artisan are intended to fall within the scope of the present invention.

EXAMPLES

Example 1

Plant-expressible merA Coding Sequences

An overlap extension polymerase chain reaction (OE PCR) protocol, based on that of Ho et al. (1989) *Gene* 77:51–50, was used to mutagenize the merA coding sequence derived from Tn21 (SEQ ID NO:1) [Barrineau et al. (1984) *J. Mol. Appl. Molec. Genet.* 2:601–619] to adapt it for plant expressibility. The two halves of the merA sequence were amplified in separate PCR reactions, using pair of sense and antisense mutagenic oligonucleotide primers [5'S (SEQ ID NO:3) and 282-312A (SEQ ID NO:4) and 307-339S (SEQ ID NO:5) and 3'N (SEQ ID NO:6), respectively] and pNH6 as template. SEQ ID NO:3 includes BamHI and BglII recognition sites (GGATCC and AGATCT, respectively), a translation stop codon (TAA) in frame with the merA coding sequence, a consensus Shine-Delgarno bacterial ribosome binding site (AGAAGG) [Stormo et al. (1982) *Nucleic Acids Res.* 10:2971–2996], and potentially important plant translation sequences (AACCACA) [Heidecker and Menning (1986) *Ann. Rev. Plant Physiol.* 37:451–462]. The 3'N primer (SEQ ID NO:6) separated the merA coding sequence form the GC-rich region downstream of the translation stop codon. Where mutagenic primers are used, the length of 99 nucleotides was chosen to maximize the amount of the gene which is changed while minimizing the errors which might be introduced in each oligonucleotide.

Each PCR reaction contained 10 ng pNH6, 1.5 mM $MgCl_2$, 5% DMSO, 100 $\mu$M deoxynucleotide triphosphates, 45 pmol of each oligonucleotide primer as appropriate, 1.5 units Taq polymerase (Boehringer Mannheim Corp., Indianapolis, Ind.) and was carried out for 35 cycles (94° C. 1 min, 42° C. 1 min and 72° C. 2 min). After gel purification, the 5' and 3' fragments were joined in a PCR reaction using identical reaction conditions and the 5'S and 3'S primers (SEQ ID NO:1 and 4, respectively) to produce the NS2 amplimer. The NS2 amplimer was cleaved in the flanking BamHI and PstI sites, ligated into the BamHI/PstI replacement region of the multilinker of pBluescriptSKII(−) vector (Stratagene, La Jolla, Calif.) to produce pNS2, and the ligation mixture was transformed into Hg++− supersensitive *E. coli* (pPB111-47). *E. coli* (pPB111-47) (pNS2) grew well when replica plated onto medium containing 200 $\mu$M $HgCl_2$; the hypersensitive parental strain did not grow on 25–200 $\mu$M $HgCl_2$.

Various merApe coding sequences were developed using the strategy outlined in FIGS. 1A–1D and 2 and the oligonucleotides disclosed in Table 1.

TABLE 1

OLIGONUCLEOTIDE SEQUENCES

5'S (SEQ ID NO: 3)

```
          10        20        30        40        50
CTAGAACTAG TGGATCCCTA GATCTAAGAA GGAACCACAA TG AGCACTCT

Bluescript homology  BglII  Shine-Dalgarno   Start MerA homology

TAA      AACCACA
                                STOP     Plant Translation
                                         Control Sequence
```

TABLE 1-continued

OLIGONUCLEOTIDE SEQUENCES

```
       59
CAAATCAC-3'

3'N (SEQ ID NO: 6)
         10         20         30    36
  TATCGAATTC CTGCAGCCTC ACCCGGCGCA GCAGGA 1-19S (SEQ ID NO: 21)
         10         20         30         40         50
  AAGAAGGAC CACAATGtct ACTCTgAAgA TCACtGGtAT GACTTGtGAC 60         70 73
  TCtTGtGCAG TGCATGTCAA GGA*

282-312N (SEQ ID NO: 4)
         10         20         30         40         50
  CCtATaGCTG GGTCTTCaCG aAAGAAgAGa GTGgaGCGtG CaAGaATgGT 60         70         80         90 92
  CACtTTaGCa CCaAGaCGtG CaAAgGCCTG cGCcAGcTCc AG 549-565N (SEQ ID NO: 22)
         10         20         30         40         50 52
  TCGAATTCCT GCAGCCTtAg CCaGCaCAGC AGctcAGCTG CTTCACATCC TT*

307-339S (SEQ ID NO: 5)
         10         20         30         40         50
  GAAGACCCAG CTATAGGTGA AGCTGTTACT GCTGCATTTC GCATGGAAGG 60         70         80         90 99
  CATTGAAGTG CGTGAGCATA CTCAAGCAAG CCAAGTTGCC TATATCAAT 229-262N (SEQ ID NO: 7)
         10         20         30         40         50
  GCTTCAGTGG AAGTCCAGTA AGGAGTGTCC TTGAGACCAG GAATTGGTGG 60         70         80         90         101
  AACAGCTGGG CTTGCACCAG TGGCAATGAG ACAGCGGTCG AATGCCACCA C 257-293S (SEQ ID NO: 8)
         10         20         30         40         50
  TGGACTTCCA CTGAAGCACT AGTGTCTGAG ACCATTCCAA AGCGTCTTGC 60         70         80         90         100
  AGTCATTGGC TCCTCTGTGG TGGCTCTTGA ACTTGCCCAG GCCTTTGCAC

109
  GTCTTGGTG 334-366N (SEQ ID NO: 11)
         10         20         30         40         50
  CACGACCAGT TGCAACAAGG ACTTTGTCTG CACGAAGTTC ACCATGAGCA 60         70         80         90         100
  GTGGTAAGGA CGAATTCACC ATCACCTTCA CCATTGATAT AGGCAACTTA 361-394S (SEQ ID NO: 12)
         10         20         30         40         50
  TGTTGCAACT GGTCGTGCAC CAAACACTCG CAAACTGGCA CTTGATGCAA 60         70         80         90 99
  CTGGTGTGAC CCTTACTCCA CAAGGTGCTA TTGTCATCGA CCCCGGCAT 205-238S (SEQ ID NO: 10)
         10         20         30         40         50
  GCTTCATGGC TCTGCACGTT TCAAGGACAA CCGTAACCTC ATTGTTCAAC 60         70         80         90 99
  TTAATGATGG TGGTGAACGT GTGGTGGCTT TGACCGCTG TCTCATTGC 383-416N (SEQ ID NO: 23)
         10         20         30         40         50
  CATACACAAA TTGTGGTTGA TCAGTGCAAT CACCAGCTGC ATAGATGTGT 60         70         80         90 99
  TCCACAGAGG TACGCATACC TGGATCAATC ACAATAGCAC CTTGTGGAG
```

TABLE 1-continued

OLIGONUCLEOTIDE SEQUENCES

```
410-437S (SEQ ID NO: 24)
         10         20         30         40         50
ACCACAATTT GTGTATGTTG CTGCTGCTGC TGGTACCCGT GCTGCTATCA 60         70         80         90         99
ACATGACTGG TGGTGATGCT GCCCTCAACC TCACCGCGAT GCCGGCCGT 178-211N (SEQ ID NO: 9)
         10         20         30         40         50
GTGCAGAGCC ATGAAGCACA GTGATGGCTG GGTTACCTTC TAGAATACCT 60         70         80         90         99
TCATACTTTG CATGACGAAG TTCATCAACA CGGGCCTGCT GCTGGGCCA 135-162N (SEQ ID NO: 25)
         10         20         30         40         50
CAAATGGAGA TTCACGACGA AGATGAGCAA TGTGAGCAGC ACGAATCATG 60         70         80         90         99
ATCTTGCTTG GCACACAACC AACATTAACA CAGGTGCCGC CGATGGTGC 156-189S (SEQ ID NO: 26)
         10         20         30         40         50
TCGTGAATCT CCATTTGATG GTGGCATTGC TGCAACCACT CCAACCATTC 60         70         80         90         99
AACGTACTGC ACTCCTTGCA CAACAACAAG CACGTGTTGA TGAACTTCG
```

Example 2
DNA Sequence Determination

DNA sequences were determined for plant expressible metal resistance coding sequences to verify that desired mutagenized changes were made via the overlap extension PCR procedures.

Sequence determinations of single-stranded and double-stranded DNAs were carried out by the dideoxynucleotide chain termination procedure [Sanger et al. (1977) *Proc. Natl. Acad. Sci. USA* 74:8073–8077], with a Sequenase kit (United States Biochemical Corp., Cleveland, Ohio) or an automated fluorescence-based system (Applied Biosystems, Foster City, Calif.).

Example 3
Bacterial Assays of Metal Resistance

*E. coli* SK1592 is Gal⁻, Thi⁻, T1$^R$, EndA⁻, hsdR4, sbcB15, Sup, and is highly proficient as a host in transformation.

pDMT10 is a pTZ vector (Pharmacia, Piscataway, N.J.) which carries an insert of all the genes of the mer operon (merT, merC, merP and merA). pDU202 is also a wild-type mer plasmid. pDU202 carries the wild-type mer operon. Both these plasmids confer a mercury resistant phenotype on *E. coli* strains which harbor it. pPB111-47 contains the mer operon within an R100 plasmid, but it contains a Tn5 insertion in the merA gene; it is suitable as a host for recombinant plasmids. The phenotype of *E. coli* strains carrying this plasmid is mercury hypersensitivity. For routine growth, *E. coli* strains are grown on LB media at 37° C. No potentially inhibitory compounds are incorporated into the medium unless otherwise noted.

The minimum HgCl$_2$ concentration to inhibit *E. coli* growth is 5 $\mu$M, and 10$\mu$ HgCl was used for selections. *E. coli* colonies which grew on LB plates containing 5, 10 and 50 $\mu$M HgCl$_2$ were considered to be mercury resistant. Selection of plasmids was performed by the inclusion of 50 $\mu$g/ml kanamycin and/or 100 $\mu$g/ml ampicillin.

Figure 2:
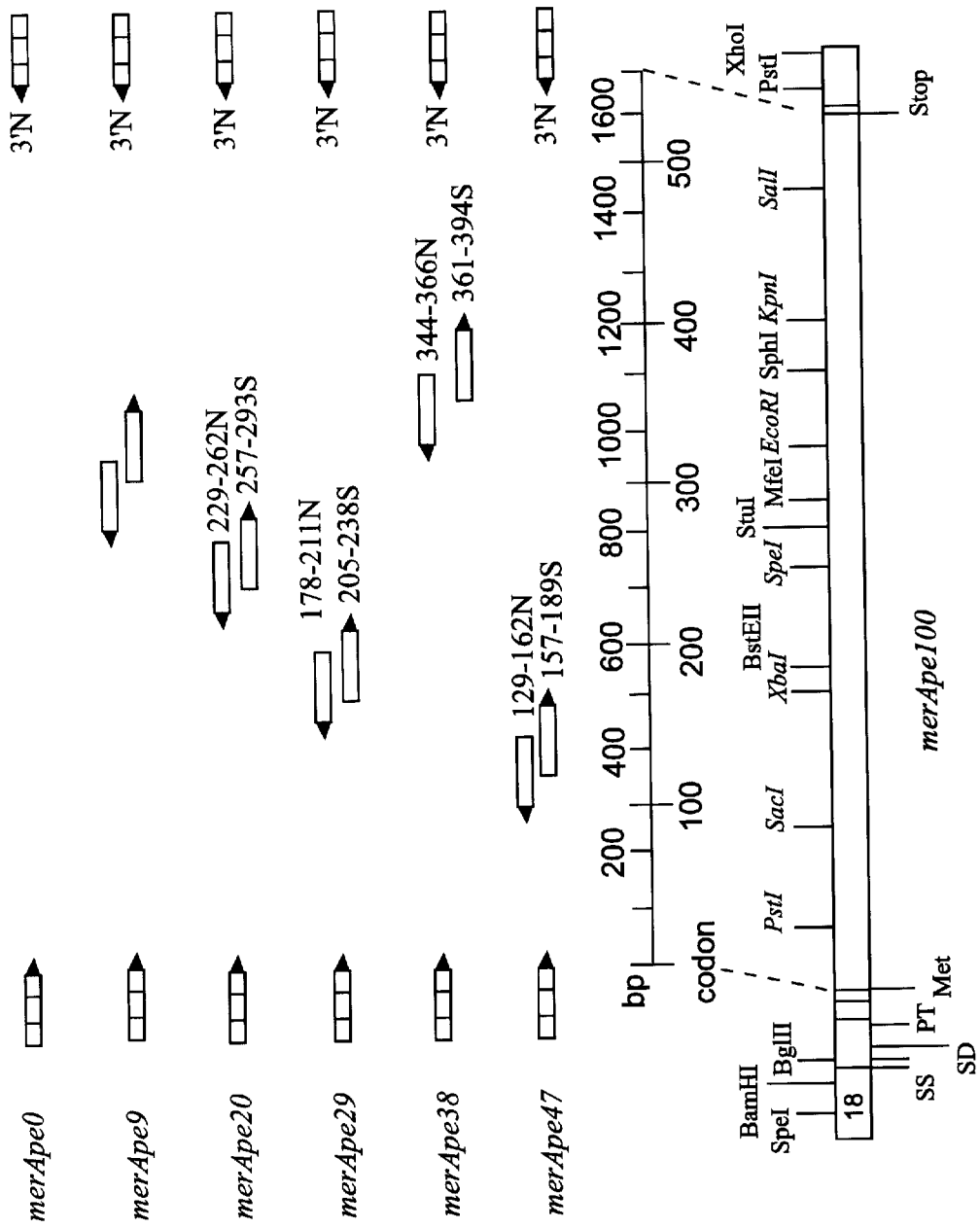
FIG. 2 diagrammatically illustrates strategies for the construction of merA sequences designed to be plant-expressible. The overlap extension PCR technique is used to produce the plant expressible merA derivatives. For example, to make merApe9, two fragments were synthesized by priming OE PCR reactions with merA (see SEQ ID NO:1) and two pairs of primers (5'S and 282/312N, i.e, SEQ ID NO:3 and NO:4; 307-339S and 3'N, SEQ ID NO:5 and NO:6). The two reaction products are purified and joined in a second PCR reaction using 5'S and 3'N (SEQ ID NO:3 and NO:6) as primers. Three more rounds of mutagenesis are carried out, each time starting with the preceding constructs, resulted in merApe38, which has 38% synthetic sequence. Primer sequences are given in Table 2 hereinbelow. After the primer, merApe100 has 100% idealized sequence (for plant expression) and contains additional restriction sites as the result of silent base changes relative to the coding sequence of the naturally occurring merA coding sequence. The merApe100 nucleotide sequence is provided in Table 10, SEQ ID NO:31.

The wild-type merA coding sequence and mutated coding sequences were inserted under the regulatory control of the lac promoter into *E. coli*-compatible plasmids for testing effect on mercury sensitivity. pNS2 contains the merApe9 coding sequence (see SEQ ID NO:15), pNS5 contains the merApe38 coding sequence (see FIG. 2) and pNS100 contains the merApe100 coding sequence (see FIG. 2, SEQ ID NO:31).

Sensitivity assays were carried out using the filter disk technique to determine the phenotypes of various genotypes of *E. coli* strains. Solid medium in these experiments was Tryptone agar for HgCl$_2$, HAuCl$_4$, NiCl$_2$ and CoCl$_2$. HMM medium with glycerol phosphate as the phosphate source [LaRossa et al. (1994) *J. Indus. Microbiol.* in press] was used in some experiments to prevent the precipitation of some metals. HMM contains 40 mM MOPS buffer, pH 7.3, 50 mM KCl, 10 mM NH$_4$Cl, 0.5 mM MGSO$_4$, 0.4% glucose, 1 mM glycerol-2-phosphate and 1 $\mu$M FeCl$_3$. The results are summarized in Table 1.

TABLE 2

Filter Disk Assay for Metal Ion Sensitivity*
<--- plasmid, strain, and Hg++ sensitivity --->

| Metal Salt | 2 ul/ disk [con.] | SK1592 Hg$^s$ | SK1592/ pNS2 Hg$^r$ | SK1592/ pPB111-47 Hg$^{ss}$ | SK1592/ pPB111-47/ pNS2 Hg$^r$ | SK1592/ pPB111-47/ pNS5 Hg$^r$ | DU1040 pDU202 Hg$^r$ |
|---|---|---|---|---|---|---|---|
| HgCl$_2$ | 0.1 M | 25 mm | 20 mm | 30 mm | 14 mm | 14 mm | 15 mm |
| HAuCl$_4$ | 0.2 M | 20 mm | 16 mm | 20 mm | 15.5 mm | | 16 mm |
| NiCl$_2$ | 1.0 M | 17 mm | 17 mm | 16 mm | 13.5 mm | | 14 mm |
| CoCl$_2$ | 1.0 M | 19 mm | 19 mm | 17 mm | 15 mm | | 15 mm |
| **HgCl$_2$ | 0.1 M | 34 mm | 28 mm | | | | |
| **HAuCl$_4$ | 0.2 M | 25 mm | 18 mm | | | | |
| **CuCl$_2$ | 1.0 M | 30 mm | 25 mm | | | | |

*The mer operon is induced to maximum expression by Hg$^{++}$ ion. Experiments using trace amounts of Hg$^{++}$ in the plates (not shown) altered the actual killing zone sizes but does not significantly alter the interpretation of the data presented above. These results have been repeated several times and the zone of inhibition varies by less than 1 mm per experiment. Experiments in the top half of the table used tryptone plates.
**The last three disk assays used HMM media with glycerol phosphate as a phosphate source to prevent the precipitation of some metals.

The results in Table 2 demonstrate that merA (or the mutated sequences thereof) can mediate significant resistance to both mercuric and auric ions. *E. coli* strains which contain merA in combination with the merT transport protein show some resistance to Co and Ni divalent cations.

Example 4
Construction of Plant Expression Constructs

Recombinant DNA methods were performed according to established methods (Sambrook et al. (1989) supra). pNS2 was cut with BamHI just upstream of the merA coding sequence and XhoI in the multilinker downstream of merA. This fragment was inserted into the replacement regions of the binary plant expression vector pVSTI [Malik and Wahab (1993) *J. Plant Biochem. Biotech.* 2:69–70] to produce pPENS2. The merApe9 coding sequence is expressed in plants under the regulatory control of the CaMV 35S promoter and nos polyadenylation signals. Agrobacterium-mediated transformation of *Arabidopsis thaliana* var. RLD root explants essentially as described by Marton (1991) *Plant Cell. Rep.* 10:235–239. Large numbers of independent transgenic shoot resulted, and these shoots were planted in soil, fed topically and allowed to go to seed (T1 seeds).

Example 5
Generation of Transgenic Plants

Agrobacterium-mediated transformation of *Arabidopsis thaliana* var. RLD root explants essentially as described by Marton (1991) *Plant Cell. Rep.* 10:235–239. Large numbers of independent transgenic shoot resulted, and these shoots were planted in soil, fed topically and allowed to go to seed (T1 seeds). The T1 seeds from transgenic plant line NS2-6 germinated and grew on plant growth solidified agar medium [Murashige and Skoog (1964) *Plant. Physiol.* 15:485] containing 60 μM HgCl$_2$. Almost all transgenic lines grew on 20–100 μM HgCl$_2$. 100 μm HgCl$_2$ corresponds to 40 ppm. Untransformed RLD control seeds exposed to 20 μM or higher concentrations of HgCl$_2$ either did not germinate or died shortly after germination. Where an organometal coding sequence, such as merB, was introduced into the plant tissue, selection was carried out as described in Example 10 hereinbelow.

Example 6
Metal Resistance of Transgenic Plants

Growth of parental plantlets of Arabidopsis var. RLD, and transgenic plants carrying either the merApe9 plant-expressible gene or a β-glucuronidase plant expressible construct (GUS, as a control) was tested on Murashige and Skoog plant growth medium [Murashige and Skoog (1964) supra] with and without metal ions.

The T1 seeds from transgenic plant line NS2-6 germinated and grew on plant growth solidified agar medium containing 60 μM HgCl$_2$. Almost all transgenic lines containing and expressing merApe9 grew on 20–60 μM HgCl$_2$. Untransformed RLD control seeds and the GUS control transgenic plants exposed to 20 μM or higher concentrations of HgCl$_2$ either did not germinate or died shortly after germination.

The merApe9 transgenic plants grow significantly better than the GUS and untransformed controls on plant growth solidified medium containing 100–500 μM AuHCl$_4$. Root growth Physiol. is most dramatically affected on the medium containing gold ions.

Plants genetically engineered to contain and express a plant-expressible merB coding sequence are resistant to organometal compounds including methyl mercury, phenylmethyl mercury and p-chloromercuribenzoate. Where reduction of mercuric ions produced in the organomercury lyase reaction is desired, the plants also contain a plant-expressible metal ion reductase, desirably a plant-expressible merA coding sequence as specifically described herein.

Example 7
Mercuric Ion Reduction in Transgenic Plants

Transgenic seedlings containing the plant-expressible metal resistance coding sequence (merApe9) catalyzed significant reduction of divalent mercury to elemental mercury relative to the chemical reduction of mercuric ions observed with control seedlings of the parental RLD lineage.

About 10 seedlings (10 days old, 0.05 g total wet weight) were incubated in 2 ml assay medium (25 mM sodium phosphate pH 7.0, 5 μM HgCl$_2$) in glass bubbler tubes designed with an outlet vent for collection of sparged gas. The amount of elemental mercury (Hg$^0$) produced was assayed by bubbling air through the sample (for 12 sec)

beginning at 8 sec after placing the seedlings into the assay medium. Samples were then re-assayed every min over the next 10 min. so that the rate of mercury evolution could be determined. The volatilized Hg° for each sampling was measured by passing each sample over the gold foil membrane resister on a Jerome 431 mercury vapor analyzer (Arizona Instrument Corp., Tempe, Ariz.). The instrument was repeatedly standardized with known quantities of Hg (1–50 ng), reduced form $HgCl_2$ with excess $SnCl_2$. The amount of Hg° evolved was normalized to the amount of tissue used in each assay reaction. It was found to be necessary to bake all glassware for the assays at 180° C. for 6 hrs before use.

Example 8
Strains, Plasmids, and Materials for Testing MerB

E. coli strain SK1592 (F-, gal-, thi-, sup-, tonA-, hsdR4, endA-, SbcB15) is a spontaneous T1 phage-resistant derivative of SK1590 [Kushner, S. R. (1978) *Genetic Engineering*, Boyer and Nicosia, eds., North Holland, Elsevier/ Biomedical Press, pp. 17–23]. The pBluescriptSKII+ (pBSSKII) vector plasmid was obtained from Stratagene Inc., La Jolla Calif. All metal ion sensitivity filter disk assays were performed in the presence of ampicillin to maintain the pBSSKII plasmids and kanamycin or chloramphenicol, to retain the narrow spectrum resistance mer operon plasmid, pDU202. Approximately $2 \times 10^8$ cells were plated in Luria top agar onto Luria plates. 2 to 4 ul of a freshly prepared organic mercury stock solution, at the concentration indicated in Table 2, were aliquoted onto a 6 mm diameter filter disk (Whatmann 3M) and the filter disk was positioned on the freshly solidified top agar. The diameter of the zone of inhibition was measured after 16–20 hr growth at 37° C. and the data reported are the average results of several replicates. The zone sizes among individual experiments varied by less than 0.5–1 mm for any of the data reported. As sources of organic mercury, the acetate salt of phenyl mercury (PMA) and the chloride salt of methyl mercury ($MeHg^+$; Alpha Aesar, Ward Hill, Mass.) were prepared as separate 0.1 M stock solutions in DMSO and ethanol, respectively. These compounds are extremely toxic and should be handled with great caution as directed by the manufacturers.

TABLE 3

Filter disk assay for metal and organometal ion sensitivity in E. coli*.

| Strain | SK1592 | SK1592 |
|---|---|---|
| merA plasmid | pDU202-merA+ | pDU202-merA+ |
| test plasmid | pBSSKII-merB− | pmerBpe-merB+ |
| phenotype | $Hg^r$, $MeHg^s$ | $Hg^r$, $MeHg^r$ |
| Metal Salt 2 | zone size | zone size |
| 2 μl/disk | | |
| $HgCl_2$ 0.1 M | 18 mm | 20 mm |
| PMA 0.1 m | 23 mm | 9 mm |
| NaPCMB .01 M | 13 mm | 10 mm |

E. coli strain SK1592 containing the various mer gene and control plasmids were assayed for Hg(II) and organomercury resistance.

* Each 6 mm diameter disk contained 2 μl of freshly prepared metal salt stock solution at the concentration indicated. The genotype of each strain (i.e., for merA and merB) and phenotype on mercury (Hg, PMA and PCMB sensitivity or resistance) is indicated below the strain and plasmid designations. These results were repeated several times and the zones of growth inhibition measured seldom varied more than 0.5 mm from those shown above.

Example 9
Plant Expressible merB Coding Sequence

A plant-expressible merB coding sequence is engineered using a naturally occurring merB gene and adapting it by overlap extension PCR in an analogous manner with the MerB5'S and MerB3'A primers (see hereinbelow). as used for the adaptation of merA as described hereinabove.

One of the best characterized merB genes available is found on the broad-spectrum resistance plasmid R831b [Begley et al., 1986b, supra; Begley et al., 1986a, supra; Barkay et al., 1992, supra]. This merB gene was subcloned from the R831b mer operon on a 1.5 kb EcoRI fragment into pBR322 to make pCT12. The original merB sequence (GenBank accession #EC-U77087) has a reasonable GC nucleotide composition (~57%), rarely used plant codons are few, and it encodes a small protein of about 213 amino acids [Ogawa et al. (1984) *Gene* 32:311–320; Tolle and Summers (1985) *Abstr. Annu. Meet. Am. Soc. Microbiol.* 85:120].

Flanking primers (FIG. 4) were used to amplify the merB gene with the polymerase chain reaction (PCR). The 5' flanking sequence primer, merB5'S, had the 57 nt sequence 5'GCGGTCGGAT CCGAATTCGT CGACTAAGGA GGAGCCACAA TGAAGCTCGC CCCATAT3' (SEQ ID NO:17), and contained BamHI, EcoRI, and BglII cloning sites; a TAA stop codon to end the translation of a β-gal fusion protein in *E. coli*; a AGAAGG bacterial translation signal [Stormo et al. (1982) *Nucl. Acids Res.* 10:2971–1996] to aid in merA expression in *E. coli*; an AGCCACA consensus sequence for plant translation [Heidecker and Menning (1986) *Ann. Plant Physiol.* 47:45–462]; an ATG start codon; and the first 18 nt of the merB coding sequence to prime the forward PCR reaction. The 3' flanking sequence primer, merB3'N, had the 43 nt sequence, 5'CGTATCGGAT CCGAATTCAA GCTTATCACG GTGTCCTAGA TGA-3' (SEQ ID NO:18), containing HindIII, EcoRI, and BamHI cloning sites and anticodons to the merB, the last 7 codons including the stop codon to prime the reverse PCR reaction. The PCR amplification contained amplification buffer (Promega, Madison, Wis.) 1.5 units of Taq polymerase (Promega), and was carried out for 35 cycles (95° C. 1 min, 42° C. 1 min, and 72° C. 1 min). The mutagenized sequence was cleaved in the flanking BamHI and HindIII sites; ligated into the BamHI/HindIII replacement region in the multilinker of plasmid pBluescriptSKII(−) (Stratagene) to make pmerBpe; and transformed into an mercuric ion resistant strain of *E. coli* and selected for ampicillin resistance. Most of the pmerBpe containing strains showed resistance to the acetate salt of phenyl mercury (PMA) when tested in disk sensitivity assays. DNA sequencing confirmed the expected merB sequence and flanking sequences in pmerBpe and its encoded protein sequence.

Resistance to organomercurial compounds is confirmed in an *E. coli* host which also contains merA, for example on plasmid pDU202 [Foster, T. J. (1983) *Microbiol. Rev.* 47:361–409]. For testing the organomercurial resistance phenotype, PCMB is applied onto a sterile filter paper disk (5 μl of 10 mM solution) on the surface of soft agar seeded with the *E. coli* strain carrying the gene to be tested.

Where resistance is desired to metal ions as well as organomercurials the transgenic plant also contains a plant-expressible merA coding sequence as taught hereinabove.

Example 10
Construction of merB Transgenic Plants

*Agrobacterium tumefaciens*-mediated transformation of embryos (Marton and Browse, 1991) induced in root explants or vacuum infiltration of the inflorescence

[Bechtold et al. (1993) *C.R. Acad. Sci. Paris, Life Sciences* 316:1194–1199] were used to introduce the merBpe gene into *Arabidopsis thaliana* (RLD var.). The two methods produce transgenic shoots and seeds, respectively. Both methods resulted in a large number of independent transgenic lines, which were examined further.

Mono methyl mercury (MeHg+) is the major form of environmental mercury that is biomagnified up the food chain. Although the MerB enzyme has a broad substrate range for organic mercury compounds, the enzyme is significantly less efficient at catalyzing the breakdown of MeHg+ than of PMA. Therefore, we assayed the resistance of plants to this environmentally important compound. Second generation (T1) seeds, seedlings, and plants from several independent transgenic Arabidopsis plant lines expressing merBpe were resistant to 1–3 mM methyl mercury chloride incorporated into the growth medium. The results were different from those on PMA in that 50–75% of the control and experimental lines germinated at these concentrations of methyl mercury chloride and all grew similarly for about one week. After 10 days the RLD controls and merApe9 expressing plants turned yellow and after two weeks they turned white and died. At these concentrations the merBpe expressing plants grew at rates comparable to unchallenged controls and continued to grow normally until they set flowers and seed. In addition, the transgenic merBpe-expressing lines showed vigorous root growth with 1–3 μM methyl mercury chloride in the agar medium.

Example 11
Confirming the Presence of the merB Gene and Protein in Transgenic Plants The presence of the MerBpe DNA coding sequence and expression of the MerB protein in transgenic plants were examined.

Primers internal to and specific for the merBpe gene were used to amplify (by PCR) a 400 bp fragment from the merBpe gene in T1 and T2 generation plants. Template DNA was prepared from leaves and stems. Control plant DNA yielded no merBpe amplification product, while merBpe-expressing plants resistant to PMA all showed the presence of the characteristic 400 bp amplification product. The expression of MerB protein was confirmed in Western blot assays performed on whole plant protein extracts. The total protein extracts from MerBpe-producing plants and control plants were resolved in different lanes on a sodium dodecyl sulfate-polyacrylamide electrophoretic gel, transferred to a nylon membrane, and reacted with MerB-specific monoclonal antibodies. PMA-resistant plants, which contained the merBpe gene, also contained easily detectable levels of the 21 kD MerB protein on these Western blots. No protein was detected in this molecular weight position in the lanes containing extracts from control plants.

Example 12
PCR mutagenesis Strategy

The strategy for generating plant-expressible merA coding sequences other than merApe9 is presented in FIG. 2, together with the sequences of the primers to be used in PCR as described hereinabove and with reference to FIG. 1 and its description. Mutagenic primer sequences are given in Table 2 and in SEQ ID NOs:3–14. The merA coding sequence of Tn21 is provided in SEQ ID NO:1, from nucleotide 14 to nucleotide 1708, and is taken from Barrineau et al. (1984) *J. Mol. Appl. Genet.* 2:601–619. Sequences of merApe9, merApe20, merApe29, merApe38, merApe47 and merApe100 are disclosed herein. See SEQ ID NOs:15, 27, 29, 13, 19, and 31.

Example 13
Generation of Random Mutations in merA

Where it is desired to express an altered merA gene in plants, the starting material for the generation of random mutations in the merA coding sequence, the starting material is purified DNA comprising one of merApe9, merApe20, merApe29, merApe38, merApe47 and merApe100, or other plant-expressible merA coding sequences. Mutagenic PCR is carried out as essentially as described by Muhlrad et al. (1992) *Yeast* 8:79–82. Template DNA (e.g., pNS2) is linearized a restriction enzyme (which cuts one time in the plasmid, outside the merA coding sequence) and diluted top 10 ng/ml. Concentrated reaction buffer is added to give final concentrations of 100 mM Tris-HCl, pH 8.3, 500 mM KCl, 0.1% (w/v) gelatin, and nucleotide triphosphates are added to a final concentration 1 mM each of dGTP, dCTP and dTTP and 200 μM dATP, primers are added, and 2.5 units of AmpliTAQ DNA polymerase (Cetus) is added to start the reaction. Each reaction is supplemented with $MgCl_2$ at a concentration of from 1.5 to 6 mM and $MnCl_2$ is added for a final concentration of 0.05 to 0.65 mM. Reactions were carried out in a volume of 25 μl each after overlayering with 100 μl mineral oil.

Untreated plasmid DNA (100 ng) is then mixed with the mutagenic PCR product (20μ) and transformed into competent *E. coli* cells, with selection for drug resistance carried by the vector portion of the plasmid carrying the coding sequence which was used as template in the mutagenic PCR reaction. In the cells, the PCR products (containing mutations relative to the starting template) recombine via homologous sequences into the plasmid. Then the potential mutants are screened for novel phenotypes useful in the practice of the present invention.

Transformants are then tested for the maintenance of resistance to mercuric ion as described above, and they are tested for cross-resistance to other metal ions.

TABLE 4

(SEQ ID NO:1 and SEQ ID NO:2) MerA from Tn21

```
AAGGAACGAT GGT ATG AGC ACT CTC AAA ATC ACC GGC ATG ACT TGC GAC
            Met Ser Thr Leu Lys Ile Thr Gly Met Thr Cys Asp
            1               5                   10

TCG TGC GCA GTG CAT GTC AAG GAC GCC CTG GAG AAA GTG CCC GGC GTG
Ser Cys Ala Val His Val Lys Asp Ala Leu Glu Lys Val Pro Gly Val
            15                  20                  25
```

TABLE 4-continued (SEQ ID NO:1 and SEQ ID NO:2) MerA from Tn21

| CAA | TCA | GCG | GAT | GTC | TCC | TAC | GCC | AAG | GGC | AGC | GCC | AAG | CTC | GCC | ATT |
|---|---|---|---|---|---|---|---|---|---|---|---|---|---|---|---|
| Gln | Ser | Ala | Asp | Val | Ser | Tyr | Ala | Lys | Gly | Ser | Ala | Lys | Leu | Ala | Ile |
| | 30 | | | | 35 | | | | | 40 | | | | | |

| GAG | GTC | GGC | ACG | TCA | CCC | GAC | GCG | CTG | ACG | GCC | GCT | GTA | GCT | GGA | CTC |
|---|---|---|---|---|---|---|---|---|---|---|---|---|---|---|---|
| Glu | Val | Gly | Thr | Ser | Pro | Asp | Ala | Leu | Thr | Ala | Ala | Val | Ala | Gly | Leu |
| 45 | | | | | 50 | | | | | 55 | | | | | 60 |

| GGT | TAT | CGG | GCC | ACG | CTG | GCC | GAT | GCC | CCC | TCA | GTT | TCG | ACG | CCG | GGC |
|---|---|---|---|---|---|---|---|---|---|---|---|---|---|---|---|
| Gly | Tyr | Arg | Ala | Thr | Leu | Ala | Asp | Ala | Pro | Ser | Val | Ser | Thr | Pro | Gly |
| | | | | 65 | | | | | 70 | | | | | 75 | |

| GGA | TTG | CTC | GAC | AAG | ATG | CGC | GAT | CTG | CTG | GGC | AGA | AAC | GAC | AAG | ACG |
|---|---|---|---|---|---|---|---|---|---|---|---|---|---|---|---|
| Gly | Leu | Leu | Asp | Lys | Met | Arg | Asp | Leu | Leu | Gly | Arg | Asn | Asp | Lys | Thr |
| | | | 80 | | | | | 85 | | | | | 90 | | |

| GGT | AGC | AGC | GGC | GCA | TTG | CAT | ATC | GCC | GTC | ATC | GGC | AGC | GGC | GGG | GCC |
|---|---|---|---|---|---|---|---|---|---|---|---|---|---|---|---|
| Gly | Ser | Ser | Gly | Ala | Leu | His | Ile | Ala | Val | Ile | Gly | Ser | Gly | Gly | Ala |
| | | 95 | | | | | 100 | | | | | 105 | | | |

| GCG | ATG | GCA | GCG | GCG | CTG | AAG | GCC | GTC | GAG | CAA | GGC | GCA | CCT | GTC | ACG |
|---|---|---|---|---|---|---|---|---|---|---|---|---|---|---|---|
| Ala | Met | Ala | Ala | Ala | Leu | Lys | Ala | Val | Glu | Gln | Gly | Ala | Pro | Val | Thr |
| | 110 | | | | | 115 | | | | | 120 | | | | |

| CTG | ATC | GAG | CGC | GGC | ACC | ATC | GGC | GGC | ACC | TGC | GTC | AAT | GTC | GGT | TGT |
|---|---|---|---|---|---|---|---|---|---|---|---|---|---|---|---|
| Leu | Ile | Glu | Arg | Gly | Thr | Ile | Gly | Gly | Thr | Cys | Val | Asn | Val | Gly | Cys |
| 125 | | | | | 130 | | | | | 135 | | | | | 140 |

| GTG | CCG | TCC | AAG | ATC | ATG | ATC | CGC | GCC | GCC | CAT | ATC | GCC | CAT | CTG | CGC |
|---|---|---|---|---|---|---|---|---|---|---|---|---|---|---|---|
| Val | Pro | Ser | Lys | Ile | Met | Ile | Arg | Ala | Ala | His | Ile | Ala | His | Leu | Arg |
| | | | | 145 | | | | | 150 | | | | | 155 | |

| CGG | GAA | AGC | CCG | TTC | GAT | GGC | GGC | ATC | GCC | GCT | ACC | ACG | CCG | ACC | ATC |
|---|---|---|---|---|---|---|---|---|---|---|---|---|---|---|---|
| Arg | Glu | Ser | Pro | Phe | Asp | Gly | Gly | Ile | Ala | Ala | Thr | Thr | Pro | Thr | Ile |
| | | | 160 | | | | | 165 | | | | | 170 | | |

| CAG | CGC | ACG | GCG | CTG | CTG | GCC | CAG | CAG | CAG | GCC | CGC | GTC | GAT | GAA | CTG |
|---|---|---|---|---|---|---|---|---|---|---|---|---|---|---|---|
| Gln | Arg | Thr | Ala | Leu | Leu | Ala | Gln | Gln | Gln | Ala | Arg | Val | Asp | Glu | Leu |
| | | 175 | | | | | 180 | | | | | 185 | | | |

| CGC | CAC | GCC | AAG | TAC | GAA | GGC | ATC | TTG | GAG | GGC | AAT | CCG | GCG | ATC | ACT |
|---|---|---|---|---|---|---|---|---|---|---|---|---|---|---|---|
| Arg | His | Ala | Lys | Tyr | Glu | Gly | Ile | Leu | Glu | Gly | Asn | Pro | Ala | Ile | Thr |
| | 190 | | | | | 195 | | | | | 200 | | | | |

| GTG | CTG | CAC | GGC | TCC | GCC | CGC | TTT | AAG | GAC | AAT | CGC | AAC | CTG | ATC | GTG |
|---|---|---|---|---|---|---|---|---|---|---|---|---|---|---|---|
| Val | Leu | His | Gly | Ser | Ala | Arg | Phe | Lys | Asp | Asn | Arg | Asn | Leu | Ile | Val |
| 205 | | | | | 210 | | | | | 215 | | | | | 220 |

| CAA | CTC | AAC | GAC | GGC | GGC | GAG | CGC | GTG | GTG | GCA | TTC | GAC | CGC | TGC | CTG |
|---|---|---|---|---|---|---|---|---|---|---|---|---|---|---|---|
| Gln | Lsu | Asn | Asp | Gly | Gly | Glu | Arg | Val | Val | Ala | Phe | Asp | Arg | Cys | Leu |
| | | | | 225 | | | | | 230 | | | | | 235 | |

| ATC | GCC | ACC | GGC | GCG | AGC | CCG | GCC | GTG | CCG | CCG | ATT | CCC | GGC | CTG | AAA |
|---|---|---|---|---|---|---|---|---|---|---|---|---|---|---|---|
| Ile | Ala | Thr | Gly | Ala | Ser | Pro | Ala | Val | Pro | Pro | Ile | Pro | Gly | Leu | Lys |
| | | | 240 | | | | | 245 | | | | | 250 | | |

| GAC | ACT | CCG | TAC | TGG | ACT | TCC | ACT | GAA | GCG | CTG | GTC | AGC | GAG | ACG | ATT |
|---|---|---|---|---|---|---|---|---|---|---|---|---|---|---|---|
| Asp | Thr | Pro | Tyr | Trp | Thr | Ser | Thr | Glu | Ala | Leu | Val | Ser | Glu | Thr | Ile |
| | | 255 | | | | | 260 | | | | | 265 | | | |

| CCT | AAG | CGC | CTG | GCC | GTG | ATT | GGC | TCA | TCA | GTG | CTG | GCG | CTG | GAG | CTG |
|---|---|---|---|---|---|---|---|---|---|---|---|---|---|---|---|
| Pro | Lys | Arg | Leu | Ala | Val | Ile | Gly | Ser | Ser | Val | Leu | Ala | Leu | Glu | Leu |
| | 270 | | | | | 275 | | | | | 280 | | | | |

| GCG | CAG | GCG | TTC | GCC | CGA | CTC | GGA | GCG | AAG | GTG | ACG | ATC | CTG | GCT | CGC |
|---|---|---|---|---|---|---|---|---|---|---|---|---|---|---|---|
| Ala | Gln | Ala | Phe | Ala | Arg | Leu | Gly | Ala | Lys | Val | Thr | Ile | Leu | Ala | Arg |
| 285 | | | | 290 | | | | | 295 | | | | | | 300 |

| AGC | ACG | CTG | TTC | TTC | CGC | GAA | GAC | CCA | GCT | ATA | GGC | GAA | GCT | GTC | ACG |
|---|---|---|---|---|---|---|---|---|---|---|---|---|---|---|---|
| Ser | Thr | Leu | Phe | Phe | Arg | Glu | Asp | Pro | Ala | Ile | Gly | Glu | Ala | Val | Thr |
| | | | | 305 | | | | | 310 | | | | | 315 | |

| GCC | GCA | TTC | CGG | ATG | GAG | GGC | ATC | GAG | GTG | AGG | GAA | CAC | ACC | CAG | GCC |
|---|---|---|---|---|---|---|---|---|---|---|---|---|---|---|---|
| Ala | Ala | Phe | Arg | Met | Glu | Gly | Ile | Glu | Val | Arg | Glu | His | Thr | Gln | Ala |
| | | | 320 | | | | | 325 | | | | | 330 | | |

TABLE 4-continued

(SEQ ID NO:1 and SEQ ID NO:2) MerA from Tn21

```
AGC CAG GTC GCG TAT ATC AAT GGT GAA GGG GAC GGC GAA TTC GTG CTC
Ser Gln Val Ala Tyr Ile Asn Gly Glu Gly Asp Gly Glu Phe Val Leu
        335             340             345

ACC ACG GCG CAC GGC GAA CTG CGC GCC GAC AAG CTG CTG GTC GCC ACC
Thr Thr Ala His Gly Glu Leu Arg Ala Asp Lys Leu Leu Val Ala Thr
    350             355             360

GGC CGC GCG CCC AAC ACA CGC AAG CTG GCA CTG GAT GCG ACG GGC GTC
Gly Arg Ala Pro Asn Thr Arg Lys Leu Ala Leu Asp Ala Thr Gly Val
365             370             375             380

ACG CTC ACC CCC CAA GGC GCT ATC GTC ATC GAC CCC GGC ATG CGT ACA
Thr Leu Thr Pro Gln Gly Ala Ile Val Ile Asp Pro Gly Met Arg Thr
            385             390             395

AGC GTG GAA CAC ATC TAC GCC GCA GGC GAC TGC ACC GAC CAG CCG CAG
Ser Val Glu His Ile Tyr Ala Ala Gly Asp Cys Thr Asp Gln Pro Gln
        400             405             410

TTC GTC TAT GTG GCG GCA GCG GCC GGC ACT CGC GCC GCG ATC AAC ATG
Phe Val Tyr Val Ala Ala Ala Gly Thr Arg Ala Ala Ile Asn Met
        415             420             425

ACC GGC GGT GAC GCC GCC CTG AAC CTG ACC GCG ATG CCG GCC GTG GTG
Thr Gly Gly Asp Ala Ala Leu Asn Leu Thr Ala Met Pro Ala Val Val
    430             435             440

TTC ACC GAC CCG CAA GTG GCG ACC GTA GGC TAC AGC GAG GCG GAA GCG
Phe Thr Asp Pro Gln Val Ala Thr Val Gly Tyr Ser Glu Ala Glu Ala
445             450             455             460

CAC CAT GAC GGC ATC AAA ACT GAT AGT CGC ACG CTA ACG CTG GAC AAC
His His Asp Gly Ile Lys Thr Asp Ser Arg Thr Leu Thr Leu Asp Asn
            465             470             475

GTG CCG CGC GCG CTC GCC AAC TTC GAC ACG CGC GGC TTC ATC AAA CTG
Val Pro Arg Ala Leu Ala Asn Peh Asp Thr Arg Gly Phe Ile Lys Leu
        480             485             490

GTG GTT GAA GAA GGG AGC GGA CGA CTG ATC GGC GTC CAG GCA GTG GCC
Val Val Glu Glu Gly Ser Gly Arg Leu Ile Gly Val Gln Ala Val Ala
        495             500             505

CCG GAA GCG GGC GAA CTG ATC CAG ACG GCC GCA CTG GCG ATT CGC AAC
Pro Glu Ala Gly Glu Leu Ile Gln Thr Ala Ala Leu Ala Ile Arg Asn
    510             515             520

CGG ATG ACG GTG CAG GAA CTG GCC GAC CAG TTG TTC CCC TAC CTG ACG
Arg Met Thr Val Gln Glu Leu Ala Asp Gln Leu Phe Pro Tyr Leu Thr
525             530             535             540

ATG GTC GAA GGG TTG AAG CTC GCG GCG CAG ACC TTC AAC AAG GAT GTG
Met Val Glu Gly Leu Lys Leu Ala Ala Gln Thr Phe Asn Lys Asp Val
            545             550             555

AAG CAG CTT TCC TGC TGC GCC GGG TGA GGACAAGGAG GTGTGCGATG
Lys Gln Leu Ser Cys Cys Ala Gly
            560                 565
```

TABLE 5

MerApe 9 DNA and Amino Acid Sequences (SEQ ID NOs:15 and 16)

```
CTAGAACTAG TGGATCCCTA GATCTAAGAA GGAACCACA ATG AGC ACT CTC AAA
                                            Met Ser Thr Leu Lys
                                            1                 5

ATC ACC GGC ATG ACT TGC GAC TCG TGC GCA GTG CAT GTC AAG GAC GCC
Ile Thr Gly Met Thr Cys Asp Ser Cys Ala Val His Val Lys Asp Ala
            10              15              20
```

TABLE 5-continued

MerApe 9 DNA and Amino Acid Sequences (SEQ ID NOs:15 and 16)

```
CTG GAG AAA GTG CCC GGC GTG CAA TCA GCG GAT GTC TCC TAC GCC AAG
Leu Glu Lys Val Pro Gly Val Gln Ser Ala Asp Val Ser Tyr Ala Lys
            25                  30                  35

GGC AGC GCC AAG CTC GCC ATT GAG GTC GGC ACG TCA CCC GAC GCG CTG
Gly Ser Ala Lys Leu Ala Ile Glu Val Gly Thr Ser Pro Asp Ala Leu
            40                  45                  50

ACG GCC GCT GTA GCT GGA CTC GGT TAT CGG GCC ACG CTG GCC GAT GCC
Thr Ala Ala Val Ala Gly Leu Gly Tyr Arg Ala Thr Leu Ala Asp Ala
        55                  60                  65

CCC TCA GTT TCG ACG CCG GGC GGA TTG CTC GAC AAG ATG CGC GAT CTG
Pro Ser Val Ser Thr Pro Gly Gly Leu Leu Asp Lys Met Arg Asp Leu
70                  75                  80                  85

CTG GGC AGA AAC GAC AAG ACG GGT AGC AGC GGC GCA TTG CAT ATG GCC
Leu Gly Arg Asn Asp Lys Thr Gly Ser Ser Gly Ala Leu His Ile Ala
            90                  95                  100

GTC ATC GGC AGC GGC GGG GCC GCG ATG GCA GCG GCG CTG AAG GCC GTC
Val Ile Gly Ser Gly Gly Ala Ala Met Ala Ala Ala Leu Lys Ala Val
            105                 110                 115

GAG CAA GGC GCA CCT GTC ACG CTG ATC GAG CGC GGC ACC ATC GGC GGC
Glu Gln Gly Ala Pro Val Thr Leu Ile Glu Arg Gly Thr Ile Gly Gly
            120                 125                 130

ACC TGC GTC AAT GTC GGT TGT GTG CCG TCC AAG ATC ATG ATC CGC GCC
Thr Cys Val Asn Val Gly Cys Val Pro Ser Lys Ile Met Ile Arg Ala
        135                 140                 145

GCC CAT ATC GCC CAT CTG CGC CGG GAA AGC CCG TTC GAT GGC GGC ATC
Ala His Ile Ala His Leu Arg Arg Glu Ser Pro Phe Asp Gly Gly Ile
150                 155                 160                 165

GCC GCT ACC ACG CCG ACC ATC CAG CGC ACG GCG CTG CTG GCC CAG CAG
Ala Ala Thr Thr Pro Thr Ile Gln Arg Thr Ala Leu Leu Ala Gln Gln
            170                 175                 180

CAG GCC CGC GTC GAT GAA CTG CGC CAC GCC AAG TAC GAA GGC ATC TTG
Gln Ala Arg Val Asp Glu Leu Arg His Ala Lys Tyr Glu Gly Ile Leu
            185                 190                 195

GAG GGC AAT CCG GCG ATC ACT GTG CTG CAC GGC TCC GCC CGC TTT AAG
Glu Gly Asn Pro Ala Ile Thr Val Leu His Gly Ser Ala Arg Phe Lys
            200                 205                 210

GAC AAT CGC AAC CTG ATC GTG CAA CTC AAC GAC GGC GGC GAG CGC GTG
Asp Asn Arg Asn Leu Ile Val Gln Leu Asn Asp Gly Gly Glu Arg Val
        215                 220                 225

GTG GCA TTC GAC CGC TGC CTG ATC GCC ACC GGC GCG AGC CCG GCC GTG
Val Ala Phe Asp Arg Cys Leu Ile Ala Thr Gly Ala Ser Pro Ala Val
230                 235                 240                 245

CCG CCG ATT CCC GGC CTG AAA GAC ACT CCG TAC TGG ACT TCC ACT GAA
Pro Pro Ile Pro Gly Leu Lys Asp Thr Pro Tyr Trp Thr Ser Thr Glu
            250                 255                 260

GCG CTG GTC AGC GAG ACG ATT CCT AAG CGC CTG GCC GTG ATT GGC TCA
Ala Leu Val Ser Glu Thr Ile Pro Lys Arg Leu Ala Val Ile Gly Ser
            265                 270                 275

TCA GTG CTG GCG CTT GAA CTT GCC CAG GCC TTT GCA CGT CTT GGT GCT
Ser Val Leu Ala Leu Glu Leu Ala Gln Ala Phe Ala Arg Leu Gly Ala
            280                 285                 290

AAA GTG ACC ATT CTT GCA CGC TCC ACT CTC TTC TTT CGT GAA GAC CCA
Lys Val Thr Ile Leu Ala Arg Ser Thr Leu Phe Phe Arg Glu Asp Pro
            295                 300                 305

GCT ATA GGT GAA GCT GTT ACT GCT GCA TTT CGC ATG GAA GGC ATT GAA
Ala Ile Gly Glu Ala Val Thr Ala Ala Phe Arg Met Glu Gly Ile Glu
310                 315                 320                 325
```

TABLE 5-continued

MerApe 9 DNA and Amino Acid Sequences (SEQ ID NOs:15 and 16)

```
GTG CGT GAG CAT ACT CAA GCA AGC CAA GTT GCC TAT ATC AAT GGT GAA
Val Arg Glu His Thr Gln Ala Ser Gln Val Ala Tyr Ile Asn Gly Glu
            330             335             340

GGG GAC GGC GAA TTC GTG CTC ACC ACG GCG CAC GGC GAA CTG CGC GCC
Gly Asp Gly Glu Phe Val Leu Thr Thr Ala His Gly Glu Leu Arg Ala
            345             350             355

GAC AAG CTG CTG GTC GCC ACC GGC CGC GCG CCC AAC ACA CGC AAG CTG
Asp Lys Leu Leu Val Ala Thr Gly Arg Ala Pro Asn Thr Arg Lys Leu
            360             365             370

GCA CTG GAT GCG ACG GGC GTC ACG CTC ACC CCC CAA GGC GCT ATC GTC
Ala Leu Asp Ala Thr Gly Val Thr Leu Thr Pro Gln Gly Ala Ile Val
            375             380             385

ATC GAC CCC GGC ATG CGT ACA AGC GTG GAA CAC ATC TAC GCC GCA GGC
Ile Asp Pro Gly Met Arg Thr Ser Val Glu His Ile Tyr Ala Ala Gly
390             395             400             405

GAC TGC ACC GAC CAG CCG CAG TTC GTC TAT GTG GCG GCA GCG GCC GGC
Asp Cys Thr Asp Gln Pro Gln Phe Val Tyr Val Ala Ala Ala Ala Gly
            410             415             420

ACT CGC GCC GCG ATC AAC ATG ACC GGC GGT GAC GCC GCC CTG AAC CTG
Thr Arg Ala Ala Ile Asn Met Thr Gly Gly Asp Ala Ala Leu Asn Leu
            425             430             435

ACC GCG ATG CCG GCC GTG GTG TTC ACC GAC CCG CAA GTG GCG ACC GTA
Thr Ala Met Pro Ala Val Val Phe Thr Asp Pro Gln Val Ala Thr Val
            440             445             450

GGC TAC AGC GAG GCG GAA GCG CAC CAT GAC GGC ATC AAA ACT GAT AGT
Gly Tyr Ser Glu Ala Glu Ala His His Asp Gly Ile Lys Thr Asp Ser
            455             460             465

CGC ACG CTA ACG CTG GAC AAC GTG CCG CGC GCG CTC GCC AAC TTC GAC
Arg Thr Leu Thr Leu Asp Asn Val Pro Arg Ala Leu Ala Asn Phe Asp
470             475             480             485

ACG CGC GGC TTC ATC AAA CTG GTG GTT GAA GAA GGG AGC GGA CGA CTG
Thr Arg Gly Phe Ile Lys Leu Val Val Glu Glu Gly Ser Gly Arg Leu
            490             495             500

ATC GGC GTC CAG GCA GTG GCC CCG GAA GCG GGC GAA CTG ATC CAG ACG
Ile Gly Val Gln Ala Val Ala Pro Glu Ala Gly Glu Leu Ile Gln Thr
            505             510             515

GCC GCA CTG GCG ATT CGC AAC CGG ATG ACG GTG CAG GAA CTG GCC GAC
Ala Ala Leu Ala Ile Arg Asn Arg Met Thr Val Gln Glu Leu Ala Asp
            520             525             530

CAG TTG TTC CCC TAC CTG ACG ATG GTC GAA GGG TTG AAG CTC GCG GCG
Gln Leu Phe Pro Tyr Leu Thr Met Val Glu Gly Leu Lys Leu Ala Ala
            535             540             545

CAG ACC TTC AAC AAG GAT GTG AAG CAG CTT TCC TGC TGC GCC GGG TGA
Gln Thr Phe Asn Lys Asp Val Lys Gln Leu Ser Cys Cys Ala Gly *
550             555             560             565

GGCTGCAGGA ATTCGATA
```

TABLE 6

MerApe 20 DNA and Amino Acid Sequences (SEQ ID NOs:27 and 28)

```
CTAGAACTAG TGGATCCCTA GATCTAAGAA GGAACCACA ATG AGC ACT CTC AAA
                                            Met Ser Thr Leu Lys
                                            1                 5

ATC ACC GGC ATG ACT TGC GAC TCG TGC GCA GTG CAT GTC AAG GAC GCC
Ile Thr Gly Met Thr Cys Asp Ser Cys Ala Val His Val Lys Asp Ala
            10              15              20
```

TABLE 6-continued

MerApe 20 DNA and Amino Acid Sequences (SEQ ID NOs:27 and 28)

```
CTG GAG AAA GTG CCC GGC GTG CAA TCA GCG GAT GTC TCC TAC GCC AAG
Leu Glu Lys Val Pro Gly Val Gln Ser Ala Asp Val Ser Tyr Ala Lys
            25              30                  35

GGC AGC GCC AAG CTC GCC ATT GAG GTC GGC ACG TCA CCC GAC GCG CTG
Gly Ser Ala Lys Leu Ala Ile Glu Val Gly Thr Ser Pro Asp Ala Leu
            40              45              50

ACG GCC GCT GTA GCT GGA CTC GGT TAT CGG GCC ACG CTG GCC GAT GCC
Thr Ala Ala Val Ala Gly Leu Gly Tyr Arg Ala Thr Leu Ala Asp Ala
        55              60              65

CCC TCA GTT TCG ACG CCG GGC GGA TTG CTC GAC AAG ATG CGC GAT CTG
Pro Ser Val Ser Thr Pro Gly Gly Leu Leu Asp Lys Met Arg Asp Leu
70              75              80              85

CTG GGC AGA AAC GAC AAG ACG GGT AGC AGC GGC GCA TTG CAT ATC GCC
Leu Gly Arg Asn Asp Lys Thr Gly Ser Ser Gly Ala Leu His Ile Ala
            90              95              100

GTC ATC GGC AGC GGC GGG GCC GCG ATG GCA GCG GCG CTG AAG GCC GTC
Val Ile Gly Ser Gly Gly Ala Ala Met Ala Ala Ala Leu Lys Ala Val
            105             110             115

GAG CAA GGC GCA CCT GTC ACG CTG ATC GAG CGC GGC ACC ATC GGC GGC
Glu Gln Gly Ala Pro Val Thr Leu Ile Glu Arg Gly Thr Ile Gly Gly
        120             125             130

ACC TGC GTC AAT GTC GGT TGT GTG CCG TCC AAG ATC ATG ATC CGC GCC
Thr Cys Val Asn Val Gly Cys Val Pro Ser Lys Ile Met Ile Arg Ala
        135             140             145

GCC CAT ATC GCC CAT CTG CGC CGG GAA AGC CCG TTC GAT GGC GGC ATC
Ala His Ile Ala His Leu Arg Arg Glu Ser Pro Phe Asp Gly Gly Ile
150             155             160             165

GCC GCT ACC ACG CCG ACC ATC CAG CGC ACG GCG CTG CTG GCC CAG CAG
Ala Ala Thr Thr Pro Thr Ile Gln Arg Thr Ala Leu Leu Ala Gln Gln
            170             175             180

CAG GCC CGC GTC GAT GAA CTG CGC CAC GCC AAG TAC GAA GGC ATC TTG
Gln Ala Arg Val Asp Glu Leu Arg His Ala Lys Tyr Glu Gly Ile Leu
            185             190             195

GAG GGC AAT CCG GCG ATC ACT GTG CTG CAC GGC TCC GCC CGC TTT AAG
Glu Gly Asn Pro Ala Ile Thr Val Leu His Gly Ser Ala Arg Phe Lys
            200             205             210

GAC AAT CGC AAC CTG ATC GTG CAA CTC AAC GAC GGC GGC GAG CGC GTG
Asp Asn Arg Asn Leu Ile Val Gln Leu Asn Asp Gly Gly Glu Arg Val
        215             220             225

GTG GCA TTC GAC CGC TGT CTC ATT GCC ACT GGT GCA AGC CCA GCT GTT
Val Ala Phe Asp Arg Cys Leu Ile Ala Thr Gly Ala Ser Pro Ala Val
230             235             240             245

CCA CCA ATT CCT GGT CTC AAG GAC ACT CCT TAC TGG ACT TCC ACT GAA
Pro Pro Ile Pro Gly Leu Lys Asp Thr Pro Tyr Trp Thr Ser Thr Glu
            250             255             260

GCA CTA GTG TCT GAG ACC ATT CCA AAG CGT CTT GCA GTC ATT GGC TCC
Ala Leu Val Ser Glu Thr Ile Pro Lys Arg Leu Ala Val Ile Gly Ser
            265             270             275

TCT GTG GTG GCT CTT GAA CTT GCC CAG GCC TTT GCA CGT CTT GGT GCT
Ser Val Val Ala Leu Glu Leu Ala Gln Ala Phe Ala Arg Leu Gly Ala
            280             285             290

AAA GTG ACC ATT CTT GCA CGC TCC ACT CTC TTC TTT CGT GAA GAC CCA
Lys Val Thr Ile Leu Ala Arg Ser Thr Leu Phe Phe Arg Glu Asp Pro
        295             300             305

GCT ATA GGT GAA GCT GTT ACT GCT GCA TTT CGC ATG GAA GGC ATT GAA
Ala Ile Gly Glu Ala Val Thr Ala Ala Phe Arg Met Glu Gly Ile Glu
310             315             320             325
```

TABLE 6-continued

MerApe 20 DNA and Amino Acid Sequences (SEQ ID NOs:27 and 28)

```
GTG CGT GAG CAT ACT CAA GCA AGC CAA GTT GCC TAT ATC AAT GGT GAA
Val Arg Glu His Thr Gln Ala Ser Gln Val Ala Tyr Ile Asn Gly Glu
            330                 335                 340

GGG GAC GGC GAA TTC GTG CTC ACC ACG GCG CAC GGC GAA CTG CGC GCC
Gly Asp Gly Glu Phe Val Leu Thr Thr Ala His Gly Glu Leu Arg Ala
            345                 350                 355

GAC AAG CTG CTG GTC GCC ACC GGC CGC GCG CCC AAC ACA CGC AAG CTG
Asp Lys Leu Leu Val Ala Thr Gly Arg Ala Pro Asn Thr Arg Lys Leu
            360                 365                 370

GCA CTG GAT GCG ACG GGC GTC ACG CTC ACC CCC CAA GGC GCT ATC GTC
Ala Leu Asp Ala Thr Gly Val Thr Leu Thr Pro Gln Gly Ala Ile Val
            375                 380                 385

ATC GAC CCC GGC ATG CGT ACA AGC GTG GAA CAC ATC TAC GCC GCA GGC
Ile Asp Pro Gly Met Arg Thr Ser Val Glu His Ile Tyr Ala Ala Gly
390                 395                 400                 405

GAC TGC ACC GAC CAG CCG CAG TTC GTC TAT GTG GCG GCA GCG GCC GGC
Asp Cys Thr Asp Gln Pro Gln Phe Val Tyr Val Ala Ala Ala Ala Gly
            410                 415                 420

ACT CGC GCC GCG ATC AAC ATG ACC GGC GGT GAC GCC GCC CTG AAC CTG
Thr Arg Ala Ala Ile Asn Met Thr Gly Gly Asp Ala Ala Leu Asn Leu
            425                 430                 435

ACC GCG ATG CCG GCC GTG GTG TTC ACC GAC CCG CAA GTG GCG ACC GTA
Thr Ala Met Pro Ala Val Val Phe Thr Asp Pro Gln Val Ala Thr Val
            440                 445                 450

GGC TAC AGC GAG GCG GAA GCG CAC CAT GAC GGC ATC AAA ACT GAT AGT
Gly Tyr Ser Glu Ala Glu Ala His His Asp Gly Ile Lys Thr Asp Ser
            455                 460                 465

CGC ACG CTA ACG CTG GAC AAC GTG CCG CGC GCG CTC GCC AAC TTC GAC
Arg Thr Leu Thr Leu Asp Asn Val Pro Arg Ala Leu Ala Asn Phe Asp
470                 475                 480                 485

ACG CGC GGC TTC ATC AAA CTG GTG GTT GAA GAA GGG AGC GGA CGA CTG
Thr Arg Gly Phe Ile Lys Leu Val Val Glu Glu Gly Ser Gly Arg Leu
            490                 495                 500

ATC GGC GTC CAG GCA GTG GCC CCG GAA GCG GGC GAA CTG ATC CAG ACG
Ile Gly Val Gln Ala Val Ala Pro Glu Ala Gly Glu Leu Ile Gln Thr
            505                 510                 515

GCC GCA CTG GCG ATT CGC AAC CGG ATG ACG GTG CAG GAA CTG GCC GAC
Ala Ala Leu Ala Ile Arg Asn Arg Met Thr Val Gln Glu Leu Ala Asp
            520                 525                 530

CAG TTG TTC CCC TAC CTG ACG ATG GTC GAA GGG TTG AAG CTC GCG GCG
Gln Leu Phe Pro Tyr Leu Thr Met Val Glu Gly Leu Lys Leu Ala Ala
            535                 540                 545

CAG ACC TTC AAC AAG GAT GTG AAG CAG CTT TCC TGC TGC GCC GGG TGA
Gln Thr Phe Asn Lys Asp Val Lys Gln Leu Ser Cys Cys Ala Gly *
550                 555                 560                 565

GGCTGCAGGA ATTCGATA
```

TABLE 7

MerApe 29 DNA and Amino Acid Sequences (SEQ ID NOs:29 and 30)

```
CTAGAACTAG TGGATCCCTA GATCTAAGAA GGAACCACA ATG AGC ACT CTC AAA
                                             Met Ser Thr Leu Lys

ATC ACC GGC ATG ACT TGC GAC TCG TGC GCA GTG CAT GTC AAG GAC GCC
Ile Thr Gly Met Thr Cys Asp Ser Cys Ala Val His Val Lys Asp Ala

CTG GAG AAA GTG CCC GGC GTG CAA TCA GCG GAT GTC TCC TAC GCC AAG
Leu Glu Lys Val Pro Gly Val Gln Ser Ala Asp Val Ser Tyr Ala Lys
```

TABLE 7-continued

MerApe 29 DNA and Amino Acid Sequences (SEQ ID NOs:29 and 30)

```
GGC AGC GCC AAG CTC GCC ATT GAG GTC GGC ACG TCA CCC GAC GCG CTG
Gly Ser Ala Lys Leu Ala Ile Glu Val Gly Thr Ser Pro Asp Ala Leu

ACG GCC GCT GTA GCT GGA CTC GGT TAT CGG GCC ACG CTG GCC GAT GCC
Thr Ala Ala Val Ala Gly Leu Gly Tyr Arg Ala Thr Leu Ala Asp Ala

CCC TCA GTT TCG ACG CCG GGC GGA TTG CTC GAC AAG ATG CGC GAT CTG
Pro Ser Val Ser Thr Pro Gly Gly Leu Leu Asp Lys Met Arg Asp Leu

CTG GGC AGA AAC GAC AAG ACG GGT AGC AGC GGC GCA TTG CAT ATG GCC
Leu Gly Arg Asn Asp Lys Thr Gly Ser Ser Gly Ala Leu His Ile Ala

GTC ATC GGC AGC GGC GGG GCC GCG ATG GCA GCG GCG CTG AAG GCC GTC
Val Ile Gly Ser Gly Gly Ala Ala Met Ala Ala Ala Leu Lys Ala Val

GAG CAA GGC GCA CCT GTC ACG CTG ATC GAG CGC GGC ACC ATC GGC GGC
Glu Gln Gly Ala Pro Val Thr Leu Ile Glu Arg Gly Thr Ile Gly Gly

ACC TGC GTC AAT GTC GGT TGT GTG CCG TCC AAG ATC ATG ATC CGC GCC
Thr Cys Val Asn Val Gly Cys Val Pro Ser Lys Ile Met Ile Arg Ala

GCC CAT ATC GCC CAT CTG CGC CGG GAA AGC CCG TTC GAT GGC GGC ATC
Ala His Ile Ala His Leu Arg Arg Glu Ser Pro Phe Asp Gly Gly Ile

GCC GCT ACC ACG CCG ACC ATC CAG CGC ACG GCG CTG CTG GCC CAG CAG
Ala Ala Thr Thr Pro Thr Ile Gln Arg Thr Ala Leu Leu Ala Gln Gln

CAG GCC CGC GTC GAT GAA CTG CGT CAT GCA AAG TAT GAA GGT ATT CTA
Gln Ala Arg Val Asp Glu Leu Arg His Ala Lys Tyr Glu Gly Ile Leu

GAA GGT AAC CCA GCC ATC ACT GTG CTT CAT GGC TCT GCA CGT TTC AAG
Glu Gly Asn Pro Ala Ile Thr Val Leu His Gly Ser Ala Arg Phe Lys

GAC AAC CGT AAC CTC ATT GTT CAA CTC AAC GAC GGC GGC GAG CGC GTG
Asp Asn Arg Asn Leu Ile Val Gln Leu Asn Asp Gly Gly Glu Arg Val

GTG GCA TTC GAC CGC TGT CTC ATT GCC ACT GGT GCA AGC CCA GCT GTT
Val Ala Phe Asp Arg Cys Leu Ile Ala Thr Gly Ala Ser Pro Ala Val

CCA CCA ATT CCT GGT CTC AAG GAC ACT CCT TAC TGG ACT TCC ACT GAA
Pro Pro Ile Pro Gly Leu Lys Asp Thr Pro Tyr Trp Thr Ser Thr Glu

GCA CTA GTG TCT GAG ACC ATT CCA AAG CGT CTT GCA GTC ATT GGC TCC
Ala Leu Val Ser Glu Thr Ile Pro Lys Arg Leu Ala Val Ile Gly Ser

TCT GTG GTG GCT CTT GAA CTT GCC CAG GCC TTT GCA CGT CTT GGT GCT
Ser Val Val Ala Leu Glu Leu Ala Gln Ala Phe Ala Arg Leu Gly Ala

AAA GTG ACC ATT CTT GCA CGC TCC ACT CTC TTC TTT CGT GAA GAC CCA
Lys Val Thr Ile Leu Ala Arg Ser Thr Leu Phe Phe Arg Glu Asp Pro

GCT ATA GGT GAA GCT GTT ACT GCT GCA TTT CGC ATG GAA GGC ATT GAA
Ala Ile Gly Glu Ala Val Thr Ala Ala Phe Arg Met Glu Gly Ile Glu

GTG CGT GAG CAT ACT CAA GCA AGC CAA GTT GCC TAT ATC AAT GGT GAA
Val Arg Glu His Thr Gln Ala Ser Gln Val Ala Tyr Ile Asn Gly Glu

GGG GAC GGC GAA TTC GTG CTC ACC ACG GCG CAC GGC GAA CTG CGC GCC
Gly Asp Gly Glu Phe Val Leu Thr Thr Ala His Gly Glu Leu Arg Ala

GAC AAG CTG CTG GTC GCC ACC GGC CGC GCG CCC AAC ACA CGC AAG CTG
Asp Lys Leu Leu Val Ala Thr Gly Arg Ala Pro Asn Thr Arg Lys Leu

GCA CTG GAT GCG ACG GGC GTC ACG CTC ACC CCC CAA GGC GCT ATC GTC
Ala Leu Asp Ala Thr Gly Val Thr Leu Thr Pro Gln Gly Ala Ile Val

ATC GAC CCC GGC ATG CGT ACA AGC GTG GAA CAC ATC TAC GCC GCA GGC
Ile Asp Pro Gly Met Arg Thr Ser Val Glu His Ile Tyr Ala Ala Gly

GAC TGC ACC GAC CAG CCG CAG TTC GTC TAT GTG GCG GCA GCG GCC GGC
Asp Cys Thr Asp Gln Pro Gln Phe Val Tyr Val Ala Ala Ala Ala Gly

ACT CGC GCC GCG ATC AAC ATG ACC GGC GGT GAC GCC GCC CTG AAC CTG
Thr Arg Ala Ala Ile Asn Met Thr Gly Gly Asp Ala Ala Leu Asn Leu
```

TABLE 7-continued

MerApe 29 DNA and Amino Acid Sequences (SEQ ID NOs:29 and 30)

```
ACC GCG ATG CCG GCC GTG GTG TTC ACC GAC CCG CAA GTG GCG ACC GTA
Thr Ala Met Pro Ala Val Val Phe Thr Asp Pro Gln Val Ala Thr Val

GGC TAC AGC GAG GCG GAA GCG CAC CAT GAC GGC ATC AAA ACT GAT AGT
Gly Tyr Ser Glu Ala Glu Ala His His Asp Gly Ile Lys Thr Asp Ser

CGC ACG CTA ACG CTG GAC AAC GTG CCG CGC GCG CTC GCC AAC TTC GAC
Arg Thr Leu Thr Leu Asp Asn Val Pro Arg Ala Leu Ala Asn Phe Asp

ACG CGC GGC TTC ATC AAA CTG GTG GTT GAA GAA GGG AGC GGA CGA CTG
Thr Arg Gly Phe Ile Lys Leu Val Val Glu Glu Gly Ser Gly Arg Leu

ATC GGC GTC CAG GCA GTG GCC CCG GAA GCG GGC GAA CTG ATC CAG ACG
Ile Gly Val Gln Ala Val Ala Pro Glu Ala Gly Glu Leu Ile Gln Thr

GCC GCA CTG GCG ATT CGC AAC CGG ATG ACG GTG CAG GAA CTG GCC GAC
Ala Ala Leu Ala Ile Arg Asn Arg Met Thr Val Gln Glu Leu Ala Asp

CAG TTG TTC CCC TAC CTG ACG ATG GTC GAA GGG TTG AAG CTC GCG GCG
Gln Leu Phe Pro Tyr Leu Thr Met Val Glu Gly Leu Lys Leu Ala Ala

CAG ACC TTC AAC AAG GAT GTG AAG CAG CTT TCC TGC TGC GCC GGG TGA
Gln Thr Phe Asn Lys Asp Val Lys Gln Leu Ser Cys Cys Ala Gly *

GGCTGCAGGA ATTCGATA
```

TABLE 8

MerApe 38 DNA and Amino Acid Sequences (SEQ ID NOs:13 and 14)

```
CTAGAACTAG TGGATCCCTA GATCTAAGAA GGAACCACA ATG AGC ACT CTC AAA
                                            Met Ser Thr Leu Lys
                                                            570

ATC ACC GGC ATG ACT TGC GAC TCG TGC GCA GTG CAT GTC AAG GAC GCC
Ile Thr Gly Met Thr Cys Asp Ser Cys Ala Val His Val Lys Asp Ala
            575                 580                     585

CTG GAG AAA GTG CCC GGC GTG CAA TCA GCG GAT GTC TCC TAC GCC AAG
Leu Glu Lys Val Pro Gly Val Gln Ser Ala Asp Val Ser Tyr Ala Lys
            590                 595                     600

GGC AGC GCC AAG CTC GCC ATT GAG GTC GGC ACG TCA CCC GAC GCG CTG
Gly Ser Ala Lys Leu Ala Ile Glu Val Gly Thr Ser Pro Asp Ala Leu
            605                 610                     615

ACG GCC GCT GTA GCT GGA CTC GGT TAT CGG GCC ACG CTG GCC GAT GCC
Thr Ala Ala Val Ala Gly Leu Gly Tyr Arg Ala Thr Leu Ala Asp Ala
        620                 625                     630

CCC TCA GTT TCG ACG CCG GGC GGA TTG CTC GAC AAG ATG CGC GAT CTG
Pro Ser Val Ser Thr Pro Gly Gly Leu Leu Asp Lys Met Arg Asp Leu
635                 640                 645                 650

CTG GGC AGA AAC GAC AAG ACG GGT AGC AGC GGC GCA TTG CAT ATG GCC
Leu Gly Arg Asn Asp Lys Thr Gly Ser Ser Gly Ala Leu His Met Ala
                655                 660                 665

GTC ATC GGC AGC GGC GGG GCC GCG ATG GCA GCG GCG CTG AAG GCC GTC
Val Ile Gly Ser Gly Gly Ala Ala Met Ala Ala Ala Leu Lys Ala Val
            670                 675                 680

GAG CAA GGC GCA CCT GTC ACG CTG ATC GAG CGC GGC ACC ATC GGC GGC
Glu Gln Gly Ala Pro Val Thr Leu Ile Glu Arg Gly Thr Ile Gly Gly
            685                 690                 695

ACC TGC GTC AAT GTC GGT TGT GTG CCG TCC AAG ATC ATG ATC CGC GCC
Thr Cys Val Asn Val Gly Cys Val Pro Ser Lys Ile Met Ile Arg Ala
        700                 705                 710

GCC CAT ATC GCC CAT CTG CGC CGG GAA AGC CCG TTC GAT GGC GGC ATC
Ala His Ile Ala His Leu Arg Arg Glu Ser Pro Phe Asp Gly Gly Ile
715                 720                 725                 730
```

TABLE 8-continued

MerApe 38 DNA and Amino Acid Sequences (SEQ ID NOs:13 and 14)

```
GCC GCT ACC ACG CCG ACC ATC CAG CGC ACG GCG CTG CTG GCC CAG CAG
Ala Ala Thr Thr Pro Thr Ile Gln Arg Thr Ala Leu Leu Ala Gln Gln
            735             740             745

CAG GCC CGC GTC GAT GAA CTG CGT CAT GCA AAG TAT GAA GGT ATT CTA
Gln Ala Arg Val Asp Glu Leu Arg His Ala Lys Tyr Glu Gly Ile Leu
            750             755             760

GAA GGT AAC CCA GCC ATC ACT GTG CTT CAT GGC TCT GCA CGT TTT AAG
Glu Gly Asn Pro Ala Ile Thr Val Leu His Gly Ser Ala Arg Phe Lys
            765             770             775

GAC AAC CGT AAC CTC ATT GTT CAA CTC AAC GAC GGC GGC GAG CGC GTG
Asp Asn Arg Asn Leu Ile Val Gln Leu Asn Asp Gly Gly Glu Arg Val
            780             785             790

GTG GCA TTC GAC CGC TGT CTC ATT GCC ACT GGT GCA AGC CCA GCT GTT
Val Ala Phe Asp Arg Cys Leu Ile Ala Thr Gly Ala Ser Pro Ala Val
795             800             805             810

CCA CCA ATT CCT GGT CTC AAG GAC ACT CCT TAC TGG ACT TCC ACT GAA
Pro Pro Ile Pro Gly Leu Lys Asp Thr Pro Tyr Trp Thr Ser Thr Glu
            815             820             825

GCA CTA GTG TCT GAG ACC ATT CCA AAG CGT CTT GCA GTC ATT GGC TCC
Ala Leu Val Ser Glu Thr Ile Pro Lys Arg Leu Ala Val Ile Gly Ser
            830             835             840

TCT GTG GTG GCT CTT GAA CTT GCC CAG GCC TTT GCA CGT CTT GGT GCT
Ser Val Val Ala Leu Glu Leu Ala Gln Ala Phe Ala Arg Leu Gly Ala
            845             850             855

AAA GTG ACC ATT CTT GCA CGC TCC ACT CTC TTC TTT CGT GAA GAC CCA
Lys Val Thr Ile Leu Ala Arg Ser Thr Leu Phe Phe Arg Glu Asp Pro
            860             865             870

GCT ATA GGT GAA GCT GTT ACT GCT GCA TTT CGC ATG GAA GGC ATT GAA
Ala Ile Gly Glu Ala Val Thr Ala Ala Phe Arg Met Glu Gly Ile Glu
875             880             885             890

GTG CGT GAG CAT ACT CAA GCA AGC CAA GTT GCC TAT ATC AAT GGT GAA
Val Arg Glu His Thr Gln Ala Ser Gln Val Ala Tyr Ile Asn Gly Glu
            895             900             905

GGT GAC GGT GAA TTC GTC CTA ACC ACT GCT CAT GGT GAA CTT CGT GCA
Gly Asp Gly Glu Phe Val Leu Thr Thr Ala His Gly Glu Leu Arg Ala
            910             915             920

GAC AAA CTC CTT GTT GCA ACT GGT CGT GCA CCA AAC ACT CGC AAA CTG
Asp Lys Leu Leu Val Ala Thr Gly Arg Ala Pro Asn Thr Arg Lys Leu
            925             930             935

GCA CTT GAT GCA ACT GGT GTG ACC CTT ACT CCA CAA GGT GCT ATT GTC
Ala Leu Asp Ala Thr Gly Val Thr Leu Thr Pro Gln Gly Ala Ile Val
            940             945             950

ATC GAC CCC GGC ATG CGT ACA AGC GTG GAA CAC ATC TAC GCC GCA GGC
Ile Asp Pro Gly Met Arg Thr Ser Val Glu His Ile Tyr Ala Ala Gly
955             960             965             970

GAC TGC ACC GAC CAG CCG CAG TTC GTC TAT GTG GCG GCA GCG GCC GGC
Asp Cys Thr Asp Gln Pro Gln Phe Val Tyr Val Ala Ala Ala Ala Gly
            975             980             985

ACT CGC GCC GCG ATC AAC ATG ACC GGC GGT GAC GCC GCC CTG AAC CTG
Thr Arg Ala Ala Ile Asn Met Thr Gly Gly Asp Ala Ala Leu Asn Leu
            990             995             1000

ACC GCG ATG CCG GCC GTG GTG TTC ACC GAC CCG CAA GTG GCG ACC GTA
Thr Ala Met Pro Ala Val Val Phe Thr Asp Pro Gln Val Ala Thr Val
            1005            1010            1015

GGC TAC AGC GAG GCG GAA GCG CAC CAT GAC GGC ATC AAA ACT GAT AGT
Gly Tyr Ser Glu Ala Glu Ala His His Asp Gly Ile Lys Thr Asp Ser
            1020            1025            1030
```

TABLE 8-continued

MerApe 38 DNA and Amino Acid Sequences (SEQ ID NOs:13 and 14)

```
CGC ACG CTA ACG CTG GAC AAC GTG CCG CGC GCG CTC GCC AAC TTC GAC
Arg Thr Leu Thr Leu Asp Asn Val Pro Arg Ala Leu Ala Asn Phe Asp
1035              1040              1045              1050

ACG CGC GGC TTC ATC AAA CTG GTG GTT GAA GAA GGG AGC GGA CGA CTG
Thr Arg Gly Phe Ile Lys Leu Val Val Glu Glu Gly Ser Gly Arg Leu
                  1055              1060              1065

ATC GGC GTC CAG GCA GTG GCC CCG GAA GCG GGC GAA CTG ATC CAG ACG
Ile Gly Val Gln Ala Val Ala Pro Glu Ala Gly Glu Leu Ile Gln Thr
              1070              1075              1080

GCC GCA CTG GCG ATT CGC AAC CGG ATG ACG GTG CAG GAA CTG GCC GAC
Ala Ala Leu Ala Ile Arg Asn Arg Met Thr Val Gln Glu Leu Ala Asp
          1085              1090              1095

CAG TTG TTC CCC TAC CTG ACG ATG GTC GAA GGG TTG AAG CTC GCG GCG
Gln Leu Phe Pro Tyr Leu Thr Met Val Glu Gly Leu Lys Leu Ala Ala
      1100              1105              1110

CAG ACC TTC AAC AAG GAT GTG AAG CAG CTT TCC TGC TGC GCC GGG TGA
Gln Thr Phe Asn Lys Asp Val Lys Gln Leu Ser Cys Cys Ala Gly *
1115              1120              1125              1130

GGCTGCAGGA ATTCGATA
```

TABLE 9

MerApe 47 DNA and Amino Acid Sequences (SEQ ID NOs:19 and 20)

```
CTAGAACTAG TGGATCCCTA GATCTAAGAA GGAACCACA ATG AGC ACT CTC AAA
                                          Met Ser Thr Leu Lys
                                                          570

ATC ACC GGC ATG ACT TGC GAC TCG TGC GCA GTG CAT GTC AAG GAC GCC
Ile Thr Gly Met Thr Cys Asp Ser Cys Ala Val His Val Lys Asp Ala
                  575              580              585

CTG GAG AAA GTG CCC GGC GTG CAA TCA GCG GAT GTC TCC TAC GCC AAG
Leu Glu Lys Val Pro Gly Val Gln Ser Ala Asp Val Ser Tyr Ala Lys
              590              595              600

GGC AGC GCC AAG CTC GCC ATT GAG GTC GGC ACG TCA CCC GAC GCG CTG
Gly Ser Ala Lys Leu Ala Ile Glu Val Gly Thr Ser Pro Asp Ala Leu
          605              610              615

ACG GCC GCT GTA GCT GGA CTC GGT TAT CGG GCC ACG CTG GCC GAT GCC
Thr Ala Ala Val Ala Gly Leu Gly Tyr Arg Ala Thr Leu Ala Asp Ala
      620              625              630

CCC TCA GTT TCG ACG CCG GGC GGA TTG CTC GAC AAG ATG CGC GAT CTG
Pro Ser Val Ser Thr Pro Gly Gly Leu Leu Asp Lys Met Arg Asp Leu
635              640              645              650

CTG GGC AGA AAC GAC AAG ACG GGT AGC AGC GGC GCA TTG CAT ATG GCC
Leu Gly Arg Asn Asp Lys Thr Gly Ser Ser Gly Ala Leu His Ile Ala
                  655              660              665

GTC ATC GGC AGC GGC GGG GCC GCG ATG GCA GCG GCG CTG AAG GCC GTC
Val Ile Gly Ser Gly Gly Ala Ala Met Ala Ala Ala Leu Lys Ala Val
              670              675              680

GAG CAA GGC GCA CCT GTC ACG CTG ATC GAG CGC GGC ACC ATC GGC GGC
Glu Gln Gly Ala Pro Val Thr Leu Ile Glu Arg Gly Thr Ile Gly Gly
          685              690              695

ACC TGC GTT AAT GTT GGT TGT GTG CCG AGC AAG ATC ATG ATT CGT GCT
Thr Cys Val Asn Val Gly Cys Val Pro Ser Lys Ile Met Ile Arg Ala
      700              705              710

GCT CAC ATT GCT CAT CTT CGT CGT GAA TCT CCA TTT GAT GGT GGC ATT
Ala His Ile Ala His Leu Arg Arg Glu Ser Pro Phe Asp Gly Gly Ile
715              720              725              730
```

TABLE 9-continued

MerApe 47 DNA and Amino Acid Sequences (SEQ ID NOs:19 and 20)

```
GCT GCA ACC ACT CCA ACC ATT CAA CGT ACT GCA CTC CTT GCA CAA CAA
Ala Ala Thr Thr Pro Thr Ile Gln Arg Thr Ala Leu Leu Ala Gln Gln
            735                 740                 745

CAA GCA CGT GTT GAT GAA CTT CGT CAT GCA AAG TAT GAA GGT ATT CTA
Gln Ala Arg Val Asp Glu Leu Arg His Ala Lys Tyr Glu Gly Ile Leu
            750                 755                 760

GAA GGT AAC CCA GCC ATC ACT GTG CTT CAT GGC TCT GCA CGT TTT AAG
Glu Gly Asn Pro Ala Ile Thr Val Leu His Gly Ser Ala Arg Phe Lys
            765                 770                 775

GAC AAC CGT AAC CTC ATT GTT CAA CTC AAC GAC GGC GGC GAG CGC GTG
Asp Asn Arg Asn Leu Ile Val Gln Leu Asn Asp Gly Gly Glu Arg Val
            780                 785                 790

GTG GCA TTC GAC CGC TGT CTC ATT GCC ACT GGT GCA AGC CCA GCT GTT
Val Ala Phe Asp Arg Cys Leu Ile Ala Thr Gly Ala Ser Pro Ala Val
795                 800                 805                 810

CCA CCA ATT CCT GGT CTC AAG GAC ACT CCT TAC TGG ACT TCC ACT GAA
Pro Pro Ile Pro Gly Leu Lys Asp Thr Pro Tyr Trp Thr Ser Thr Glu
            815                 820                 825

GCA CTA GTG TCT GAG ACC ATT CCA AAG CGT CTT GCA GTC ATT GGC TCC
Ala Leu Val Ser Glu Thr Ile Pro Lys Arg Leu Ala Val Ile Gly Ser
            830                 835                 840

TCT GTG GTG GCT CTT GAA CTT GCC CAG GCC TTT GCA CGT CTT GGT GCT
Ser Val Val Ala Leu Glu Leu Ala Gln Ala Phe Ala Arg Leu Gly Ala
            845                 850                 855

AAA GTG ACC ATT CTT GCA CGC TCC ACT CTC TTC TTT CGT GAA GAC CCA
Lys Val Thr Ile Leu Ala Arg Ser Thr Leu Phe Phe Arg Glu Asp Pro
            860                 865                 870

GCT ATA GGT GAA GCT GTT ACT GCT GCA TTT CGC ATG GAA GGC ATT GAA
Ala Ile Gly Glu Ala Val Thr Ala Ala Phe Arg Met Glu Gly Ile Glu
875                 880                 885                 890

GTG CGT GAG CAT ACT CAA GCA AGC CAA GTT GCC TAT ATC AAT GGT GAA
Val Arg Glu His Thr Gln Ala Ser Gln Val Ala Tyr Ile Asn Gly Glu
            895                 900                 905

GGT GAC GGT GAA TTC GTC CTA ACC ACT GCT CAT GGT GAA CTT CGT GCA
Gly Asp Gly Glu Phe Val Leu Thr Thr Ala His Gly Glu Leu Arg Ala
            910                 915                 920

GAC AAA CTC CTT GTT GCA ACT GGT CGT GCA CCA AAC ACT CGC AAA CTG
Asp Lys Leu Leu Val Ala Thr Gly Arg Ala Pro Asn Thr Arg Lys Leu
            925                 930                 935

GCA CTT GAT GCA ACT GGT GTG ACC CTT ACT CCA CAA GGT GCT ATT GTC
Ala Leu Asp Ala Thr Gly Val Thr Leu Thr Pro Gln Gly Ala Ile Val
            940                 945                 950

ATC GAC CCC GGC ATG CGT ACA AGC GTG GAA CAC ATC TAC GCC GCA GGC
Ile Asp Pro Gly Met Arg Thr Ser Val Glu His Ile Tyr Ala Ala Gly
955                 960                 965                 970

GAC TGC ACC GAC CAG CCG CAG TTC GTC TAT GTG GCG GCA GCG GCC GGC
Asp Cys Thr Asp Gln Pro Gln Phe Val Tyr Val Ala Ala Ala Ala Gly
            975                 980                 985

ACT CGC GCC GCG ATC AAC ATG ACC GGC GGT GAC GCC GCC CTG AAC CTG
Thr Arg Ala Ala Ile Asn Met Thr Gly Gly Asp Ala Ala Leu Asn Leu
            990                 995                 1000

ACC GCG ATG CCG GCC GTG GTG TTC ACC GAC CCG CAA GTG GCG ACC GTA
Thr Ala Met Pro Ala Val Val Phe Thr Asp Pro Gln Val Ala Thr Val
            1005                1010                1015

GGC TAC AGC GAG GCG GAA GCG CAC CAT GAC GGC ATC AAA ACT GAT AGT
Gly Tyr Ser Glu Ala Glu Ala His His Asp Gly Ile Lys Thr Asp Ser
            1020                1025                1030
```

TABLE 9-continued

MerApe 47 DNA and Amino Acid Sequences (SEQ ID NOs:19 and 20)

```
CGC ACG CTA ACG CTG GAC AAC GTG CCG CGC GCG CTC GCC AAC TTC GAC
Arg Thr Leu Thr Leu Asp Asn Val Pro Arg Ala Leu Ala Asn Phe Asp
1035              1040              1045              1050

ACG CGC GGC TTC ATC AAA CTG GTG GTT GAA GAA GGG AGC GGA CGA CTG
Thr Arg Gly Phe Ile Lys Leu Val Val Glu Glu Gly Ser Gly Arg Leu
              1055              1060              1065

ATC GGC GTC CAG GCA GTG GCC CCG GAA GCG GGC GAA CTG ATC CAG ACG
Ile Gly Val Gln Ala Val Ala Pro Glu Ala Gly Glu Leu Ile Gln Thr
              1070              1075              1080

GCC GCA CTG GCG ATT CGC AAC CGG ATG ACG GTG CAG GAA CTG GCC GAC
Ala Ala Leu Ala Ile Arg Asn Arg Met Thr Val Gln Glu Leu Ala Asp
          1085              1090              1095

CAG TTG TTC CCC TAC CTG ACG ATG GTC GAA GGG TTG AAG CTC GCG GCG
Gln Leu Phe Pro Tyr Leu Thr Met Val Glu Gly Leu Lys Leu Ala Ala
      1100              1105              1110

CAG ACC TTC AAC AAG GAT GTG AAG CAG CTT TCC TGC TGC GCC GGG TGA
Gln Thr Phe Asn Lys Asp Val Lys Gln Leu Ser Cys Cys Ala Gly *
1115              1120              1125              1130

GGCTGCAGGA ATTCGATA
```

TABLE 10

MerApe100 Nucleotide and Amino Acid Sequences (SEQ ID NOs:31 and 32)

```
    ATGTCTACTCTGAAGATCACTGGTATGACTTGTGACTCTTGTGCAGTGCATGTcAAGGAT
  1 ---------+---------+---------+---------+---------+---------+60
    M  S  T  L  K  I  T  G  M  T  C  D  S  C  A  V  H  V  K  D   -

GCACTGGAGAAAGTTCCAGGTGTGCAATCTGCAGATGTGAGCTATGCAAAGGGCTCTGCC
 61 ---------+---------+---------+---------+---------+---------+120
     A  L  E  K  V  P  G  V  Q  S  A  D  V  S  Y  A  K  G  S  A  -

AAATTGGCCATTGAAGTTGGCACTTCTCCAGATGCACTTACTGCTGCTGTTGCAGGTCTG
121 ---------+---------+---------+---------+---------+---------+180
     K  L  A  I  E  V  G  T  S  P  D  A  L  T  A  A  V  A  G  L  -

GGCTATCGTGCTACTCTTGCAGATGCACCATCTGTGTCTACTCCAGGTGGTCTGCTTGAT
181 ---------+---------+---------+---------+---------+---------+240
     G  Y  R  A  T  L  A  D  A  P  S  V  S  T  P  G  G  L  L  D  -

AAGATGCGTGACCTGCTTGGTCGTAATGACAAGACTGGCAGCTCTGGTGCACTCCACATT
241 ---------+---------+---------+---------+---------+---------+300
     K  M  R  D  L  L  G  R  N  D  K  T  G  S  S  G  A  L  H  I  -

GCTGTGATTGGCTCTGGTGGTGCAGCAATGGCAGCAGCACTTAAAGCTGTTGAACAAGGT
301 ---------+---------+---------+---------+---------+---------+360
     A  V  I  G  S  G  G  A  A  M  A  A  A  L  K  A  V  E  Q  G  -

GCTCGTGTGACTCTGATTGAACGTGGCACTATTGGTGGCACTTGTGTTAATGTTGGTTGT
361 ---------+---------+---------+---------+---------+---------+420
     A  R  V  T  L  I  E  R  G  T  I  G  G  T  C  V  N  V  G  C  -

GTGCCAAGCAAGATCATGATTCGTGCTGCTCACATTGCTCATCTTCGTCGTGAATCTCCA
421 ---------+---------+---------+---------+---------+---------+480
     V  P  S  K  I  M  I  R  A  A  H  I  A  H  L  R  R  E  S  P  -

TTTGATGGTGGCATTGCTGCAACCACTCCAACCATTCAACGTACTGCACTCCTTGCACAA
481 ---------+---------+---------+---------+---------+---------+540
     F  D  G  G  I  A  A  T  T  P  T  I  Q  R  T  A  L  L  A  Q  -

CAACAAGCACGTGTTGATGAACTTCGTCATGCAAAGTATGAAGGTATCCTGGAAGGTAAC
541 ---------+---------+---------+---------+---------+---------+600
     Q  Q  A  R  V  D  E  L  R  H  A  K  Y  E  G  I  L  E  G  N  -

CCAGCCATCACTGTGCTTCATGGCTCTGCACGTTTCAAgGAcAAcCGTAACCTCATTGTT
601 ---------+---------+---------+---------+---------+---------+660
     P  A  I  T  V  L  H  G  S  A  R  F  K  D  N  R  N  L  I  V  -
```

TABLE 10-continued

MerApe100 Nucleotide and Amino Acid Sequences (SEQ ID NOs:31 and 32)

```
      CAACTTAATGATGGTGGTGAACGTGTGGTGGCTTTTGACCGCTGTCTCATTGCCACTGGT
  661 ---------+---------+---------+---------+---------+---------+720
        Q  L  N  D  G  G  E  R  V  V  A  F  D  R  C  L  I  A  T  G  -

GCAAGCCCAGCTGTTCCACCAATTCCTGGTCTCAAGGACACTCCTTACTGGACTTCCACT
  721 ---------+---------+---------+---------+---------+---------+780
        A  S  P  A  V  P  P  I  P  G  L  K  D  T  P  Y  W  T  S  T  -

GAAGCTCTTGTGTCTGAGACCATTCCAAAGCGTCTTGCAGTCATTGGCTCCTCTGTGGTG
  781 ---------+---------+---------+---------+---------+---------+840
        E  A  L  V  S  E  T  I  P  K  R  L  A  V  I  G  S  S  V  V  -

GCTCTTGAACTTGCCCAGGCCTTTGCACGTCTTGGTGCTAAAGTGACCATTCTTGCACGC
  841 ---------+---------+---------+---------+---------+---------+900
        A  L  E  L  A  Q  A  F  A  R  L  G  A  K  V  T  I  L  A  R  -

TCCACTCTCTTCTTTCGTGAAGACCCAGCAATTGGTGAAGCTGTTACTGCTGCATTTCGC
  901 ---------+---------+---------+---------+---------+---------+960
        S  T  L  F  F  R  E  D  P  A  I  G  E  A  V  T  A  A  F  R  -

ATGGAAGGCATTGAAGTGCGTGAGCATACTCAAGCAAGCCAAGTTGCCTATATCAATGGT
  961 ---------+---------+---------+---------+---------+---------+1020
        M  E  G  I  E  V  R  E  H  T  Q  A  S  Q  V  A  Y  I  N  G  -

GAAGGTGATGGTGACTTTGTCCTTACCACTGCTCATGGTGAACTTCGTGCAGACAAACTC
 1021 ---------+---------+---------+---------+---------+---------+1080
        E  G  D  G  D  F  V  L  T  T  A  H  G  E  L  R  A  D  K  L  -

CTTGTTGCAACTGGTCGTGCACCAAACACTCGCAAACTGGCACTTGATGCAACTGGTGTG
 1081 ---------+---------+---------+---------+---------+---------+1140
        L  V  A  T  G  R  A  P  N  T  R  K  L  A  L  D  A  T  G  V  -

ACCCTTACTCCACAAGGTGCTATTGTGATTGATCCAGGTATGCGTACCTCTGTGGAACAC
 1141 ---------+---------+---------+---------+---------+---------+1200
        T  L  T  P  Q  G  A  I  V  I  D  P  G  M  R  T  S  V  E  H  -

ATCTATGCAGCTGGTGATTGCACTGATCAACCACAATTTGTGTATGTTGCTGCTGCTGCT
 1201 ---------+---------+---------+---------+---------+---------+1260
        I  Y  A  A  G  D  C  T  D  Q  P  Q  F  V  Y  V  A  A  A  A  -

GGTACTCGTGCTGCTATCAACATGACTGGTGGTGATGCTGCCCTCAACCTCACTGCTATG
 1261 ---------+---------+---------+---------+---------+---------+1320
        G  T  R  A  A  I  N  M  T  G  G  D  A  A  L  N  L  T  A  M  -

CCAGCTGTTGTGTTCACTGACCCACAAGTGGCTACTGTGGGTTATTCTGAAGCTGAAGCT
 1321 ---------+---------+---------+---------+---------+---------+1380
        P  A  V  V  F  T  D  P  Q  V  A  T  V  G  Y  S  E  A  E  A  -

CATCATGATGGCATCAAGACTGACTCTCGCACTCTCACTCTTGACAATGTGCCACGTGCC
 1381 ---------+---------+---------+---------+---------+---------+1440
        H  H  D  G  I  K  T  D  S  R  T  L  T  L  D  N  V  P  R  A  -

CTGGCCAACTTTGATACTCGTGGCTTTATCAAACTTGTGGTGGAAGAAGGCTCTGGTCGT
 1441 ---------+---------+---------+---------+---------+---------+1500
        L  A  N  F  D  T  R  G  F  I  K  L  V  V  E  E  G  S  G  R  -

CTTATTGGTGTGCAAGCAGTGGCACCAGAAGCTGGTGAACTCATTCAAACTGCTGCACTT
 1501 ---------+---------+---------+---------+---------+---------+1560
        L  I  G  V  Q  A  V  A  P  E  A  G  E  L  I  Q  T  A  A  L  -

GCTATTCGCAACCGTATGACTGTGCAAGAACTGGCTGATCAGCTGTTTCCATACCTCACT
 1561 ---------+---------+---------+---------+---------+---------+1620
        A  I  R  N  R  M  T  V  Q  E  L  A  D  Q  L  F  P  Y  L  T  -

ATGGTGGAAGGTCTCAAGCTCGCTGCTCAAACCTTCAACAAGGATGTGAAGCAGCTGAGC
 1621 ---------+---------+---------+---------+---------+---------+1680
        M  V  E  G  L  K  L  A  A  Q  T  F  N  K  D  V  K  Q  L  S  -

Stop
      TGCTGTGCTGGCTAA
 1681 ---------+-----1695
        C  C  A  G  *
```

TABLE 11

MerBpe Coding and Amino Acid Sequences (SEQ ID NOs:33 and 34)

```
         Clamp        EcoRI          SD      PT
              BamHI       BglII   Stop
         GCGGTCGGATCCGAATTCGTCGACTAAGGAGGAGCCACA
      1  +--------+---------+---------+--------39

ATGAAGCTCGCCCCATATATTTTAGAACTTCTCACTTCGGTCAATCGTACCAATGGTACT
 40  +---------+---------+---------+---------+---------+---------99
       M  K  L  A  P  Y  I  L  E  L  L  T  S  V  N  R  T  N  G  T   -

GCGGATCTCTTGGTCCCGCTACTGCGGGAACTCGCCAAGGGGCGTCCGGTTTCACGAACG
100  +---------+---------+---------+---------+---------+---------159
       A  D  L  L  V  P  L  L  R  E  L  A  K  G  R  P  V  S  R  T   -

ACACTTGCCGGGATTCTCGACTGGCCCGCTGAGCGAGTGGCCGCCGTACTCGAACAGGCC
160  +---------+---------+---------+---------+---------+---------219
       T  L  A  G  I  L  D  W  P  A  E  R  V  A  A  V  L  E  Q  A   -

ACCAGTACCGAATATGACAAAGATGGGAACATCATCGGCTACGGCCTCACCTTGCGCGAG
220  +---------+---------+---------+---------+---------+---------279
  T  S  T  E  Y  D  K  D  G  N  I  I  G  Y  G  L  T  L  R  E    -

ACTTCGTATGTCTTTGAAATTGACGACCGCCGTCTGTATGCCTGGTGCGCGCTGGACACC
280  +---------+---------+---------+---------+---------+---------339
       T  S  Y  V  F  E  I  D  D  R  R  L  Y  A  W  C  A  L  D  T   -

TTGATATTTCCGGCGCTGATCGGCCGTACAGCTCGCGTCTCATCGCATTGCGCTGCAACC
340  +---------+---------+---------+---------+---------+---------399
       L  I  F  P  A  L  I  G  R  T  A  R  V  S  S  H  C  A  A  T   -

GGAGCACCGGTTTCACTCACGGTTTCACCCAGCGAGATACAGGCTGTCGAACCTGCCGGC
400  +---------+---------+---------+---------+---------+---------459
       G  A  P  V  S  L  T  V  S  P  S  E  I  Q  A  V  E  P  A  G   -

ATGGCGGTGTCCTTGGTATTGCCGCAGGAAGCAGCCGACGTTCGTCAGTCCTTCTGTTGC
460  +---------+---------+---------+---------+---------+---------519
       M  A  V  S  L  V  L  P  Q  E  A  A  D  V  R  Q  S  F  C  C   -

CATGTACATTTCTTTGCATCTGTCCCGACGGCGGAAGACTGGGCCTCCAAGCATCAAGGA
520  +---------+---------+---------+---------+---------+---------579
       H  V  H  F  F  A  S  V  P  T  A  E  D  W  A  S  K  H  Q  G   -

TTGGAAGGATTGGCGATCGTCAGTGTCCACGAGGCTTTCGGCTTGGGCCAGGAGTTTAAT
580  +---------+---------+---------+---------+---------+---------639
       L  E  G  L  A  I  V  S  V  H  E  A  F  G  L  G  Q  E  F  N   -

Stop
                                        Stop
     CGACATCTGTTGCAGACCATGTCATCTAGGACACCGTGATAA
640  +---------+---------+---------+---------+-681
       R  H  L  L  Q  T  M  S  S  R  T  P  *  *

EcoRI
  HindIII    BamHI  Clamp
     GCTTGAATTCGGATCCGATACG
682  --------+---------+---703
```

---

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 1728 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (ix) FEATURE:
   (A) NAME/KEY: CDS
   (B) LOCATION: 14..1708

(xi) SEQUENCE DESCRIPTION: SEQ ID NO:1:

```
AAGGAACGAT GGT ATG AGC ACT CTC AAA ATC ACC GGC ATG ACT TGC GAC          49
            Met Ser Thr Leu Lys Ile Thr Gly Met Thr Cys Asp
              1               5                  10

TCG TGC GCA GTG CAT GTC AAG GAC GCC CTG GAG AAA GTG CCC GGC GTG         97
Ser Cys Ala Val His Val Lys Asp Ala Leu Glu Lys Val Pro Gly Val
             15                  20                  25

CAA TCA GCG GAT GTC TCC TAC GCC AAG GGC AGC GCC AAG CTC GCC ATT        145
Gln Ser Ala Asp Val Ser Tyr Ala Lys Gly Ser Ala Lys Leu Ala Ile
         30                  35                  40

GAG GTC GGC ACG TCA CCC GAC GCG CTG ACG GCC GCT GTA GCT GGA CTC        193
Glu Val Gly Thr Ser Pro Asp Ala Leu Thr Ala Ala Val Ala Gly Leu
 45                  50                  55                  60

GGT TAT CGG GCC ACG CTG GCC GAT GCC CCC TCA GTT TCG ACG CCG GGC        241
Gly Tyr Arg Ala Thr Leu Ala Asp Ala Pro Ser Val Ser Thr Pro Gly
                 65                  70                  75

GGA TTG CTC GAC AAG ATG CGC GAT CTG CTG GGC AGA AAC GAC AAG ACG        289
Gly Leu Leu Asp Lys Met Arg Asp Leu Leu Gly Arg Asn Asp Lys Thr
             80                  85                  90

GGT AGC AGC GGC GCA TTG CAT ATC GCC GTC ATC GGC AGC GGC GGG GCC        337
Gly Ser Ser Gly Ala Leu His Ile Ala Val Ile Gly Ser Gly Gly Ala
         95                 100                 105

GCG ATG GCA GCG GCG CTG AAG GCC GTC GAG CAA GGC GCA CCT GTC ACG        385
Ala Met Ala Ala Ala Leu Lys Ala Val Glu Gln Gly Ala Pro Val Thr
     110                 115                 120

CTG ATC GAG CGC GGC ACC ATC GGC GGC ACC TGC GTC AAT GTC GGT TGT        433
Leu Ile Glu Arg Gly Thr Ile Gly Gly Thr Cys Val Asn Val Gly Cys
125                 130                 135                 140

GTG CCG TCC AAG ATC ATG ATC CGC GCC GCC CAT ATC GCC CAT CTG CGC        481
Val Pro Ser Lys Ile Met Ile Arg Ala Ala His Ile Ala His Leu Arg
                145                 150                 155

CGG GAA AGC CCG TTC GAT GGC GGC ATC GCC GCT ACC ACG CCG ACC ATC        529
Arg Glu Ser Pro Phe Asp Gly Gly Ile Ala Ala Thr Thr Pro Thr Ile
            160                 165                 170

CAG CGC ACG GCG CTG CTG GCC CAG CAG CAG GCC CGC GTC GAT GAA CTG        577
Gln Arg Thr Ala Leu Leu Ala Gln Gln Gln Ala Arg Val Asp Glu Leu
        175                 180                 185

CGC CAC GCC AAG TAC GAA GGC ATC TTG GAG GGC AAT CCG GCG ATC ACT        625
Arg His Ala Lys Tyr Glu Gly Ile Leu Glu Gly Asn Pro Ala Ile Thr
    190                 195                 200

GTG CTG CAC GGC TCC GCC CGC TTT AAG GAC AAT CGC AAC CTG ATC GTG        673
Val Leu His Gly Ser Ala Arg Phe Lys Asp Asn Arg Asn Leu Ile Val
205                 210                 215                 220

CAA CTC AAC GAC GGC GGC GAG CGC GTG GTG GCA TTC GAC CGC TGC CTG        721
Gln Leu Asn Asp Gly Gly Glu Arg Val Val Ala Phe Asp Arg Cys Leu
                225                 230                 235

ATC GCC ACC GGC GCG AGC CCG GCC GTG CCG CCG ATT CCC GGC CTG AAA        769
Ile Ala Thr Gly Ala Ser Pro Ala Val Pro Pro Ile Pro Gly Leu Lys
            240                 245                 250

GAC ACT CCG TAC TGG ACT TCC ACT GAA GCG CTG GTC AGC GAG ACG ATT        817
Asp Thr Pro Tyr Trp Thr Ser Thr Glu Ala Leu Val Ser Glu Thr Ile
        255                 260                 265

CCT AAG CGC CTG GCC GTG ATT GGC TCA TCA GTG CTG GCG CTG GAG CTG        865
```

```
                Pro Lys Arg Leu Ala Val Ile Gly Ser Ser Val Leu Ala Leu Glu Leu
                    270                 275                 280

GCG CAG GCG TTC GCC CGA CTC GGA GCG AAG GTG ACG ATC CTG GCT CGC              913
Ala Gln Ala Phe Ala Arg Leu Gly Ala Lys Val Thr Ile Leu Ala Arg
285                 290                 295                 300

AGC ACG CTG TTC TTC CGC GAA GAC CCA GCT ATA GGC GAA GCT GTC ACG              961
Ser Thr Leu Phe Phe Arg Glu Asp Pro Ala Ile Gly Glu Ala Val Thr
                305                 310                 315

GCC GCA TTC CGG ATG GAG GGC ATC GAG GTG AGG GAA CAC ACC CAG GCC             1009
Ala Ala Phe Arg Met Glu Gly Ile Glu Val Arg Glu His Thr Gln Ala
                320                 325                 330

AGC CAG GTC GCG TAT ATC AAT GGT GAA GGG GAC GGC GAA TTC GTG CTC             1057
Ser Gln Val Ala Tyr Ile Asn Gly Glu Gly Asp Gly Glu Phe Val Leu
                335                 340                 345

ACC ACG GCG CAC GGC GAA CTG CGC GCC GAC AAG CTG CTG GTC GCC ACC             1105
Thr Thr Ala His Gly Glu Leu Arg Ala Asp Lys Leu Leu Val Ala Thr
350                 355                 360

GGC CGC GCG CCC AAC ACA CGC AAG CTG GCA CTG GAT GCG ACG GGC GTC             1153
Gly Arg Ala Pro Asn Thr Arg Lys Leu Ala Leu Asp Ala Thr Gly Val
365                 370                 375                 380

ACG CTC ACC CCC CAA GGC GCT ATC GTC ATC GAC CCC GGC ATG CGT ACA             1201
Thr Leu Thr Pro Gln Gly Ala Ile Val Ile Asp Pro Gly Met Arg Thr
                385                 390                 395

AGC GTG GAA CAC ATC TAC GCC GCA GGC GAC TGC ACC GAC CAG CCG CAG             1249
Ser Val Glu His Ile Tyr Ala Ala Gly Asp Cys Thr Asp Gln Pro Gln
                400                 405                 410

TTC GTC TAT GTG GCG GCA GCG GCC GGC ACT CGC GCC GCG ATC AAC ATG             1297
Phe Val Tyr Val Ala Ala Ala Ala Gly Thr Arg Ala Ala Ile Asn Met
                415                 420                 425

ACC GGC GGT GAC GCC GCC CTG AAC CTG ACC GCG ATG CCG GCC GTG GTG             1345
Thr Gly Gly Asp Ala Ala Leu Asn Leu Thr Ala Met Pro Ala Val Val
430                 435                 440

TTC ACC GAC CCG CAA GTG GCG ACC GTA GGC TAC AGC GAG GCG GAA GCG             1393
Phe Thr Asp Pro Gln Val Ala Thr Val Gly Tyr Ser Glu Ala Glu Ala
445                 450                 455                 460

CAC CAT GAC GGC ATC AAA ACT GAT AGT CGC ACG CTA ACG CTG GAC AAC             1441
His His Asp Gly Ile Lys Thr Asp Ser Arg Thr Leu Thr Leu Asp Asn
                465                 470                 475

GTG CCG CGC GCG CTC GCC AAC TTC GAC ACG CGC GGC TTC ATC AAA CTG             1489
Val Pro Arg Ala Leu Ala Asn Phe Asp Thr Arg Gly Phe Ile Lys Leu
                480                 485                 490

GTG GTT GAA GAA GGG AGC GGA CGA CTG ATC GGC GTC CAG GCA GTG GCC             1537
Val Val Glu Glu Gly Ser Gly Arg Leu Ile Gly Val Gln Ala Val Ala
                495                 500                 505

CCG GAA GCG GGC GAA CTG ATC CAG ACG GCC GCA CTG GCG ATT CGC AAC             1585
Pro Glu Ala Gly Glu Leu Ile Gln Thr Ala Ala Leu Ala Ile Arg Asn
510                 515                 520

CGG ATG ACG GTG CAG GAA CTG GCC GAC CAG TTG TTC CCC TAC CTG ACG             1633
Arg Met Thr Val Gln Glu Leu Ala Asp Gln Leu Phe Pro Tyr Leu Thr
525                 530                 535                 540

ATG GTC GAA GGG TTG AAG CTC GCG GCG CAG ACC TTC AAC AAG GAT GTG             1681
Met Val Glu Gly Leu Lys Leu Ala Ala Gln Thr Phe Asn Lys Asp Val
                545                 550                 555

AAG CAG CTT TCC TGC TGC GCC GGG TGA GGACAAGGAG GTGTGCGATG                   1728
Lys Gln Leu Ser Cys Cys Ala Gly *
                560                 565
```

SEQUENCE LISTING (1) GENERAL INFORMATION: 1

(i) APPLICANT: Meagher, Richard B.

Summers, Anne O.

Rugh, Clayton L.

(ii) TITLE OF INVENTION: Metal Resistance Sequences and
         Transgenic Plants (iii) NUMBER OF SEQUENCES: 34

(iv) CORRESPONDENCE ADDRESS:
         (A) ADDRESSEE: Greenlee, Winner and Sullivan, P.C.
         (B) STREET: 5370 Manhattan Circle, Suite 201          5370201
         (C) CITY: Boulder
         (D) STATE: Colorado
         (E) COUNTRY: US
         (F) ZIP: 80303                                        80303

(v) COMPUTER READABLE FORM:
         (A) MEDIUM TYPE: Floppy disk
         (B) COMPUTER: IBM PC compatible
         (C) OPERATING SYSTEM: PC-DOS/MS-DOS
         (D) SOFTWARE: PatentIn Release #1.0, Version #1.30    10130

(vi) CURRENT APPLICATION DATA:
         (A) APPLICATION NUMBER:US/08/878,957
         (B) FILING DATE: 19-JUN-1997                          191997
         (C) CLASSIFICATION:800

(vii) PRIOR APPLICATION DATA:
         (A) APPLICATION NUMBER: US 08/427,097                 08427097
         (B) FILING DATE: 21-APR-1995                          211995

(viii) ATTORNEY/AGENT INFORMATION:
         (A) NAME: Ferber, Donna M.
         (B) REGISTRATION NUMBER: 33,878                       33878
         (C) REFERENCE/DOCKET NUMBER: 40-94A                   4094

(ix) TELECOMMUNICATION INFORMATION:
         (A) TELEPHONE: (303) 499-8080                         3034998080
         (B) TELEFAX: (303) 499-8089                           3034998089
         (C) TELEX:

(2) INFORMATION FOR SEQ ID NO:1:

(i) SEQUENCE CHARACTERISTICS:
         (A) LENGTH: 1728 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (ix) FEATURE:
         (A) NAME/KEY: CDS
         (B) LOCATION: 14..1708

(xi) SEQUENCE DESCRIPTION: SEQ ID NO:1:

```
AAGGAACGAT GGT ATG AGC ACT CTC AAA ATC ACC GGC ATG ACT TGC GAC        49
            Met Ser Thr Leu Lys Ile Thr Gly Met Thr Cys Asp
              1               5                  10

TCG TGC GCA GTG CAT GTC AAG GAC GCC CTG GAG AAA GTG CCC GGC GTG       97
Ser Cys Ala Val His Val Lys Asp Ala Leu Glu Lys Val Pro Gly Val
         15                  20                  25

CAA TCA GCG GAT GTC TCC TAC GCC AAG GGC AGC GCC AAG CTC GCC ATT      145
Gln Ser Ala Asp Val Ser Tyr Ala Lys Gly Ser Ala Lys Leu Ala Ile
         30                  35                  40

GAG GTC GGC ACG TCA CCC GAC GCG CTG ACG GCC GCT GTA GCT GGA CTC      193
Glu Val Gly Thr Ser Pro Asp Ala Leu Thr Ala Ala Val Ala Gly Leu
 45                  50                  55                  60
```

```
GGT TAT CGG GCC ACG CTG GCC GAT GCC CCC TCA GTT TCG ACG CCG GGC         241
Gly Tyr Arg Ala Thr Leu Ala Asp Ala Pro Ser Val Ser Thr Pro Gly
                65                  70                  75

GGA TTG CTC GAC AAG ATG CGC GAT CTG CTG GGC AGA AAC GAC AAG ACG         289
Gly Leu Leu Asp Lys Met Arg Asp Leu Leu Gly Arg Asn Asp Lys Thr
            80                  85                  90

GGT AGC AGC GGC GCA TTG CAT ATC GCC GTC ATC GGC AGC GGC GGG GCC         337
Gly Ser Ser Gly Ala Leu His Ile Ala Val Ile Gly Ser Gly Gly Ala
            95                 100                 105

GCG ATG GCA GCG GCG CTG AAG GCC GTC GAG CAA GGC GCA CCT GTC ACG         385
Ala Met Ala Ala Ala Leu Lys Ala Val Glu Gln Gly Ala Pro Val Thr
    110                 115                 120

CTG ATC GAG CGC GGC ACC ATC GGC GGC ACC TGC GTC AAT GTC GGT TGT         433
Leu Ile Glu Arg Gly Thr Ile Gly Gly Thr Cys Val Asn Val Gly Cys
125                 130                 135                 140

GTG CCG TCC AAG ATC ATG ATC CGC GCC GCC CAT ATC GCC CAT CTG CGC         481
Val Pro Ser Lys Ile Met Ile Arg Ala Ala His Ile Ala His Leu Arg
                145                 150                 155

CGG GAA AGC CCG TTC GAT GGC GGC ATC GCC GCT ACC ACG CCG ACC ATC         529
Arg Glu Ser Pro Phe Asp Gly Gly Ile Ala Ala Thr Thr Pro Thr Ile
            160                 165                 170

CAG CGC ACG GCG CTG CTG GCC CAG CAG CAG GCC CGC GTC GAT GAA CTG         577
Gln Arg Thr Ala Leu Leu Ala Gln Gln Gln Ala Arg Val Asp Glu Leu
            175                 180                 185

CGC CAC GCC AAG TAC GAA GGC ATC TTG GAG GGC AAT CCG GCG ATC ACT         625
Arg His Ala Lys Tyr Glu Gly Ile Leu Glu Gly Asn Pro Ala Ile Thr
    190                 195                 200

GTG CTG CAC GGC TCC GCC CGC TTT AAG GAC AAT CGC AAC CTG ATC GTG         673
Val Leu His Gly Ser Ala Arg Phe Lys Asp Asn Arg Asn Leu Ile Val
205                 210                 215                 220

CAA CTC AAC GAC GGC GGC GAG CGC GTG GTG GCA TTC GAC CGC TGC CTG         721
Gln Leu Asn Asp Gly Gly Glu Arg Val Val Ala Phe Asp Arg Cys Leu
                225                 230                 235

ATC GCC ACC GGC GCG AGC CCG GCC GTG CCG CCG ATT CCC GGC CTG AAA         769
Ile Ala Thr Gly Ala Ser Pro Ala Val Pro Pro Ile Pro Gly Leu Lys
            240                 245                 250

GAC ACT CCG TAC TGG ACT TCC ACT GAA GCG CTG GTC AGC GAG ACG ATT         817
Asp Thr Pro Tyr Trp Thr Ser Thr Glu Ala Leu Val Ser Glu Thr Ile
            255                 260                 265

CCT AAG CGC CTG GCC GTG ATT GGC TCA TCA GTG CTG GCG CTG GAG CTG         865
Pro Lys Arg Leu Ala Val Ile Gly Ser Ser Val Leu Ala Leu Glu Leu
270                 275                 280

GCG CAG GCG TTC GCC CGA CTC GGA GCG AAG GTG ACG ATC CTG GCT CGC         913
Ala Gln Ala Phe Ala Arg Leu Gly Ala Lys Val Thr Ile Leu Ala Arg
285                 290                 295                 300

AGC ACG CTG TTC TTC CGC GAA GAC CCA GCT ATA GGC GAA GCT GTC ACG         961
Ser Thr Leu Phe Phe Arg Glu Asp Pro Ala Ile Gly Glu Ala Val Thr
                305                 310                 315

GCC GCA TTC CGG ATG GAG GGC ATC GAG GTG AGG GAA CAC ACC CAG GCC        1009
Ala Ala Phe Arg Met Glu Gly Ile Glu Val Arg Glu His Thr Gln Ala
            320                 325                 330

AGC CAG GTC GCG TAT ATC AAT GGT GAA GGG GAC GGC GAA TTC GTG CTC        1057
Ser Gln Val Ala Tyr Ile Asn Gly Glu Gly Asp Gly Glu Phe Val Leu
            335                 340                 345

ACC ACG GCG CAC GGC GAA CTG CGC GCC GAC AAG CTG CTG GTC GCC ACC        1105
Thr Thr Ala His Gly Glu Leu Arg Ala Asp Lys Leu Leu Val Ala Thr
350                 355                 360

GGC CGC GCG CCC AAC ACA CGC AAG CTG GCA CTG GAT GCG ACG GGC GTC        1153
Gly Arg Ala Pro Asn Thr Arg Lys Leu Ala Leu Asp Ala Thr Gly Val
365                 370                 375                 380
```

```
ACG CTC ACC CCC CAA GGC GCT ATC GTC ATC GAC CCC GGC ATG CGT ACA    1201
Thr Leu Thr Pro Gln Gly Ala Ile Val Ile Asp Pro Gly Met Arg Thr
            385                 390                 395

AGC GTG GAA CAC ATC TAC GCC GCA GGC GAC TGC ACC GAC CAG CCG CAG    1249
Ser Val Glu His Ile Tyr Ala Ala Gly Asp Cys Thr Asp Gln Pro Gln
                400                 405                 410

TTC GTC TAT GTG GCG GCA GCG GCC GGC ACT CGC GCC GCG ATC AAC ATG    1297
Phe Val Tyr Val Ala Ala Ala Ala Gly Thr Arg Ala Ala Ile Asn Met
                    415                 420                 425

ACC GGC GGT GAC GCC GCC CTG AAC CTG ACC GCG ATG CCG GCC GTG GTG    1345
Thr Gly Gly Asp Ala Ala Leu Asn Leu Thr Ala Met Pro Ala Val Val
            430                 435                 440

TTC ACC GAC CCG CAA GTG GCG ACC GTA GGC TAC AGC GAG GCG GAA GCG    1393
Phe Thr Asp Pro Gln Val Ala Thr Val Gly Tyr Ser Glu Ala Glu Ala
445                 450                 455                 460

CAC CAT GAC GGC ATC AAA ACT GAT AGT CGC ACG CTA ACG CTG GAC AAC    1441
His His Asp Gly Ile Lys Thr Asp Ser Arg Thr Leu Thr Leu Asp Asn
                    465                 470                 475

GTG CCG CGC GCG CTC GCC AAC TTC GAC ACG CGC GGC TTC ATC AAA CTG    1489
Val Pro Arg Ala Leu Ala Asn Phe Asp Thr Arg Gly Phe Ile Lys Leu
            480                 485                 490

GTG GTT GAA GAA GGG AGC GGA CGA CTG ATC GGC GTC CAG GCA GTG GCC    1537
Val Val Glu Glu Gly Ser Gly Arg Leu Ile Gly Val Gln Ala Val Ala
                495                 500                 505

CCG GAA GCG GGC GAA CTG ATC CAG ACG GCC GCA CTG GCG ATT CGC AAC    1585
Pro Glu Ala Gly Glu Leu Ile Gln Thr Ala Ala Leu Ala Ile Arg Asn
            510                 515                 520

CGG ATG ACG GTG CAG GAA CTG GCC GAC CAG TTG TTC CCC TAC CTG ACG    1633
Arg Met Thr Val Gln Glu Leu Ala Asp Gln Leu Phe Pro Tyr Leu Thr
525                 530                 535                 540

ATG GTC GAA GGG TTG AAG CTC GCG GCG CAG ACC TTC AAC AAG GAT GTG    1681
Met Val Glu Gly Leu Lys Leu Ala Ala Gln Thr Phe Asn Lys Asp Val
                    545                 550                 555

AAG CAG CTT TCC TGC TGC GCC GGG TGA GGACAAGGAG GTGTGCGATG          1728
Lys Gln Leu Ser Cys Cys Ala Gly  *
                560             565

(2) INFORMATION FOR SEQ ID NO:2:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Thr Leu Lys Ile Thr Gly Met Thr Cys Asp Ser Cys Ala Val
1               5                   10                  15

His Val Lys Asp Ala Leu Glu Lys Val Pro Gly Val Gln Ser Ala Asp
                20                  25                  30

Val Ser Tyr Ala Lys Gly Ser Ala Lys Leu Ala Ile Glu Val Gly Thr
            35                  40                  45

Ser Pro Asp Ala Leu Thr Ala Ala Val Ala Gly Leu Gly Tyr Arg Ala
        50                  55                  60

Thr Leu Ala Asp Ala Pro Ser Val Ser Thr Pro Gly Gly Leu Leu Asp
65                  70                  75                  80

Lys Met Arg Asp Leu Leu Gly Arg Asn Asp Lys Thr Gly Ser Ser Gly
                85                  90                  95

Ala Leu His Ile Ala Val Ile Gly Ser Gly Gly Ala Ala Met Ala Ala
```

```
                    100                 105                 110
Ala Leu Lys Ala Val Glu Gln Gly Ala Pro Val Thr Leu Ile Glu Arg
            115                 120                 125
Gly Thr Ile Gly Gly Thr Cys Val Asn Val Gly Cys Val Pro Ser Lys
130                 135                 140
Ile Met Ile Arg Ala Ala His Ile Ala His Leu Arg Arg Glu Ser Pro
145                 150                 155                 160
Phe Asp Gly Gly Ile Ala Ala Thr Thr Pro Thr Ile Gln Arg Thr Ala
                165                 170                 175
Leu Leu Ala Gln Gln Ala Arg Val Asp Glu Leu Arg His Ala Lys
            180                 185                 190
Tyr Glu Gly Ile Leu Glu Gly Asn Pro Ala Ile Thr Val Leu His Gly
            195                 200                 205
Ser Ala Arg Phe Lys Asp Asn Arg Asn Leu Ile Val Gln Leu Asn Asp
210                 215                 220
Gly Gly Glu Arg Val Val Ala Phe Asp Arg Cys Leu Ile Ala Thr Gly
225                 230                 235                 240
Ala Ser Pro Ala Val Pro Pro Ile Pro Gly Leu Lys Asp Thr Pro Tyr
                245                 250                 255
Trp Thr Ser Thr Glu Ala Leu Val Ser Glu Thr Ile Pro Lys Arg Leu
            260                 265                 270
Ala Val Ile Gly Ser Ser Val Leu Ala Leu Glu Leu Ala Gln Ala Phe
            275                 280                 285
Ala Arg Leu Gly Ala Lys Val Thr Ile Leu Ala Arg Ser Thr Leu Phe
            290                 295                 300
Phe Arg Glu Asp Pro Ala Ile Gly Glu Ala Val Thr Ala Ala Phe Arg
305                 310                 315                 320
Met Glu Gly Ile Glu Val Arg Glu His Thr Gln Ala Ser Gln Val Ala
                325                 330                 335
Tyr Ile Asn Gly Glu Gly Asp Gly Glu Phe Val Leu Thr Thr Ala His
            340                 345                 350
Gly Glu Leu Arg Ala Asp Lys Leu Leu Val Ala Thr Gly Arg Ala Pro
            355                 360                 365
Asn Thr Arg Lys Leu Ala Leu Asp Ala Thr Gly Val Thr Leu Thr Pro
370                 375                 380
Gln Gly Ala Ile Val Ile Asp Pro Gly Met Arg Thr Ser Val Glu His
385                 390                 395                 400
Ile Tyr Ala Ala Gly Asp Cys Thr Asp Gln Pro Gln Phe Val Tyr Val
                405                 410                 415
Ala Ala Ala Ala Gly Thr Arg Ala Ala Ile Asn Met Thr Gly Gly Asp
            420                 425                 430
Ala Ala Leu Asn Leu Thr Ala Met Pro Ala Val Val Phe Thr Asp Pro
            435                 440                 445
Gln Val Ala Thr Val Gly Tyr Ser Glu Ala Glu Ala His His Asp Gly
            450                 455                 460
Ile Lys Thr Asp Ser Arg Thr Leu Thr Leu Asp Asn Val Pro Arg Ala
465                 470                 475                 480
Leu Ala Asn Phe Asp Thr Arg Gly Phe Ile Lys Leu Val Val Glu Glu
                485                 490                 495
Gly Ser Gly Arg Leu Ile Gly Val Gln Ala Val Ala Pro Glu Ala Gly
            500                 505                 510
Glu Leu Ile Gln Thr Ala Ala Leu Ala Ile Arg Asn Arg Met Thr Val
            515                 520                 525
```

```
Gln Glu Leu Ala Asp Gln Leu Phe Pro Tyr Leu Thr Met Val Glu Gly
    530                 535                 540

Leu Lys Leu Ala Ala Gln Thr Phe Asn Lys Asp Val Lys Gln Leu Ser
545                 550                 555                 560

Cys Cys Ala Gly
```

(2) INFORMATION FOR SEQ ID NO:3:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:3:

```
CTAGAACTAG TGGATCCCTA GATCTAAGAA GGAACCACAA TGAGCACTCT CAAAATCAC        59
```

(2) INFORMATION FOR SEQ ID NO:4:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO:4:

```
CCTATAGCTG GGTCTTCACG AAAGAAGAGA GTGGAGCGTG CAAGAATGGT CACTTTAGCA        60

CCAAGACGTG CAAAGGCCTG CGCCAGCTCC AG                                      92
```

(2) INFORMATION FOR SEQ ID NO:5:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (iv) ANTI-SENSE: NO (xi) SEQUENCE DESCRIPTION: SEQ ID NO:5:

```
GAAGACCCAG CTATAGGTGA AGCTGTTACT GCTGCATTTC GCATGGAAGG CATTGAAGTG        60

CGTGAGCATA CTCAAGCAAG CCAAGTTGCC TATATCAAT                              99
```

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Olgionucleotide"

(iii) HYPOTHETICAL: NO (xi) SEQUENCE DESCRIPTION: SEQ ID NO:6:

TATCGAATTC CTGCAGCCTC ACCCGGCGCA GCAGGA                                36

(2) INFORMATION FOR SEQ ID NO:7:

(i) SEQUENCE CHARACTERISTICS:
            (A) LENGTH: 101 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (xi) SEQUENCE DESCRIPTION: SEQ ID NO:7:

GCTTCAGTGG AAGTCCAGTA AGGAGTGTCC TTGAGACCAG GAATTGGTGG AACAGCTGGG       60

CTTGCACCAG TGGCAATGAG ACAGCGGTCG AATGCCACCA C                         101

(2) INFORMATION FOR SEQ ID NO:8:

(i) SEQUENCE CHARACTERISTICS:
            (A) LENGTH: 109 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (iv) ANTI-SENSE: NO (xi) SEQUENCE DESCRIPTION: SEQ ID NO:8:

TGGACTTCCA CTGAAGCACT AGTGTCTGAG ACCATTCCAA AGCGTCTTGC AGTCATTGGC       60

TCCTCTGTGG TGGCTCTTGA ACTTGCCCAG GCCTTTGCAC GTCTTGGTG                 109

(2) INFORMATION FOR SEQ ID NO:9:

(i) SEQUENCE CHARACTERISTICS:
            (A) LENGTH: 99 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide"

(iii) HYPOTHETICAL: NO (xi) SEQUENCE DESCRIPTION: SEQ ID NO:9:

GTGCAGAGCC ATGAAGCACA GTGATGGCTG GGTTACCTTC TAGAATACCT TCATACTTTG       60

CATGACGAAG TTCATCAACA CGGGCCTGCT GCTGGGCCA                             99

(2) INFORMATION FOR SEQ ID NO:10:

(i) SEQUENCE CHARACTERISTICS:
            (A) LENGTH: 99 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Olgionucleotide"

(iii) HYPOTHETICAL: NO (iv) ANTI-SENSE: NO (xi) SEQUENCE DESCRIPTION: SEQ ID NO:10:

GCTTCATGGC TCTGCACGTT TCAAGGACAA CCGTAACCTC ATTGTTCAAC TTAATGATGG        60

TGGTGAACGT GTGGTGGCTT TTGACCGCTG TCTCATTGC                              99

(2) INFORMATION FOR SEQ ID NO:11:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO:11:

CACGACCAGT TGCAACAAGG AGTTTGTCTG CACGAAGTTC ACCATGAGCA GTGGTAAGGA        60

CGAATTCACC ATCACCTTCA CCATTGATAT AGGCAACTTG                            100

(2) INFORMATION FOR SEQ ID NO:12:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (iv) ANTI-SENSE: NO (xi) SEQUENCE DESCRIPTION: SEQ ID NO:12:

TGTTGCAACT GGTCGTGCAC CAAACACTCG CAAACTGGCA CTTGATGCAA CTGGTGTGAC        60

CCTTACTCCA CAAGGTGCTA TTGTCATCGA CCCCGGCAT                              99

(2) INFORMATION FOR SEQ ID NO:13:

(i) SEQUENCE CHARACTERISTICS:
        (A) LENGTH: 1752 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc = "Mutagenized merApe38"

(iii) HYPOTHETICAL: NO (ix) FEATURE:
        (A) NAME/KEY: CDS
        (B) LOCATION: 40..1734

(ix) FEATURE:
        (A) NAME/KEY: mat_peptide
        (B) LOCATION: 40..1731

(xi) SEQUENCE DESCRIPTION: SEQ ID NO:13:

CTAGAACTAG TGGATCCCTA GATCTAAGAA GGAACCACA ATG AGC ACT CTC AAA          54
                                            Met Ser Thr Leu Lys
                                             1               5

```
ATC ACC GGC ATG ACT TGC GAC TCG TGC GCA GTG CAT GTC AAG GAC GCC      102
Ile Thr Gly Met Thr Cys Asp Ser Cys Ala Val His Val Lys Asp Ala
         10                  15                  20

CTG GAG AAA GTG CCC GGC GTG CAA TCA GCG GAT GTC TCC TAC GCC AAG      150
Leu Glu Lys Val Pro Gly Val Gln Ser Ala Asp Val Ser Tyr Ala Lys
             25                  30                  35

GGC AGC GCC AAG CTC GCC ATT GAG GTC GGC ACG TCA CCC GAC GCG CTG      198
Gly Ser Ala Lys Leu Ala Ile Glu Val Gly Thr Ser Pro Asp Ala Leu
                 40                  45                  50

ACG GCC GCT GTA GCT GGA CTC GGT TAT CGG GCC ACG CTG GCC GAT GCC      246
Thr Ala Ala Val Ala Gly Leu Gly Tyr Arg Ala Thr Leu Ala Asp Ala
                     55                  60                  65

CCC TCA GTT TCG ACG CCG GGC GGA TTG CTC GAC AAG ATG CGC GAT CTG      294
Pro Ser Val Ser Thr Pro Gly Gly Leu Leu Asp Lys Met Arg Asp Leu
 70                  75                  80                  85

CTG GGC AGA AAC GAC AAG ACG GGT AGC AGC GGC GCA TTG CAT ATC GCC      342
Leu Gly Arg Asn Asp Lys Thr Gly Ser Ser Gly Ala Leu His Ile Ala
                         90                  95                 100

GTC ATC GGC AGC GGC GGG GCC GCG ATG GCA GCG GCG CTG AAG GCC GTC      390
Val Ile Gly Ser Gly Gly Ala Ala Met Ala Ala Ala Leu Lys Ala Val
                            105                 110                 115

GAG CAA GGC GCA CCT GTC ACG CTG ATC GAG CGC GGC ACC ATC GGC GGC      438
Glu Gln Gly Ala Pro Val Thr Leu Ile Glu Arg Gly Thr Ile Gly Gly
                120                 125                 130

ACC TGC GTC AAT GTC GGT TGT GTG CCG TCC AAG ATC ATG ATC CGC GCC      486
Thr Cys Val Asn Val Gly Cys Val Pro Ser Lys Ile Met Ile Arg Ala
    135                 140                 145

GCC CAT ATC GCC CAT CTG CGC CGG GAA AGC CCG TTC GAT GGC GGC ATC      534
Ala His Ile Ala His Leu Arg Arg Glu Ser Pro Phe Asp Gly Gly Ile
150                 155                 160                 165

GCC GCT ACC ACG CCG ACC ATC CAG CGC ACG GCG CTG CTG GCC CAG CAG      582
Ala Ala Thr Thr Pro Thr Ile Gln Arg Thr Ala Leu Leu Ala Gln Gln
                170                 175                 180

CAG GCC CGC GTC GAT GAA CTG CGT CAT GCA AAG TAT GAA GGT ATT CTA      630
Gln Ala Arg Val Asp Glu Leu Arg His Ala Lys Tyr Glu Gly Ile Leu
            185                 190                 195

GAA GGT AAC CCA GCC ATC ACT GTG CTT CAT GGC TCT GCA CGT TTC AAG      678
Glu Gly Asn Pro Ala Ile Thr Val Leu His Gly Ser Ala Arg Phe Lys
        200                 205                 210

GAC AAC CGT AAC CTC ATT GTT CAA CTC AAC GAC GGC GGC GAG CGC GTG      726
Asp Asn Arg Asn Leu Ile Val Gln Leu Asn Asp Gly Gly Glu Arg Val
    215                 220                 225

GTG GCA TTC GAC CGC TGT CTC ATT GCC ACT GGT GCA AGC CCA GCT GTT      774
Val Ala Phe Asp Arg Cys Leu Ile Ala Thr Gly Ala Ser Pro Ala Val
230                 235                 240                 245

CCA CCA ATT CCT GGT CTC AAG GAC ACT CCT TAC TGG ACT TCC ACT GAA      822
Pro Pro Ile Pro Gly Leu Lys Asp Thr Pro Tyr Trp Thr Ser Thr Glu
                250                 255                 260

GCA CTA GTG TCT GAG ACC ATT CCA AAG CGT CTT GCA GTC ATT GGC TCC      870
Ala Leu Val Ser Glu Thr Ile Pro Lys Arg Leu Ala Val Ile Gly Ser
            265                 270                 275

TCT GTG GTG GCT CTT GAA CTT GCC CAG GCC TTT GCA CGT CTT GGT GCT      918
Ser Val Val Ala Leu Glu Leu Ala Gln Ala Phe Ala Arg Leu Gly Ala
        280                 285                 290

AAA GTG ACC ATT CTT GCA CGC TCC ACT CTC TTC TTT CGT GAA GAC CCA      966
Lys Val Thr Ile Leu Ala Arg Ser Thr Leu Phe Phe Arg Glu Asp Pro
    295                 300                 305

GCT ATA GGT GAA GCT GTT ACT GCT GCA TTT CGC ATG GAA GGC ATT GAA     1014
Ala Ile Gly Glu Ala Val Thr Ala Ala Phe Arg Met Glu Gly Ile Glu
310                 315                 320                 325
```

```
GTG CGT GAG CAT ACT CAA GCA AGC CAA GTT GCC TAT ATC AAT GGT GAA     1062
Val Arg Glu His Thr Gln Ala Ser Gln Val Ala Tyr Ile Asn Gly Glu
            330                 335                 340

GGT GAC GGT GAA TTC GTC CTA ACC ACT GCT CAT GGT GAA CTT CGT GCA     1110
Gly Asp Gly Glu Phe Val Leu Thr Thr Ala His Gly Glu Leu Arg Ala
                345                 350                 355

GAC AAA CTC CTT GTT GCA ACT GGT CGT GCA CCA AAC ACT CGC AAA CTG     1158
Asp Lys Leu Leu Val Ala Thr Gly Arg Ala Pro Asn Thr Arg Lys Leu
        360                 365                 370

GCA CTT GAT GCA ACT GGT GTG ACC CTT ACT CCA CAA GGT GCT ATT GTC     1206
Ala Leu Asp Ala Thr Gly Val Thr Leu Thr Pro Gln Gly Ala Ile Val
    375                 380                 385

ATC GAC CCC GGC ATG CGT ACA AGC GTG GAA CAC ATC TAC GCC GCA GGC     1254
Ile Asp Pro Gly Met Arg Thr Ser Val Glu His Ile Tyr Ala Ala Gly
390                 395                 400                 405

GAC TGC ACC GAC CAG CCG CAG TTC GTC TAT GTG GCG GCA GCG GCC GGC     1302
Asp Cys Thr Asp Gln Pro Gln Phe Val Tyr Val Ala Ala Ala Ala Gly
                410                 415                 420

ACT CGC GCC GCG ATC AAC ATG ACC GGC GGT GAC GCC GCC CTG AAC CTG     1350
Thr Arg Ala Ala Ile Asn Met Thr Gly Gly Asp Ala Ala Leu Asn Leu
        425                 430                 435

ACC GCG ATG CCG GCC GTG GTG TTC ACC GAC CCG CAA GTG GCG ACC GTA     1398
Thr Ala Met Pro Ala Val Val Phe Thr Asp Pro Gln Val Ala Thr Val
    440                 445                 450

GGC TAC AGC GAG GCG GAA GCG CAC CAT GAC GGC ATC AAA ACT GAT AGT     1446
Gly Tyr Ser Glu Ala Glu Ala His His Asp Gly Ile Lys Thr Asp Ser
455                 460                 465

CGC ACG CTA ACG CTG GAC AAC GTG CCG CGC GCG CTC GCC AAC TTC GAC     1494
Arg Thr Leu Thr Leu Asp Asn Val Pro Arg Ala Leu Ala Asn Phe Asp
470                 475                 480                 485

ACG CGC GGC TTC ATC AAA CTG GTG GTT GAA GAA GGG AGC GGA CGA CTG     1542
Thr Arg Gly Phe Ile Lys Leu Val Val Glu Glu Gly Ser Gly Arg Leu
                490                 495                 500

ATC GGC GTC CAG GCA GTG GCC CCG GAA GCG GGC GAA CTG ATC CAG ACG     1590
Ile Gly Val Gln Ala Val Ala Pro Glu Ala Gly Glu Leu Ile Gln Thr
        505                 510                 515

GCC GCA CTG GCG ATT CGC AAC CGG ATG ACG GTG CAG GAA CTG GCC GAC     1638
Ala Ala Leu Ala Ile Arg Asn Arg Met Thr Val Gln Glu Leu Ala Asp
    520                 525                 530

CAG TTG TTC CCC TAC CTG ACG ATG GTC GAA GGG TTG AAG CTC GCG GCG     1686
Gln Leu Phe Pro Tyr Leu Thr Met Val Glu Gly Leu Lys Leu Ala Ala
535                 540                 545

CAG ACC TTC AAC AAG GAT GTG AAG CAG CTT TCC TGC TGC GCC GGG TGA     1734
Gln Thr Phe Asn Lys Asp Val Lys Gln Leu Ser Cys Cys Ala Gly  *
                555                 560                 565
550

GGCTGCAGGA ATTCGATA                                                 1752
```

(2) INFORMATION FOR SEQ ID NO:14:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:14:

```
Met Ser Thr Leu Lys Ile Thr Gly Met Thr Cys Asp Ser Cys Ala Val
 1               5                  10                  15

His Val Lys Asp Ala Leu Glu Lys Val Pro Gly Val Gln Ser Ala Asp
            20                  25                  30
```

```
Val Ser Tyr Ala Lys Gly Ser Ala Lys Leu Ala Ile Glu Val Gly Thr
         35                  40                  45

Ser Pro Asp Ala Leu Thr Ala Ala Val Ala Gly Leu Gly Tyr Arg Ala
 50                  55                  60

Thr Leu Ala Asp Ala Pro Ser Val Ser Thr Pro Gly Gly Leu Leu Asp
 65                  70                  75                  80

Lys Met Arg Asp Leu Leu Gly Arg Asn Asp Lys Thr Gly Ser Ser Gly
                 85                  90                  95

Ala Leu His Ile Ala Val Ile Gly Ser Gly Ala Ala Met Ala Ala
                100                 105                 110

Ala Leu Lys Ala Val Glu Gln Gly Ala Pro Val Thr Leu Ile Glu Arg
            115                 120                 125

Gly Thr Ile Gly Thr Cys Val Asn Val Gly Cys Val Pro Ser Lys
        130                 135                 140

Ile Met Ile Arg Ala Ala His Ile Ala His Leu Arg Arg Glu Ser Pro
145                 150                 155                 160

Phe Asp Gly Gly Ile Ala Ala Thr Thr Pro Thr Ile Gln Arg Thr Ala
                165                 170                 175

Leu Leu Ala Gln Gln Ala Arg Val Asp Glu Leu Arg His Ala Lys
                180                 185                 190

Tyr Glu Gly Ile Leu Glu Gly Asn Pro Ala Ile Thr Val Leu His Gly
            195                 200                 205

Ser Ala Arg Phe Lys Asp Asn Arg Asn Leu Ile Val Gln Leu Asn Asp
210                 215                 220

Gly Gly Glu Arg Val Val Ala Phe Asp Arg Cys Leu Ile Ala Thr Gly
225                 230                 235                 240

Ala Ser Pro Ala Val Pro Pro Ile Pro Gly Leu Lys Asp Thr Pro Tyr
                245                 250                 255

Trp Thr Ser Thr Glu Ala Leu Val Ser Glu Thr Ile Pro Lys Arg Leu
                260                 265                 270

Ala Val Ile Gly Ser Ser Val Val Ala Leu Glu Leu Ala Gln Ala Phe
            275                 280                 285

Ala Arg Leu Gly Ala Lys Val Thr Ile Leu Ala Arg Ser Thr Leu Phe
            290                 295                 300

Phe Arg Glu Asp Pro Ala Ile Gly Glu Ala Val Thr Ala Ala Phe Arg
305                 310                 315                 320

Met Glu Gly Ile Glu Val Arg Glu His Thr Gln Ala Ser Gln Val Ala
                325                 330                 335

Tyr Ile Asn Gly Glu Gly Asp Gly Glu Phe Val Leu Thr Thr Ala His
                340                 345                 350

Gly Glu Leu Arg Ala Asp Lys Leu Leu Val Ala Thr Gly Arg Ala Pro
            355                 360                 365

Asn Thr Arg Lys Leu Ala Leu Asp Ala Thr Gly Val Thr Leu Thr Pro
370                 375                 380

Gln Gly Ala Ile Val Ile Asp Pro Gly Met Arg Thr Ser Val Glu His
385                 390                 395                 400

Ile Tyr Ala Ala Gly Asp Cys Thr Asp Gln Pro Gln Phe Val Tyr Val
                405                 410                 415

Ala Ala Ala Ala Gly Thr Arg Ala Ala Ile Asn Met Thr Gly Gly Asp
                420                 425                 430

Ala Ala Leu Asn Leu Thr Ala Met Pro Ala Val Val Phe Thr Asp Pro
            435                 440                 445

Gln Val Ala Thr Val Gly Tyr Ser Glu Ala Glu Ala His His Asp Gly
450                 455                 460
```

```
Ile Lys Thr Asp Ser Arg Thr Leu Thr Leu Asp Asn Val Pro Arg Ala
465                 470                 475                 480

Leu Ala Asn Phe Asp Thr Arg Gly Phe Ile Lys Leu Val Val Glu Glu
                485                 490                 495

Gly Ser Gly Arg Leu Ile Gly Val Gln Ala Val Ala Pro Glu Ala Gly
            500                 505                 510

Glu Leu Ile Gln Thr Ala Ala Leu Ala Ile Arg Asn Arg Met Thr Val
            515                 520                 525

Gln Glu Leu Ala Asp Gln Leu Phe Pro Tyr Leu Thr Met Val Glu Gly
    530                 535                 540

Leu Lys Leu Ala Ala Gln Thr Phe Asn Lys Asp Val Lys Gln Leu Ser
545                 550                 555                 560

Cys Cys Ala Gly (2) INFORMATION FOR SEQ ID NO:15:

(i) SEQUENCE CHARACTERISTICS:
        (A) LENGTH: 1752 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc = "Mutagenized merApe9"

(iii) HYPOTHETICAL: NO (ix) FEATURE:
        (A) NAME/KEY: CDS
        (B) LOCATION: 40..1734

(ix) FEATURE:
        (A) NAME/KEY: mat_peptide
        (B) LOCATION: 40..1731

(xi) SEQUENCE DESCRIPTION: SEQ ID NO:15:

CTAGAACTAG TGGATCCCTA GATCTAAGAA GGAACCACA ATG AGC ACT CTC AAA         54
                                           Met Ser Thr Leu Lys
                                             1               5

ATC ACC GGC ATG ACT TGC GAC TCG TGC GCA GTG CAT GTC AAG GAC GCC       102
Ile Thr Gly Met Thr Cys Asp Ser Cys Ala Val His Val Lys Asp Ala
             10                  15                  20

CTG GAG AAA GTG CCC GGC GTG CAA TCA GCG GAT GTC TCC TAC GCC AAG       150
Leu Glu Lys Val Pro Gly Val Gln Ser Ala Asp Val Ser Tyr Ala Lys
         25                  30                  35

GGC AGC GCC AAG CTC GCC ATT GAG GTC GGC ACG TCA CCC GAC GCG CTG       198
Gly Ser Ala Lys Leu Ala Ile Glu Val Gly Thr Ser Pro Asp Ala Leu
     40                  45                  50

ACG GCC GCT GTA GCT GGA CTC GGT TAT CGG GCC ACG CTG GCC GAT GCC       246
Thr Ala Ala Val Ala Gly Leu Gly Tyr Arg Ala Thr Leu Ala Asp Ala
 55                  60                  65

CCC TCA GTT TCG ACG CCG GGC GGA TTG CTC GAC AAG ATG CGC GAT CTG       294
Pro Ser Val Ser Thr Pro Gly Gly Leu Leu Asp Lys Met Arg Asp Leu
 70                  75                  80                  85

CTG GGC AGA AAC GAC AAG ACG GGT AGC AGC GGC GCA TTG CAT ATC GCC       342
Leu Gly Arg Asn Asp Lys Thr Gly Ser Ser Gly Ala Leu His Ile Ala
             90                  95                 100

GTC ATC GGC AGC GGC GGG GCC GCG ATG GCA GCG GCG CTG AAG GCC GTC       390
Val Ile Gly Ser Gly Gly Ala Ala Met Ala Ala Ala Leu Lys Ala Val
            105                 110                 115

GAG CAA GGC GCA CCT GTC ACG CTG ATC GAG CGC GGC ACC ATC GGC GGC       438
Glu Gln Gly Ala Pro Val Thr Leu Ile Glu Arg Gly Thr Ile Gly Gly
        120                 125                 130
```

```
ACC TGC GTC AAT GTC GGT TGT GTG CCG TCC AAG ATC ATG ATC CGC GCC         486
Thr Cys Val Asn Val Gly Cys Val Pro Ser Lys Ile Met Ile Arg Ala
    135                 140                 145

GCC CAT ATC GCC CAT CTG CGC CGG GAA AGC CCG TTC GAT GGC GGC ATC         534
Ala His Ile Ala His Leu Arg Arg Glu Ser Pro Phe Asp Gly Gly Ile
150                 155                 160                 165

GCC GCT ACC ACG CCG ACC ATC CAG CGC ACG GCG CTG CTG GCC CAG CAG         582
Ala Ala Thr Thr Pro Thr Ile Gln Arg Thr Ala Leu Leu Ala Gln Gln
                170                 175                 180

CAG GCC CGC GTC GAT GAA CTG CGC CAC GCC AAG TAC GAA GGC ATC TTG         630
Gln Ala Arg Val Asp Glu Leu Arg His Ala Lys Tyr Glu Gly Ile Leu
            185                 190                 195

GAG GGC AAT CCG GCG ATC ACT GTG CTG CAC GGC TCC GCC CGC TTT AAG         678
Glu Gly Asn Pro Ala Ile Thr Val Leu His Gly Ser Ala Arg Phe Lys
        200                 205                 210

GAC AAT CGC AAC CTG ATC GTG CAA CTC AAC GAC GGC GGC GAG CGC GTG         726
Asp Asn Arg Asn Leu Ile Val Gln Leu Asn Asp Gly Gly Glu Arg Val
    215                 220                 225

GTG GCA TTC GAC CGC TGC CTG ATC GCC ACC GGC GCG AGC CCG GCC GTG         774
Val Ala Phe Asp Arg Cys Leu Ile Ala Thr Gly Ala Ser Pro Ala Val
230                 235                 240                 245

CCG CCG ATT CCC GGC CTG AAA GAC ACT CCG TAC TGG ACT TCC ACT GAA         822
Pro Pro Ile Pro Gly Leu Lys Asp Thr Pro Tyr Trp Thr Ser Thr Glu
                250                 255                 260

GCG CTG GTC AGC GAG ACG ATT CCT AAG CGC CTG GCC GTG ATT GGC TCA         870
Ala Leu Val Ser Glu Thr Ile Pro Lys Arg Leu Ala Val Ile Gly Ser
            265                 270                 275

TCA GTG CTG GCG CTT GAA CTT GCC CAG GCC TTT GCA CGT CTT GGT GCT         918
Ser Val Leu Ala Leu Glu Leu Ala Gln Ala Phe Ala Arg Leu Gly Ala
        280                 285                 290

AAA GTG ACC ATT CTT GCA CGC TCC ACT CTC TTC TTT CGT GAA GAC CCA         966
Lys Val Thr Ile Leu Ala Arg Ser Thr Leu Phe Phe Arg Glu Asp Pro
    295                 300                 305

GCT ATA GGT GAA GCT GTT ACT GCT GCA TTT CGC ATG GAA GGC ATT GAA        1014
Ala Ile Gly Glu Ala Val Thr Ala Ala Phe Arg Met Glu Gly Ile Glu
310                 315                 320                 325

GTG CGT GAG CAT ACT CAA GCA AGC CAA GTT GCC TAT ATC AAT GGT GAA        1062
Val Arg Glu His Thr Gln Ala Ser Gln Val Ala Tyr Ile Asn Gly Glu
                330                 335                 340

GGG GAC GGC GAA TTC GTG CTC ACC ACG GCG CAC GGC GAA CTG CGC GCC        1110
Gly Asp Gly Glu Phe Val Leu Thr Thr Ala His Gly Glu Leu Arg Ala
            345                 350                 355

GAC AAG CTG CTG GTC GCC ACC GGC CGC GCG CCC AAC ACA CGC AAG CTG        1158
Asp Lys Leu Leu Val Ala Thr Gly Arg Ala Pro Asn Thr Arg Lys Leu
        360                 365                 370

GCA CTG GAT GCG ACG GGC GTC ACG CTC ACC CCC CAA GGC GCT ATC GTC        1206
Ala Leu Asp Ala Thr Gly Val Thr Leu Thr Pro Gln Gly Ala Ile Val
    375                 380                 385

ATC GAC CCC GGC ATG CGT ACA AGC GTG GAA CAC ATC TAC GCC GCA GGC        1254
Ile Asp Pro Gly Met Arg Thr Ser Val Glu His Ile Tyr Ala Ala Gly
390                 395                 400                 405

GAC TGC ACC GAC CAG CCG CAG TTC GTC TAT GTG GCG GCA GCG GCC GGC        1302
Asp Cys Thr Asp Gln Pro Gln Phe Val Tyr Val Ala Ala Ala Ala Gly
                410                 415                 420

ACT CGC GCC GCG ATC AAC ATG ACC GGC GGT GAC GCC GCC CTG AAC CTG        1350
Thr Arg Ala Ala Ile Asn Met Thr Gly Gly Asp Ala Ala Leu Asn Leu
            425                 430                 435

ACC GCG ATG CCG GCC GTG GTG TTC ACC GAC CCG CAA GTG GCG ACC GTA        1398
Thr Ala Met Pro Ala Val Val Phe Thr Asp Pro Gln Val Ala Thr Val
        440                 445                 450
```

```
GGC TAC AGC GAG GCG GAA GCG CAC CAT GAC GGC ATC AAA ACT GAT AGT      1446
Gly Tyr Ser Glu Ala Glu Ala His His Asp Gly Ile Lys Thr Asp Ser
    455                 460                 465

CGC ACG CTA ACG CTG GAC AAC GTG CCG CGC GCG CTC GCC AAC TTC GAC      1494
Arg Thr Leu Thr Leu Asp Asn Val Pro Arg Ala Leu Ala Asn Phe Asp
470                 475                 480                 485

ACG CGC GGC TTC ATC AAA CTG GTG GTT GAA GAA GGG AGC GGA CGA CTG      1542
Thr Arg Gly Phe Ile Lys Leu Val Val Glu Glu Gly Ser Gly Arg Leu
                    490                 495                 500

ATC GGC GTC CAG GCA GTG GCC CCG GAA GCG GGC GAA CTG ATC CAG ACG      1590
Ile Gly Val Gln Ala Val Ala Pro Glu Ala Gly Glu Leu Ile Gln Thr
                505                 510                 515

GCC GCA CTG GCG ATT CGC AAC CGG ATG ACG GTG CAG GAA CTG GCC GAC      1638
Ala Ala Leu Ala Ile Arg Asn Arg Met Thr Val Gln Glu Leu Ala Asp
            520                 525                 530

CAG TTG TTC CCC TAC CTG ACG ATG GTC GAA GGG TTG AAG CTC GCG GCG      1686
Gln Leu Phe Pro Tyr Leu Thr Met Val Glu Gly Leu Lys Leu Ala Ala
        535                 540                 545

CAG ACC TTC AAC AAG GAT GTG AAG CAG CTT TCC TGC TGC GCC GGG TGA      1734
Gln Thr Phe Asn Lys Asp Val Lys Gln Leu Ser Cys Cys Ala Gly  *
550                 555                 560                 565

GGCTGCAGGA ATTCGATA                                                  1752
```

(2) INFORMATION FOR SEQ ID NO:16:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:16:

```
Met Ser Thr Leu Lys Ile Thr Gly Met Thr Cys Asp Ser Cys Ala Val
1               5                   10                  15

His Val Lys Asp Ala Leu Glu Lys Val Pro Gly Val Gln Ser Ala Asp
            20                  25                  30

Val Ser Tyr Ala Lys Gly Ser Ala Lys Leu Ala Ile Glu Val Gly Thr
        35                  40                  45

Ser Pro Asp Ala Leu Thr Ala Ala Val Ala Gly Leu Gly Tyr Arg Ala
    50                  55                  60

Thr Leu Ala Asp Ala Pro Ser Val Ser Thr Pro Gly Gly Leu Leu Asp
65                  70                  75                  80

Lys Met Arg Asp Leu Leu Gly Arg Asn Asp Lys Thr Gly Ser Ser Gly
                85                  90                  95

Ala Leu His Ile Ala Val Ile Gly Ser Gly Ala Ala Met Ala Ala
            100                 105                 110

Ala Leu Lys Ala Val Glu Gln Gly Ala Pro Val Thr Leu Ile Glu Arg
        115                 120                 125

Gly Thr Ile Gly Gly Thr Cys Val Asn Val Gly Cys Val Pro Ser Lys
    130                 135                 140

Ile Met Ile Arg Ala Ala His Ile Ala His Leu Arg Arg Glu Ser Pro
145                 150                 155                 160

Phe Asp Gly Gly Ile Ala Ala Thr Thr Pro Thr Ile Gln Arg Thr Ala
                165                 170                 175

Leu Leu Ala Gln Gln Gln Ala Arg Val Asp Glu Leu Arg His Ala Lys
            180                 185                 190

Tyr Glu Gly Ile Leu Glu Gly Asn Pro Ala Ile Thr Val Leu His Gly
```

```
            195                 200                 205
Ser Ala Arg Phe Lys Asp Asn Arg Asn Leu Ile Val Gln Leu Asn Asp
    210                 215                 220

Gly Gly Glu Arg Val Val Ala Phe Asp Arg Cys Leu Ile Ala Thr Gly
225                 230                 235                 240

Ala Ser Pro Ala Val Pro Pro Ile Pro Gly Leu Lys Asp Thr Pro Tyr
                245                 250                 255

Trp Thr Ser Thr Glu Ala Leu Val Ser Glu Thr Ile Pro Lys Arg Leu
                260                 265                 270

Ala Val Ile Gly Ser Ser Val Leu Ala Leu Glu Leu Ala Gln Ala Phe
            275                 280                 285

Ala Arg Leu Gly Ala Lys Val Thr Ile Leu Ala Arg Ser Thr Leu Phe
    290                 295                 300

Phe Arg Glu Asp Pro Ala Ile Gly Glu Ala Val Thr Ala Ala Phe Arg
305                 310                 315                 320

Met Glu Gly Ile Glu Val Arg Glu His Thr Gln Ala Ser Gln Val Ala
                325                 330                 335

Tyr Ile Asn Gly Glu Gly Asp Gly Glu Phe Val Leu Thr Thr Ala His
                340                 345                 350

Gly Glu Leu Arg Ala Asp Lys Leu Leu Val Ala Thr Gly Arg Ala Pro
            355                 360                 365

Asn Thr Arg Lys Leu Ala Leu Asp Ala Thr Gly Val Thr Leu Thr Pro
    370                 375                 380

Gln Gly Ala Ile Val Ile Asp Pro Gly Met Arg Thr Ser Val Glu His
385                 390                 395                 400

Ile Tyr Ala Ala Gly Asp Cys Thr Asp Gln Pro Gln Phe Val Tyr Val
                405                 410                 415

Ala Ala Ala Ala Gly Thr Arg Ala Ala Ile Asn Met Thr Gly Gly Asp
                420                 425                 430

Ala Ala Leu Asn Leu Thr Ala Met Pro Ala Val Val Phe Thr Asp Pro
            435                 440                 445

Gln Val Ala Thr Val Gly Tyr Ser Glu Ala Glu Ala His His Asp Gly
    450                 455                 460

Ile Lys Thr Asp Ser Arg Thr Leu Thr Leu Asp Asn Val Pro Arg Ala
465                 470                 475                 480

Leu Ala Asn Phe Asp Thr Arg Gly Phe Ile Lys Leu Val Val Glu Glu
                485                 490                 495

Gly Ser Gly Arg Leu Ile Gly Val Gln Ala Val Ala Pro Glu Ala Gly
                500                 505                 510

Glu Leu Ile Gln Thr Ala Ala Leu Ala Ile Arg Asn Arg Met Thr Val
            515                 520                 525

Gln Glu Leu Ala Asp Gln Leu Phe Pro Tyr Leu Thr Met Val Glu Gly
    530                 535                 540

Leu Lys Leu Ala Ala Gln Thr Phe Asn Lys Asp Val Lys Gln Leu Ser
545                 550                 555                 560

Cys Cys Ala Gly (2) INFORMATION FOR SEQ ID NO:17:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
```

(A) DESCRIPTION: /desc = "Oligonucleotide"

(iii) HYPOTHETICAL: NO (iv) ANTI-SENSE: NO (xi) SEQUENCE DESCRIPTION: SEQ ID NO:17:

GCGGTCGGAT CCGAATTCGT CGACTAAGGA GGAGCCACAA TGAAGCTCGC CCCATAT        57

(2) INFORMATION FOR SEQ ID NO:18:

(i) SEQUENCE CHARACTERISTICS:
         (A) LENGTH: 43 base pairs
         (B) TYPE: nucleic acid
         (C) STRANDEDNESS: single
         (D) TOPOLOGY: linear (ii) MOLECULE TYPE: other nucleic acid
          (A) DESCRIPTION: /desc = "Oligonucleotide"

(iii) HYPOTHETICAL: NO (xi) SEQUENCE DESCRIPTION: SEQ ID NO:18:

CGTATCGGAT CCGAATTCAA GCTTATCACG GTGTCCTAGA TGA        43

(2) INFORMATION FOR SEQ ID NO:19:

(i) SEQUENCE CHARACTERISTICS:
         (A) LENGTH: 1752 base pairs
         (B) TYPE: nucleic acid
         (C) STRANDEDNESS: double
         (D) TOPOLOGY: Not Relevant (ii) MOLECULE TYPE: other nucleic acid
          (A) DESCRIPTION: /desc = "Mutagenized merApe47"

(iii) HYPOTHETICAL: NO (ix) FEATURE:
          (A) NAME/KEY: CDS
          (B) LOCATION: 40..1734

(ix) FEATURE:
          (A) NAME/KEY: mat_peptide
          (B) LOCATION: 40..1731

(xi) SEQUENCE DESCRIPTION: SEQ ID NO:19:

```
CTAGAACTAG TGGATCCCTA GATCTAAGAA GGAACCACA ATG AGC ACT CTC AAA        54
                                           Met Ser Thr Leu Lys
                                            1               5

ATC ACC GGC ATG ACT TGC GAC TCG TGC GCA GTG CAT GTC AAG GAC GCC      102
Ile Thr Gly Met Thr Cys Asp Ser Cys Ala Val His Val Lys Asp Ala
                 10                  15                  20

CTG GAG AAA GTG CCC GGC GTG CAA TCA GCG GAT GTC TCC TAC GCC AAG      150
Leu Glu Lys Val Pro Gly Val Gln Ser Ala Asp Val Ser Tyr Ala Lys
            25                  30                  35

GGC AGC GCC AAG CTC GCC ATT GAG GTC GGC ACG TCA CCC GAC GCG CTG      198
Gly Ser Ala Lys Leu Ala Ile Glu Val Gly Thr Ser Pro Asp Ala Leu
        40                  45                  50

ACG GCC GCT GTA GCT GGA CTC GGT TAT CGG GCC ACG CTG GCC GAT GCC      246
Thr Ala Ala Val Ala Gly Leu Gly Tyr Arg Ala Thr Leu Ala Asp Ala
    55                  60                  65

CCC TCA GTT TCG ACG CCG GGC GGA TTG CTC GAC AAG ATG CGC GAT CTG      294
Pro Ser Val Ser Thr Pro Gly Gly Leu Leu Asp Lys Met Arg Asp Leu
70                  75                  80                  85

CTG GGC AGA AAC GAC AAG ACG GGT AGC AGC GGC GCA TTG CAT ATC GCC      342
Leu Gly Arg Asn Asp Lys Thr Gly Ser Ser Gly Ala Leu His Ile Ala
                90                  95                 100
```

| | | |
|---|---|---|
| GTC ATC GGC AGC GGC GGG GCC GCG ATG GCA GCG GCG CTG AAG GCC GTC<br>Val Ile Gly Ser Gly Gly Ala Ala Met Ala Ala Ala Leu Lys Ala Val<br>                 105                        110                   115 | 390 |
| GAG CAA GGC GCA CCT GTC ACG CTG ATC GAG CGC GGC ACC ATC GGC GGC<br>Glu Gln Gly Ala Pro Val Thr Leu Ile Glu Arg Gly Thr Ile Gly Gly<br>          120                       125                  130 | 438 |
| ACC TGT GTT AAT GTT GGT TGT GTG CCG AGC AAG ATC ATG ATT CGT GCT<br>Thr Cys Val Asn Val Gly Cys Val Pro Ser Lys Ile Met Ile Arg Ala<br>135                       140                       145 | 486 |
| GCT CAC ATT GCT CAT CTT CGT CGT GAA TCT CCA TTT GAT GGT GGC ATT<br>Ala His Ile Ala His Leu Arg Arg Glu Ser Pro Phe Asp Gly Gly Ile<br>150                       155                   160                   165 | 534 |
| GCT GCA ACC ACT CCA ACC ATT CAA CGT ACT GCA CTC CTT GCA CAA CAA<br>Ala Ala Thr Thr Pro Thr Ile Gln Arg Thr Ala Leu Leu Ala Gln Gln<br>                 170                       175                  180 | 582 |
| CAA GCA CGT GTT GAT GAA CTT CGT CAT GCA AAG TAT GAA GGT ATT CTA<br>Gln Ala Arg Val Asp Glu Leu Arg His Ala Lys Tyr Glu Gly Ile Leu<br>             185                       190                   195 | 630 |
| GAA GGT AAC CCA GCC ATC ACT GTG CTT CAT GGC TCT GCA CGT TTC AAG<br>Glu Gly Asn Pro Ala Ile Thr Val Leu His Gly Ser Ala Arg Phe Lys<br>         200                       205                  210 | 678 |
| GAC AAC CGT AAC CTC ATT GTT CAA CTC AAC GAC GGC GGC GAG CGC GTG<br>Asp Asn Arg Asn Leu Ile Val Gln Leu Asn Asp Gly Gly Glu Arg Val<br>215                       220                       225 | 726 |
| GTG GCA TTC GAC CGC TGT CTC ATT GCC ACT GGT GCA AGC CCA GCT GTT<br>Val Ala Phe Asp Arg Cys Leu Ile Ala Thr Gly Ala Ser Pro Ala Val<br>230                       235                   240                   245 | 774 |
| CCA CCA ATT CCT GGT CTC AAG GAC ACT CCT TAC TGG ACT TCC ACT GAA<br>Pro Pro Ile Pro Gly Leu Lys Asp Thr Pro Tyr Trp Thr Ser Thr Glu<br>                 250                       255                  260 | 822 |
| GCA CTA GTG TCT GAG ACC ATT CCA AAG CGT CTT GCA GTC ATT GGC TCC<br>Ala Leu Val Ser Glu Thr Ile Pro Lys Arg Leu Ala Val Ile Gly Ser<br>             265                       270                   275 | 870 |
| TCT GTG GTG GCT CTT GAA CTT GCC CAG GCC TTT GCA CGT CTT GGT GCT<br>Ser Val Val Ala Leu Glu Leu Ala Gln Ala Phe Ala Arg Leu Gly Ala<br>         280                       285                  290 | 918 |
| AAA GTG ACC ATT CTT GCA CGC TCC ACT CTC TTC TTT CGT GAA GAC CCA<br>Lys Val Thr Ile Leu Ala Arg Ser Thr Leu Phe Phe Arg Glu Asp Pro<br>295                       300                       305 | 966 |
| GCT ATA GGT GAA GCT GTT ACT GCT GCA TTT CGC ATG GAA GGC ATT GAA<br>Ala Ile Gly Glu Ala Val Thr Ala Ala Phe Arg Met Glu Gly Ile Glu<br>310                       315                       320                   325 | 1014 |
| GTG CGT GAG CAT ACT CAA GCA AGC CAA GTT GCC TAT ATC AAT GGT GAA<br>Val Arg Glu His Thr Gln Ala Ser Gln Val Ala Tyr Ile Asn Gly Glu<br>                 330                       335                  340 | 1062 |
| GGT GAC GGT GAA TTC GTC CTA ACC ACT GCT CAT GGT GAA CTT CGT GCA<br>Gly Asp Gly Glu Phe Val Leu Thr Thr Ala His Gly Glu Leu Arg Ala<br>             345                       350                   355 | 1110 |
| GAC AAA CTC CTT GTT GCA ACT GGT CGT GCA CCA AAC ACT CGC AAA CTG<br>Asp Lys Leu Leu Val Ala Thr Gly Arg Ala Pro Asn Thr Arg Lys Leu<br>         360                       365                  370 | 1158 |
| GCA CTT GAT GCA ACT GGT GTG ACC CTT ACT CCA CAA GGT GCT ATT GTC<br>Ala Leu Asp Ala Thr Gly Val Thr Leu Thr Pro Gln Gly Ala Ile Val<br>375                       380                       385 | 1206 |
| ATC GAC CCC GGC ATG CGT ACA AGC GTG GAA CAC ATC TAC GCC GCA GGC<br>Ile Asp Pro Gly Met Arg Thr Ser Val Glu His Ile Tyr Ala Ala Gly<br>390                       395                       400                   405 | 1254 |
| GAC TGC ACC GAC CAG CCG CAG TTC GTC TAT GTG GCG GCA GCG GCC GGC<br>Asp Cys Thr Asp Gln Pro Gln Phe Val Tyr Val Ala Ala Ala Ala Gly<br>                 410                       415                  420 | 1302 |

```
ACT CGC GCC GCG ATC AAC ATG ACC GGC GGT GAC GCC GCC CTG AAC CTG      1350
Thr Arg Ala Ala Ile Asn Met Thr Gly Gly Asp Ala Ala Leu Asn Leu
            425                 430                 435

ACC GCG ATG CCG GCC GTG GTG TTC ACC GAC CCG CAA GTG GCG ACC GTA      1398
Thr Ala Met Pro Ala Val Val Phe Thr Asp Pro Gln Val Ala Thr Val
            440                 445                 450

GGC TAC AGC GAG GCG GAA GCG CAC CAT GAC GGC ATC AAA ACT GAT AGT      1446
Gly Tyr Ser Glu Ala Glu Ala His His Asp Gly Ile Lys Thr Asp Ser
        455                 460                 465

CGC ACG CTA ACG CTG GAC AAC GTG CCG CGC GCG CTC GCC AAC TTC GAC      1494
Arg Thr Leu Thr Leu Asp Asn Val Pro Arg Ala Leu Ala Asn Phe Asp
470                 475                 480                 485

ACG CGC GGC TTC ATC AAA CTG GTG GTT GAA GAA GGG AGC GGA CGA CTG      1542
Thr Arg Gly Phe Ile Lys Leu Val Val Glu Glu Gly Ser Gly Arg Leu
                490                 495                 500

ATC GGC GTC CAG GCA GTG GCC CCG GAA GCG GGC GAA CTG ATC CAG ACG      1590
Ile Gly Val Gln Ala Val Ala Pro Glu Ala Gly Glu Leu Ile Gln Thr
            505                 510                 515

GCC GCA CTG GCG ATT CGC AAC CGG ATG ACG GTG CAG GAA CTG GCC GAC      1638
Ala Ala Leu Ala Ile Arg Asn Arg Met Thr Val Gln Glu Leu Ala Asp
            520                 525                 530

CAG TTG TTC CCC TAC CTG ACG ATG GTC GAA GGG TTG AAG CTC GCG GCG      1686
Gln Leu Phe Pro Tyr Leu Thr Met Val Glu Gly Leu Lys Leu Ala Ala
        535                 540                 545

CAG ACC TTC AAC AAG GAT GTG AAG CAG CTT TCC TGC TGC GCC GGG TGA      1734
Gln Thr Phe Asn Lys Asp Val Lys Gln Leu Ser Cys Cys Ala Gly  *
550                 555                 560                 565

GGCTGCAGGA ATTCGATA                                                  1752

(2) INFORMATION FOR SEQ ID NO:20:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:20:

Met Ser Thr Leu Lys Ile Thr Gly Met Thr Cys Asp Ser Cys Ala Val
 1               5                  10                  15

His Val Lys Asp Ala Leu Glu Lys Val Pro Gly Val Gln Ser Ala Asp
                20                  25                  30

Val Ser Tyr Ala Lys Gly Ser Ala Lys Leu Ala Ile Glu Val Gly Thr
            35                  40                  45

Ser Pro Asp Ala Leu Thr Ala Val Ala Gly Leu Gly Tyr Arg Ala
    50                  55                  60

Thr Leu Ala Asp Ala Pro Ser Val Ser Thr Pro Gly Gly Leu Leu Asp
65                  70                  75                  80

Lys Met Arg Asp Leu Leu Gly Arg Asn Asp Lys Thr Gly Ser Ser Gly
                85                  90                  95

Ala Leu His Ile Ala Val Ile Gly Ser Gly Ala Ala Met Ala Ala
                100                 105                 110

Ala Leu Lys Ala Val Glu Gln Gly Ala Pro Val Thr Leu Ile Glu Arg
            115                 120                 125

Gly Thr Ile Gly Gly Thr Cys Val Asn Val Gly Cys Val Pro Ser Lys
        130                 135                 140

Ile Met Ile Arg Ala Ala His Ile Ala His Leu Arg Arg Glu Ser Pro
145                 150                 155                 160
```

```
Phe Asp Gly Gly Ile Ala Ala Thr Thr Pro Thr Ile Gln Arg Thr Ala
                165                 170                 175

Leu Leu Ala Gln Gln Ala Arg Val Asp Glu Leu Arg His Ala Lys
            180                 185                 190

Tyr Glu Gly Ile Leu Glu Gly Asn Pro Ala Ile Thr Val Leu His Gly
        195                 200                 205

Ser Ala Arg Phe Lys Asp Asn Arg Asn Leu Ile Val Gln Leu Asn Asp
210                 215                 220

Gly Gly Glu Arg Val Val Ala Phe Asp Arg Cys Leu Ile Ala Thr Gly
225                 230                 235                 240

Ala Ser Pro Ala Val Pro Ile Pro Gly Leu Lys Asp Thr Pro Tyr
                245                 250                 255

Trp Thr Ser Thr Glu Ala Leu Val Ser Glu Thr Ile Pro Lys Arg Leu
            260                 265                 270

Ala Val Ile Gly Ser Ser Val Val Ala Leu Glu Leu Ala Gln Ala Phe
        275                 280                 285

Ala Arg Leu Gly Ala Lys Val Thr Ile Leu Ala Arg Ser Thr Leu Phe
290                 295                 300

Phe Arg Glu Asp Pro Ala Ile Gly Glu Ala Val Thr Ala Ala Phe Arg
305                 310                 315                 320

Met Glu Gly Ile Glu Val Arg Glu His Thr Gln Ala Ser Gln Val Ala
                325                 330                 335

Tyr Ile Asn Gly Glu Gly Asp Gly Glu Phe Val Leu Thr Thr Ala His
            340                 345                 350

Gly Glu Leu Arg Ala Asp Lys Leu Leu Val Ala Thr Gly Arg Ala Pro
        355                 360                 365

Asn Thr Arg Lys Leu Ala Leu Asp Ala Thr Gly Val Thr Leu Thr Pro
370                 375                 380

Gln Gly Ala Ile Val Ile Asp Pro Gly Met Arg Thr Ser Val Glu His
385                 390                 395                 400

Ile Tyr Ala Ala Gly Asp Cys Thr Asp Gln Pro Gln Phe Val Tyr Val
                405                 410                 415

Ala Ala Ala Ala Gly Thr Arg Ala Ala Ile Asn Met Thr Gly Gly Asp
            420                 425                 430

Ala Ala Leu Asn Leu Thr Ala Met Pro Ala Val Val Phe Thr Asp Pro
        435                 440                 445

Gln Val Ala Thr Val Gly Tyr Ser Glu Ala Glu Ala His His Asp Gly
450                 455                 460

Ile Lys Thr Asp Ser Arg Thr Leu Thr Leu Asp Asn Val Pro Arg Ala
465                 470                 475                 480

Leu Ala Asn Phe Asp Thr Arg Gly Phe Ile Lys Leu Val Val Glu Glu
                485                 490                 495

Gly Ser Gly Arg Leu Ile Gly Val Gln Ala Val Ala Pro Glu Ala Gly
            500                 505                 510

Glu Leu Ile Gln Thr Ala Ala Leu Ala Ile Arg Asn Arg Met Thr Val
        515                 520                 525

Gln Glu Leu Ala Asp Gln Leu Phe Pro Tyr Leu Thr Met Val Glu Gly
530                 535                 540

Leu Lys Leu Ala Ala Gln Thr Phe Asn Lys Asp Val Lys Gln Leu Ser
545                 550                 555                 560

Cys Cys Ala Gly (2) INFORMATION FOR SEQ ID NO:21:
```

(i) SEQUENCE CHARACTERISTICS:
    (A) LENGTH: 73 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Oligonucleotide"

(iii) HYPOTHETICAL: NO (iv) ANTI-SENSE: NO (xi) SEQUENCE DESCRIPTION: SEQ ID NO:21:

AAGAAGGAAC CACAATGTCT ACTCTGAAGA TCACTGGTAT GACTTGTGAC TCTTGTGCAG      60

TGCATGTCAA GGA      73

(2) INFORMATION FOR SEQ ID NO:22:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO:22:

TCGAATTCCT GCAGCCTTAG CCAGCACAGC AGCTCAGCTG CTTCACATCC TT      52

(2) INFORMATION FOR SEQ ID NO:23:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO:23:

CATACACAAA TTGTGGTTGA TCAGTGCAAT CACCAGCTGC ATAGATGTGT TCCACAGAGG      60

TACGCATACC TGGATCAATC ACAATAGCAC CTTGTGGAG      99

(2) INFORMATION FOR SEQ ID NO:24:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (iv) ANTI-SENSE: NO (xi) SEQUENCE DESCRIPTION: SEQ ID NO:24:

ACCACAATTT GTGTATGTTG CTGCTGCTGC TGGTACCCGT GCTGCTATCA ACATGACTGG      60

TGGTGATGCT GCCCTCAACC TCACCGCGAT GCCGGCCGT      99

(2) INFORMATION FOR SEQ ID NO:25:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO:25:

```
CAAATGGAGA TTCACGACGA AGATGAGCAA TGTGAGCAGC ACGAATCATG ATCTTGCTTG     60

GCACACAACC AACATTAACA CAGGTGCCGC CGATGGTGC                           99
```

(2) INFORMATION FOR SEQ ID NO:26:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Olgionucleotide"

(iii) HYPOTHETICAL: NO (iv) ANTI-SENSE: NO (xi) SEQUENCE DESCRIPTION: SEQ ID NO:26:

```
TCGTGAATCT CCATTTGATG GTGGCATTGC TGCAACCACT CCAACCATTC AACGTACTGC     60

ACTCCTTGCA CAACAACAAG CACGTGTTGA TGAACTTCG                           99
```

(2) INFORMATION FOR SEQ ID NO:27:

(i) SEQUENCE CHARACTERISTICS:
        (A) LENGTH: 1752 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc = "Mutagenized merApe20"

(iii) HYPOTHETICAL: NO (iv) ANTI-SENSE: NO (ix) FEATURE:
        (A) NAME/KEY: CDS
        (B) LOCATION: 40..1734

(ix) FEATURE:
        (A) NAME/KEY: mat_peptide
        (B) LOCATION: 40..1731

(xi) SEQUENCE DESCRIPTION: SEQ ID NO:27:

```
CTAGAACTAG TGGATCCCTA GATCTAAGAA GGAACCACA ATG AGC ACT CTC AAA        54
                                          Met Ser Thr Leu Lys
                                           1               5

ATC ACC GGC ATG ACT TGC GAC TCG TGC GCA GTG CAT GTC AAG GAC GCC      102
Ile Thr Gly Met Thr Cys Asp Ser Cys Ala Val His Val Lys Asp Ala
         10                  15                  20

CTG GAG AAA GTG CCC GGC GTG CAA TCA GCG GAT GTC TCC TAC GCC AAG      150
Leu Glu Lys Val Pro Gly Val Gln Ser Ala Asp Val Ser Tyr Ala Lys
             25                  30                  35

GGC AGC GCC AAG CTC GCC ATT GAG GTC GGC ACG TCA CCC GAC GCG CTG      198
```

```
Gly Ser Ala Lys Leu Ala Ile Glu Val Gly Thr Ser Pro Asp Ala Leu
             40                  45                  50

ACG GCC GCT GTA GCT GGA CTC GGT TAT CGG GCC ACG CTG GCC GAT GCC     246
Thr Ala Ala Val Ala Gly Leu Gly Tyr Arg Ala Thr Leu Ala Asp Ala
 55                  60                  65

CCC TCA GTT TCG ACG CCG GGC GGA TTG CTC GAC AAG ATG CGC GAT CTG     294
Pro Ser Val Ser Thr Pro Gly Gly Leu Leu Asp Lys Met Arg Asp Leu
 70                  75                  80                  85

CTG GGC AGA AAC GAC AAG ACG GGT AGC AGC GGC GCA TTG CAT ATC GCC     342
Leu Gly Arg Asn Asp Lys Thr Gly Ser Ser Gly Ala Leu His Ile Ala
                 90                  95                 100

GTC ATC GGC AGC GGC GGG GCC GCG ATG GCA GCG GCG CTG AAG GCC GTC     390
Val Ile Gly Ser Gly Gly Ala Ala Met Ala Ala Ala Leu Lys Ala Val
                105                 110                 115

GAG CAA GGC GCA CCT GTC ACG CTG ATC GAG CGC GGC ACC ATC GGC GGC     438
Glu Gln Gly Ala Pro Val Thr Leu Ile Glu Arg Gly Thr Ile Gly Gly
         120                 125                 130

ACC TGC GTC AAT GTC GGT TGT GTG CCG TCC AAG ATC ATG ATC CGC GCC     486
Thr Cys Val Asn Val Gly Cys Val Pro Ser Lys Ile Met Ile Arg Ala
135                 140                 145

GCC CAT ATC GCC CAT CTG CGC CGG GAA AGC CCG TTC GAT GGC GGC ATC     534
Ala His Ile Ala His Leu Arg Arg Glu Ser Pro Phe Asp Gly Gly Ile
150                 155                 160                 165

GCC GCT ACC ACG CCG ACC ATC CAG CGC ACG GCG CTG CTG GCC CAG CAG     582
Ala Ala Thr Thr Pro Thr Ile Gln Arg Thr Ala Leu Leu Ala Gln Gln
                170                 175                 180

CAG GCC CGC GTC GAT GAA CTG CGC CAC GCC AAG TAC GAA GGC ATC TTG     630
Gln Ala Arg Val Asp Glu Leu Arg His Ala Lys Tyr Glu Gly Ile Leu
            185                 190                 195

GAG GGC AAT CCG GCG ATC ACT GTG CTG CAC GGC TCC GCC CGC TTT AAG     678
Glu Gly Asn Pro Ala Ile Thr Val Leu His Gly Ser Ala Arg Phe Lys
        200                 205                 210

GAC AAT CGC AAC CTG ATC GTG CAA CTC AAC GAC GGC GGC GAG CGC GTG     726
Asp Asn Arg Asn Leu Ile Val Gln Leu Asn Asp Gly Gly Glu Arg Val
215                 220                 225

GTG GCA TTC GAC CGC TGT CTC ATT GCC ACT GGT GCA AGC CCA GCT GTT     774
Val Ala Phe Asp Arg Cys Leu Ile Ala Thr Gly Ala Ser Pro Ala Val
230                 235                 240                 245

CCA CCA ATT CCT GGT CTC AAG GAC ACT CCT TAC TGG ACT TCC ACT GAA     822
Pro Pro Ile Pro Gly Leu Lys Asp Thr Pro Tyr Trp Thr Ser Thr Glu
                250                 255                 260

GCA CTA GTG TCT GAG ACC ATT CCA AAG CGT CTT GCA GTC ATT GGC TCC     870
Ala Leu Val Ser Glu Thr Ile Pro Lys Arg Leu Ala Val Ile Gly Ser
            265                 270                 275

TCT GTG GTG GCT CTT GAA CTT GCC CAG GCC TTT GCA CGT CTT GGT GCT     918
Ser Val Val Ala Leu Glu Leu Ala Gln Ala Phe Ala Arg Leu Gly Ala
        280                 285                 290

AAA GTG ACC ATT CTT GCA CGC TCC ACT CTC TTC TTT CGT GAA GAC CCA     966
Lys Val Thr Ile Leu Ala Arg Ser Thr Leu Phe Phe Arg Glu Asp Pro
295                 300                 305

GCT ATA GGT GAA GCT GTT ACT GCT GCA TTT CGC ATG GAA GGC ATT GAA    1014
Ala Ile Gly Glu Ala Val Thr Ala Ala Phe Arg Met Glu Gly Ile Glu
310                 315                 320                 325

GTG CGT GAG CAT ACT CAA GCA AGC CAA GTT GCC TAT ATC AAT GGT GAA    1062
Val Arg Glu His Thr Gln Ala Ser Gln Val Ala Tyr Ile Asn Gly Glu
                330                 335                 340

GGG GAC GGC GAA TTC GTG CTC ACC ACG GCG CAC GGC GAA CTG CGC GCC    1110
Gly Asp Gly Glu Phe Val Leu Thr Thr Ala His Gly Glu Leu Arg Ala
            345                 350                 355

GAC AAG CTG CTG GTC GCC ACC GGC CGC GCG CCC AAC ACA CGC AAG CTG    1158
```

```
                Asp Lys Leu Leu Val Ala Thr Gly Arg Ala Pro Asn Thr Arg Lys Leu
                        360                 365                 370

GCA CTG GAT GCG ACG GGC GTC ACG CTC ACC CCC CAA GGC GCT ATC GTC             1206
Ala Leu Asp Ala Thr Gly Val Thr Leu Thr Pro Gln Gly Ala Ile Val
    375                 380                 385

ATC GAC CCC GGC ATG CGT ACA AGC GTG GAA CAC ATC TAC GCC GCA GGC             1254
Ile Asp Pro Gly Met Arg Thr Ser Val Glu His Ile Tyr Ala Ala Gly
390                 395                 400                 405

GAC TGC ACC GAC CAG CCG CAG TTC GTC TAT GTG GCA GCG GCC GGC                 1302
Asp Cys Thr Asp Gln Pro Gln Phe Val Tyr Val Ala Ala Ala Gly
                410                 415                 420

ACT CGC GCC GCG ATC AAC ATG ACC GGC GGT GAC GCC GCC CTG AAC CTG             1350
Thr Arg Ala Ala Ile Asn Met Thr Gly Gly Asp Ala Ala Leu Asn Leu
                425                 430                 435

ACC GCG ATG CCG GCC GTG GTG TTC ACC GAC CCG CAA GTG GCG ACC GTA             1398
Thr Ala Met Pro Ala Val Val Phe Thr Asp Pro Gln Val Ala Thr Val
                440                 445                 450

GGC TAC AGC GAG GCG GAA GCG CAC CAT GAC GGC ATC AAA ACT GAT AGT             1446
Gly Tyr Ser Glu Ala Glu Ala His His Asp Gly Ile Lys Thr Asp Ser
        455                 460                 465

CGC ACG CTA ACG CTG GAC AAC GTG CCG CGC GCG CTC GCC AAC TTC GAC             1494
Arg Thr Leu Thr Leu Asp Asn Val Pro Arg Ala Leu Ala Asn Phe Asp
470                 475                 480                 485

ACG CGC GGC TTC ATC AAA CTG GTG GTT GAA GAA GGG AGC GGA CGA CTG             1542
Thr Arg Gly Phe Ile Lys Leu Val Val Glu Glu Gly Ser Gly Arg Leu
                490                 495                 500

ATC GGC GTC CAG GCA GTG GCC CCG GAA GCG GGC GAA CTG ATC CAG ACG             1590
Ile Gly Val Gln Ala Val Ala Pro Glu Ala Gly Glu Leu Ile Gln Thr
                505                 510                 515

GCC GCA CTG GCG ATT CGC AAC CGG ATG ACG GTG CAG GAA CTG GCC GAC             1638
Ala Ala Leu Ala Ile Arg Asn Arg Met Thr Val Gln Glu Leu Ala Asp
                520                 525                 530

CAG TTG TTC CCC TAC CTG ACG ATG GTC GAA GGG TTG AAG CTC GCG GCG             1686
Gln Leu Phe Pro Tyr Leu Thr Met Val Glu Gly Leu Lys Leu Ala Ala
        535                 540                 545

CAG ACC TTC AAC AAG GAT GTG AAG CAG CTT TCC TGC TGC GCC GGG TGA             1734
Gln Thr Phe Asn Lys Asp Val Lys Gln Leu Ser Cys Cys Ala Gly  *
550                 555                 560                 565

GGCTGCAGGA ATTCGATA                                                         1752

(2) INFORMATION FOR SEQ ID NO:28:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:28:

Met Ser Thr Leu Lys Ile Thr Gly Met Thr Cys Asp Ser Cys Ala Val
1               5                   10                  15

His Val Lys Asp Ala Leu Glu Lys Val Pro Gly Val Gln Ser Ala Asp
                20                  25                  30

Val Ser Tyr Ala Lys Gly Ser Ala Lys Leu Ala Ile Glu Val Gly Thr
        35                  40                  45

Ser Pro Asp Ala Leu Thr Ala Ala Val Ala Gly Leu Gly Tyr Arg Ala
    50                  55                  60

Thr Leu Ala Asp Ala Pro Ser Val Ser Thr Pro Gly Gly Leu Leu Asp
65                  70                  75                  80
```

```
Lys Met Arg Asp Leu Leu Gly Arg Asn Asp Lys Thr Gly Ser Ser Gly
                85                  90                  95

Ala Leu His Ile Ala Val Ile Gly Ser Gly Ala Ala Met Ala Ala
            100                 105                 110

Ala Leu Lys Ala Val Glu Gln Gly Ala Pro Val Thr Leu Ile Glu Arg
            115                 120                 125

Gly Thr Ile Gly Gly Thr Cys Val Asn Val Gly Cys Val Pro Ser Lys
            130                 135                 140

Ile Met Ile Arg Ala Ala His Ile Ala His Leu Arg Arg Glu Ser Pro
145                 150                 155                 160

Phe Asp Gly Gly Ile Ala Ala Thr Thr Pro Thr Ile Gln Arg Thr Ala
                165                 170                 175

Leu Leu Ala Gln Gln Ala Arg Val Asp Glu Leu Arg His Ala Lys
            180                 185                 190

Tyr Glu Gly Ile Leu Glu Gly Asn Pro Ala Ile Thr Val Leu His Gly
            195                 200                 205

Ser Ala Arg Phe Lys Asp Asn Arg Asn Leu Ile Val Gln Leu Asn Asp
210                 215                 220

Gly Gly Glu Arg Val Val Ala Phe Asp Arg Cys Leu Ile Ala Thr Gly
225                 230                 235                 240

Ala Ser Pro Ala Val Pro Pro Ile Pro Gly Leu Lys Asp Thr Pro Tyr
            245                 250                 255

Trp Thr Ser Thr Glu Ala Leu Val Ser Glu Thr Ile Pro Lys Arg Leu
            260                 265                 270

Ala Val Ile Gly Ser Ser Val Val Ala Leu Glu Leu Ala Gln Ala Phe
            275                 280                 285

Ala Arg Leu Gly Ala Lys Val Thr Ile Leu Ala Arg Ser Thr Leu Phe
            290                 295                 300

Phe Arg Glu Asp Pro Ala Ile Gly Glu Ala Val Thr Ala Ala Phe Arg
305                 310                 315                 320

Met Glu Gly Ile Glu Val Arg Glu His Thr Gln Ala Ser Gln Val Ala
                325                 330                 335

Tyr Ile Asn Gly Glu Gly Asp Gly Glu Phe Val Leu Thr Thr Ala His
            340                 345                 350

Gly Glu Leu Arg Ala Asp Lys Leu Leu Val Ala Thr Gly Arg Ala Pro
            355                 360                 365

Asn Thr Arg Lys Leu Ala Leu Asp Ala Thr Gly Val Thr Leu Thr Pro
370                 375                 380

Gln Gly Ala Ile Val Ile Asp Pro Gly Met Arg Thr Ser Val Glu His
385                 390                 395                 400

Ile Tyr Ala Ala Gly Asp Cys Thr Asp Gln Pro Gln Phe Val Tyr Val
                405                 410                 415

Ala Ala Ala Ala Gly Thr Arg Ala Ala Ile Asn Met Thr Gly Gly Asp
            420                 425                 430

Ala Ala Leu Asn Leu Thr Ala Met Pro Ala Val Val Phe Thr Asp Pro
            435                 440                 445

Gln Val Ala Thr Val Gly Tyr Ser Glu Ala Glu His His Asp Gly
            450                 455                 460

Ile Lys Thr Asp Ser Arg Thr Leu Thr Leu Asp Asn Val Pro Arg Ala
465                 470                 475                 480

Leu Ala Asn Phe Asp Thr Arg Gly Phe Ile Lys Leu Val Val Glu Glu
                485                 490                 495

Gly Ser Gly Arg Leu Ile Gly Val Gln Ala Val Ala Pro Glu Ala Gly
            500                 505                 510
```

```
Glu Leu Ile Gln Thr Ala Ala Leu Ala Ile Arg Asn Arg Met Thr Val
        515                 520                 525

Gln Glu Leu Ala Asp Gln Leu Phe Pro Tyr Leu Thr Met Val Glu Gly
        530                 535                 540

Leu Lys Leu Ala Ala Gln Thr Phe Asn Lys Asp Val Lys Gln Leu Ser
545                 550                 555                 560

Cys Cys Ala Gly (2) INFORMATION FOR SEQ ID NO:29:

(i) SEQUENCE CHARACTERISTICS:
        (A) LENGTH: 1746 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc = "Mutagenized merApe29"

(iii) HYPOTHETICAL: NO (ix) FEATURE:
        (A) NAME/KEY: CDS
        (B) LOCATION: 40..1728

(ix) FEATURE:
        (A) NAME/KEY: mat_peptide
        (B) LOCATION: 40..1725

(xi) SEQUENCE DESCRIPTION: SEQ ID NO:29:
```

| | |
|---|---|
| CTAGAACTAG TGGATCCCTA GATCTAAGAA GGAACCACA ATG AGC ACT CTC AAA<br>                                                           Met Ser Thr Leu Lys<br>                                                             1                 5 | 54 |
| ATC ACC GGC ATG ACT TGC GAC TCG TGC GCA GTG CAT GTC AAG GAC GCC<br>Ile Thr Gly Met Thr Cys Asp Ser Cys Ala Val His Val Lys Asp Ala<br>                10                    15                    20 | 102 |
| CTG GAG AAA GTG CCC GGC GTG CAA TCA GCG GAT GTC TCC TAC GCC AAG<br>Leu Glu Lys Val Pro Gly Val Gln Ser Ala Asp Val Ser Tyr Ala Lys<br>            25                  30                  35 | 150 |
| GGC AGC GCC AAG CTC GCC ATT GAG GTC GGC ACG TCA CCC GAC GCG CTG<br>Gly Ser Ala Lys Leu Ala Ile Glu Val Gly Thr Ser Pro Asp Ala Leu<br>        40                   45                  50 | 198 |
| ACG GCC GCT GTA GCT GGA CTC GGT TAT CGG GCC ACG CTG GCC GAT GCC<br>Thr Ala Ala Val Ala Gly Leu Gly Tyr Arg Ala Thr Leu Ala Asp Ala<br>  55                   60                  65 | 246 |
| CCC TCA GTT TCG ACG CCG GGC GGA TTG CTC GAC AAG ATG CGC GAT CTG<br>Pro Ser Val Ser Thr Pro Gly Gly Leu Leu Asp Lys Met Arg Asp Leu<br>70                75                  80                  85 | 294 |
| CTG GGC AGA AAC GAC AAG ACG GGT AGC AGC GGC GCA TTG CAT ATC GCC<br>Leu Gly Arg Asn Asp Lys Thr Gly Ser Ser Gly Ala Leu His Ile Ala<br>                90                    95                  100 | 342 |
| GTC ATC GGC AGC GGC GGG GCC GCG ATG GCA GCG GCG CTG AAG GCC GTC<br>Val Ile Gly Ser Gly Gly Ala Ala Met Ala Ala Ala Leu Lys Ala Val<br>            105                  110                115 | 390 |
| GAG CAA GGC GCA CCT GTC ACG CTG ATC GAG CGC GGC ACC ATC GGC GGC<br>Glu Gln Gly Ala Pro Val Thr Leu Ile Glu Arg Gly Thr Ile Gly Gly<br>        120                  125                130 | 438 |
| ACC TGC GTC AAT GTC GGT TGT GTG CCG TCC AAG ATC ATG ATC CGC GCC<br>Thr Cys Val Asn Val Gly Cys Val Pro Ser Lys Ile Met Ile Arg Ala<br>            135                  140                145 | 486 |
| GCC CAT ATC GCC CAT CTG CGC CGG GAA AGC CCG TTC GAT GGC GGC ATC<br>Ala His Ile Ala His Leu Arg Arg Glu Ser Pro Phe Asp Gly Gly Ile<br>150                  155                  160                165 | 534 |

-continued

| | | |
|---|---|---|
| GCC GCT ACC ACG CCG ACC ATC CAG CGC ACG GCG CTG CTG GCC CAG CAG<br>Ala Ala Thr Thr Pro Thr Ile Gln Arg Thr Ala Leu Leu Ala Gln Gln<br>           170                        175                        180 | 582 |
| CAG GCC CGC GTC GAT GAA CTG CGT CAT GCA AAG TAT GAA GGT ATT CTA<br>Gln Ala Arg Val Asp Glu Leu Arg His Ala Lys Tyr Glu Gly Ile Leu<br>                 185                       190                      195 | 630 |
| GAA GGT AAC CCA GCC ATC ACT GTG CTT CAT GGC TCT GCA CGT TTC AAG<br>Glu Gly Asn Pro Ala Ile Thr Val Leu His Gly Ser Ala Arg Phe Lys<br>        200                       205                      210 | 678 |
| GAC AAC CGT AAC CTC ATT GTT CAA CTC AAC GAC GGC GGC GAG CGC GTG<br>Asp Asn Arg Asn Leu Ile Val Gln Leu Asn Asp Gly Gly Glu Arg Val<br>215                         220                      225 | 726 |
| GTG GCA TTC GAC CGC TGT CTC ATT GCC ACT GGT GCA AGC CCA GCT GTT<br>Val Ala Phe Asp Arg Cys Leu Ile Ala Thr Gly Ala Ser Pro Ala Val<br>230                       235                      240                  245 | 774 |
| CCA CCA ATT CCT GGT CTC AAG GAC ACT CCT TAC TGG ACT TCC ACT GAA<br>Pro Pro Ile Pro Gly Leu Lys Asp Thr Pro Tyr Trp Thr Ser Thr Glu<br>                  250                      255                  260 | 822 |
| GTG TCT GAG ACC ATT CCA AAG CGT CTT GCA GTC ATT GGC TCC TCT GTG<br>Val Ser Glu Thr Ile Pro Lys Arg Leu Ala Val Ile Gly Ser Ser Val<br>             265                      270                      275 | 870 |
| GTG GCT CTT GAA CTT GCC CAG GCC TTT GCA CGT CTT GGT GCT AAA GTG<br>Val Ala Leu Glu Leu Ala Gln Ala Phe Ala Arg Leu Gly Ala Lys Val<br>        280                       285                      290 | 918 |
| ACC ATT CTT GCA CGC TCC ACT CTC TTC TTT CGT GAA GAC CCA GCT ATA<br>Thr Ile Leu Ala Arg Ser Thr Leu Phe Phe Arg Glu Asp Pro Ala Ile<br>295                       300                      305 | 966 |
| GGT GAA GCT GTT ACT GCT GCA TTT CGC ATG GAA GGC ATT GAA GTG CGT<br>Gly Glu Ala Val Thr Ala Ala Phe Arg Met Glu Gly Ile Glu Val Arg<br>310                       315                      320                  325 | 1014 |
| GAG CAT ACT CAA GCA AGC CAA GTT GCC TAT ATC AAT GGT GAA GGG GAC<br>Glu His Thr Gln Ala Ser Gln Val Ala Tyr Ile Asn Gly Glu Gly Asp<br>                     330                      335                  340 | 1062 |
| GGC GAA TTC GTG CTC ACC ACG GCG CAC GGC GAA CTG CGC GCC GAC AAG<br>Gly Glu Phe Val Leu Thr Thr Ala His Gly Glu Leu Arg Ala Asp Lys<br>             345                      350                      355 | 1110 |
| CTG CTG GTC GCC ACC GGC CGC GCG CCC AAC ACA CGC AAG CTG GCA CTG<br>Leu Leu Val Ala Thr Gly Arg Ala Pro Asn Thr Arg Lys Leu Ala Leu<br>        360                       365                      370 | 1158 |
| GAT GCG ACG GGC GTC ACG CTC ACC CCC CAA GGC GCT ATC GTC ATC GAC<br>Asp Ala Thr Gly Val Thr Leu Thr Pro Gln Gly Ala Ile Val Ile Asp<br>375                       380                      385 | 1206 |
| CCC GGC ATG CGT ACA AGC GTG GAA CAC ATC TAC GCC GCA GGC GAC TGC<br>Pro Gly Met Arg Thr Ser Val Glu His Ile Tyr Ala Ala Gly Asp Cys<br>390                       395                      400                  405 | 1254 |
| ACC GAC CAG CCG CAG TTC GTC TAT GTG GCG GCA GCG GCC GGC ACT CGC<br>Thr Asp Gln Pro Gln Phe Val Tyr Val Ala Ala Ala Gly Thr Arg<br>                     410                      415                  420 | 1302 |
| GCC GCG ATC AAC ATG ACC GGC GGT GAC GCC GCC CTG AAC CTG ACC GCG<br>Ala Ala Ile Asn Met Thr Gly Gly Asp Ala Ala Leu Asn Leu Thr Ala<br>                 425                      430                      435 | 1350 |
| ATG CCG GCC GTG GTG TTC ACC GAC CCG CAA GTG GCG ACC GTA GGC TAC<br>Met Pro Ala Val Val Phe Thr Asp Pro Gln Val Ala Thr Val Gly Tyr<br>        440                       445                      450 | 1398 |
| AGC GAG GCG GAA GCG CAC CAT GAC GGC ATC AAA ACT GAT AGT CGC ACG<br>Ser Glu Ala Glu Ala His His Asp Gly Ile Lys Thr Asp Ser Arg Thr<br>455                       460                      465 | 1446 |
| CTA ACG CTG GAC AAC GTG CCG CGC GCG CTC GCC AAC TTC GAC ACG CGC<br>Leu Thr Leu Asp Asn Val Pro Arg Ala Leu Ala Asn Phe Asp Thr Arg<br>470                       475                      480                  485 | 1494 |

```
GGC TTC ATC AAA CTG GTG GTT GAA GAA GGG AGC GGA CGA CTG ATC GGC      1542
Gly Phe Ile Lys Leu Val Val Glu Glu Gly Ser Gly Arg Leu Ile Gly
            490                 495                 500

GTC CAG GCA GTG GCC CCG GAA GCG GGC GAA CTG ATC CAG ACG GCC GCA      1590
Val Gln Ala Val Ala Pro Glu Ala Gly Glu Leu Ile Gln Thr Ala Ala
        505                 510                 515

CTG GCG ATT CGC AAC CGG ATG ACG GTG CAG GAA CTG GCC GAC CAG TTG      1638
Leu Ala Ile Arg Asn Arg Met Thr Val Gln Glu Leu Ala Asp Gln Leu
    520                 525                 530

TTC CCC TAC CTG ACG ATG GTC GAA GGG TTG AAG CTC GCG GCG CAG ACC      1686
Phe Pro Tyr Leu Thr Met Val Glu Gly Leu Lys Leu Ala Ala Gln Thr
535                 540                 545

TTC AAC AAG GAT GTG AAG CAG CTT TCC TGC TGC GCC GGG TGA              1728
Phe Asn Lys Asp Val Lys Gln Leu Ser Cys Cys Ala Gly *
550                 555                 560

GGCTGCAGGA ATTCGATA                                                  1746

(2) INFORMATION FOR SEQ ID NO:30:

(i) SEQUENCE CHARACTERISTICS:
        (A) LENGTH: 562 amino acids
        (B) TYPE: amino acid
        (D) TOPOLOGY: linear (ii) MOLECULE TYPE: protein (xi) SEQUENCE DESCRIPTION: SEQ ID NO:30:

Met Ser Thr Leu Lys Ile Thr Gly Met Thr Cys Asp Ser Cys Ala Val
 1               5                  10                  15

His Val Lys Asp Ala Leu Glu Lys Val Pro Gly Val Gln Ser Ala Asp
                20                  25                  30

Val Ser Tyr Ala Lys Gly Ser Ala Lys Leu Ala Ile Glu Val Gly Thr
            35                  40                  45

Ser Pro Asp Ala Leu Thr Ala Val Ala Gly Leu Gly Tyr Arg Ala
        50                  55                  60

Thr Leu Ala Asp Ala Pro Ser Val Ser Thr Pro Gly Gly Leu Leu Asp
65                  70                  75                  80

Lys Met Arg Asp Leu Leu Gly Arg Asn Asp Lys Thr Gly Ser Ser Gly
                85                  90                  95

Ala Leu His Ile Ala Val Ile Gly Ser Gly Gly Ala Ala Met Ala Ala
                100                 105                 110

Ala Leu Lys Ala Val Glu Gln Gly Ala Pro Val Thr Leu Ile Glu Arg
            115                 120                 125

Gly Thr Ile Gly Gly Thr Cys Val Asn Val Gly Cys Val Pro Ser Lys
130                 135                 140

Ile Met Ile Arg Ala Ala His Ile Ala His Leu Arg Arg Glu Ser Pro
145                 150                 155                 160

Phe Asp Gly Gly Ile Ala Ala Thr Thr Pro Thr Ile Gln Arg Thr Ala
                165                 170                 175

Leu Leu Ala Gln Gln Gln Ala Arg Val Asp Glu Leu Arg His Ala Lys
            180                 185                 190

Tyr Glu Gly Ile Leu Glu Gly Asn Pro Ala Ile Thr Val Leu His Gly
        195                 200                 205

Ser Ala Arg Phe Lys Asp Asn Arg Asn Leu Ile Val Gln Leu Asn Asp
    210                 215                 220

Gly Gly Glu Arg Val Val Ala Phe Asp Arg Cys Leu Ile Ala Thr Gly
225                 230                 235                 240

Ala Ser Pro Ala Val Pro Pro Ile Pro Gly Leu Lys Asp Thr Pro Tyr
```

```
                     245                 250                 255
Trp Thr Ser Thr Glu Val Ser Glu Thr Ile Pro Lys Arg Leu Ala Val
                260                 265                 270

Ile Gly Ser Ser Val Val Ala Leu Glu Leu Ala Gln Ala Phe Ala Arg
            275                 280                 285

Leu Gly Ala Lys Val Thr Ile Leu Ala Arg Ser Thr Leu Phe Phe Arg
        290                 295                 300

Glu Asp Pro Ala Ile Gly Glu Ala Val Thr Ala Ala Phe Arg Met Glu
305                 310                 315                 320

Gly Ile Glu Val Arg Glu His Thr Gln Ala Ser Gln Val Ala Tyr Ile
                325                 330                 335

Asn Gly Glu Gly Asp Gly Glu Phe Val Leu Thr Thr Ala His Gly Glu
            340                 345                 350

Leu Arg Ala Asp Lys Leu Leu Val Ala Thr Gly Arg Ala Pro Asn Thr
        355                 360                 365

Arg Lys Leu Ala Leu Asp Ala Thr Gly Val Thr Leu Thr Pro Gln Gly
    370                 375                 380

Ala Ile Val Ile Asp Pro Gly Met Arg Thr Ser Val Glu His Ile Tyr
385                 390                 395                 400

Ala Ala Gly Asp Cys Thr Asp Gln Pro Gln Phe Val Tyr Val Ala Ala
                405                 410                 415

Ala Ala Gly Thr Arg Ala Ala Ile Asn Met Thr Gly Gly Asp Ala Ala
            420                 425                 430

Leu Asn Leu Thr Ala Met Pro Ala Val Val Phe Thr Asp Pro Gln Val
        435                 440                 445

Ala Thr Val Gly Tyr Ser Glu Ala Glu Ala His His Asp Gly Ile Lys
    450                 455                 460

Thr Asp Ser Arg Thr Leu Thr Leu Asp Asn Val Pro Arg Ala Leu Ala
465                 470                 475                 480

Asn Phe Asp Thr Arg Gly Phe Ile Lys Leu Val Val Glu Glu Gly Ser
                485                 490                 495

Gly Arg Leu Ile Gly Val Gln Ala Val Ala Pro Glu Ala Gly Glu Leu
            500                 505                 510

Ile Gln Thr Ala Ala Leu Ala Ile Arg Asn Arg Met Thr Val Gln Glu
        515                 520                 525

Leu Ala Asp Gln Leu Phe Pro Tyr Leu Thr Met Val Glu Gly Leu Lys
    530                 535                 540

Leu Ala Ala Gln Thr Phe Asn Lys Asp Val Lys Gln Leu Ser Cys Cys
545                 550                 555                 560

Ala Gly (2) INFORMATION FOR SEQ ID NO:31:

(i) SEQUENCE CHARACTERISTICS:
        (A) LENGTH: 1695 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (vii) IMMEDIATE SOURCE:
        (B) CLONE: merApe100

(ix) FEATURE:
        (A) NAME/KEY: CDS
        (B) LOCATION: 1..1695
```

-continued (xi) SEQUENCE DESCRIPTION: SEQ ID NO:31:

| | | | | | | | | | | | | | | | | |
|---|---|---|---|---|---|---|---|---|---|---|---|---|---|---|---|---|
| ATG | TCT | ACT | CTG | AAG | ATC | ACT | GGT | ATG | ACT | TGT | GAC | TCT | TGT | GCA | GTG | 48 |
| Met | Ser | Thr | Leu | Lys | Ile | Thr | Gly | Met | Thr | Cys | Asp | Ser | Cys | Ala | Val | |
| 1 | | | | 5 | | | | | 10 | | | | | 15 | | |

| CAT | GTC | AAG | GAT | GCA | CTG | GAG | AAA | GTT | CCA | GGT | GTG | CAA | TCT | GCA | GAT | 96 |
|---|---|---|---|---|---|---|---|---|---|---|---|---|---|---|---|---|
| His | Val | Lys | Asp | Ala | Leu | Glu | Lys | Val | Pro | Gly | Val | Gln | Ser | Ala | Asp | |
| | | | 20 | | | | | 25 | | | | | 30 | | | |

| GTG | AGC | TAT | GCA | AAG | GGC | TCT | GCC | AAA | TTG | GCC | ATT | GAA | GTT | GGC | ACT | 144 |
|---|---|---|---|---|---|---|---|---|---|---|---|---|---|---|---|---|
| Val | Ser | Tyr | Ala | Lys | Gly | Ser | Ala | Lys | Leu | Ala | Ile | Glu | Val | Gly | Thr | |
| | | 35 | | | | | 40 | | | | | 45 | | | | |

| TCT | CCA | GAT | GCA | CTT | ACT | GCT | GCT | GTT | GCA | GGT | CTG | GGC | TAT | CGT | GCT | 192 |
|---|---|---|---|---|---|---|---|---|---|---|---|---|---|---|---|---|
| Ser | Pro | Asp | Ala | Leu | Thr | Ala | Ala | Val | Ala | Gly | Leu | Gly | Tyr | Arg | Ala | |
| | 50 | | | | | 55 | | | | | 60 | | | | | |

| ACT | CTT | GCA | GAT | GCA | CCA | TCT | GTG | TCT | ACT | CCA | GGT | GGT | CTG | CTT | GAT | 240 |
|---|---|---|---|---|---|---|---|---|---|---|---|---|---|---|---|---|
| Thr | Leu | Ala | Asp | Ala | Pro | Ser | Val | Ser | Thr | Pro | Gly | Gly | Leu | Leu | Asp | |
| 65 | | | | | 70 | | | | | 75 | | | | | 80 | |

| AAG | ATG | CGT | GAC | CTG | CTT | GGT | CGT | AAT | GAC | AAG | ACT | GGC | AGC | TCT | GGT | 288 |
|---|---|---|---|---|---|---|---|---|---|---|---|---|---|---|---|---|
| Lys | Met | Arg | Asp | Leu | Leu | Gly | Arg | Asn | Asp | Lys | Thr | Gly | Ser | Ser | Gly | |
| | | | | 85 | | | | | 90 | | | | | 95 | | |

| GCA | CTC | CAC | ATT | GCT | GTG | ATT | GGC | TCT | GGT | GGT | GCA | GCA | ATG | GCA | GCA | 336 |
|---|---|---|---|---|---|---|---|---|---|---|---|---|---|---|---|---|
| Ala | Leu | His | Ile | Ala | Val | Ile | Gly | Ser | Gly | Gly | Ala | Ala | Met | Ala | Ala | |
| | | | 100 | | | | | 105 | | | | | 110 | | | |

| GCA | CTT | AAA | GCT | GTT | GAA | CAA | GGT | GCT | CGT | GTG | ACT | CTG | ATT | GAA | CGT | 384 |
|---|---|---|---|---|---|---|---|---|---|---|---|---|---|---|---|---|
| Ala | Leu | Lys | Ala | Val | Glu | Gln | Gly | Ala | Arg | Val | Thr | Leu | Ile | Glu | Arg | |
| | | 115 | | | | | 120 | | | | | 125 | | | | |

| GGC | ACT | ATT | GGT | GGC | ACT | TGT | GTT | AAT | GTT | GGT | TGT | GTG | CCA | AGC | AAG | 432 |
|---|---|---|---|---|---|---|---|---|---|---|---|---|---|---|---|---|
| Gly | Thr | Ile | Gly | Gly | Thr | Cys | Val | Asn | Val | Gly | Cys | Val | Pro | Ser | Lys | |
| | 130 | | | | | 135 | | | | | 140 | | | | | |

| ATC | ATG | ATT | CGT | GCT | GCT | CAC | ATT | GCT | CAT | CTT | CGT | CGT | GAA | TCT | CCA | 480 |
|---|---|---|---|---|---|---|---|---|---|---|---|---|---|---|---|---|
| Ile | Met | Ile | Arg | Ala | Ala | His | Ile | Ala | His | Leu | Arg | Arg | Glu | Ser | Pro | |
| 145 | | | | | 150 | | | | | 155 | | | | | 160 | |

| TTT | GAT | GGT | GGC | ATT | GCT | GCA | ACC | ACT | CCA | ACC | ATT | CAA | CGT | ACT | GCA | 528 |
|---|---|---|---|---|---|---|---|---|---|---|---|---|---|---|---|---|
| Phe | Asp | Gly | Gly | Ile | Ala | Ala | Thr | Thr | Pro | Thr | Ile | Gln | Arg | Thr | Ala | |
| | | | | 165 | | | | | 170 | | | | | 175 | | |

| CTC | CTT | GCA | CAA | CAA | CAA | GCA | CGT | GTT | GAT | GAA | CTT | CGT | CAT | GCA | AAG | 576 |
|---|---|---|---|---|---|---|---|---|---|---|---|---|---|---|---|---|
| Leu | Leu | Ala | Gln | Gln | Gln | Ala | Arg | Val | Asp | Glu | Leu | Arg | His | Ala | Lys | |
| | | | 180 | | | | | 185 | | | | | 190 | | | |

| TAT | GAA | GGT | ATC | CTG | GAA | GGT | AAC | CCA | GCC | ATC | ACT | GTG | CTT | CAT | GGC | 624 |
|---|---|---|---|---|---|---|---|---|---|---|---|---|---|---|---|---|
| Tyr | Glu | Gly | Ile | Leu | Glu | Gly | Asn | Pro | Ala | Ile | Thr | Val | Leu | His | Gly | |
| | | 195 | | | | | 200 | | | | | 205 | | | | |

| TCT | GCA | CGT | TTC | AAG | GAC | AAC | CGT | AAC | CTC | ATT | GTT | CAA | CTT | AAT | GAT | 672 |
|---|---|---|---|---|---|---|---|---|---|---|---|---|---|---|---|---|
| Ser | Ala | Arg | Phe | Lys | Asp | Asn | Arg | Asn | Leu | Ile | Val | Gln | Leu | Asn | Asp | |
| | 210 | | | | | 215 | | | | | 220 | | | | | |

| GGT | GGT | GAA | CGT | GTG | GTG | GCT | TTT | GAC | CGC | TGT | CTC | ATT | GCC | ACT | GGT | 720 |
|---|---|---|---|---|---|---|---|---|---|---|---|---|---|---|---|---|
| Gly | Gly | Glu | Arg | Val | Val | Ala | Phe | Asp | Arg | Cys | Leu | Ile | Ala | Thr | Gly | |
| 225 | | | | | 230 | | | | | 235 | | | | | 240 | |

| GCA | AGC | CCA | GCT | GTT | CCA | CCA | ATT | CCT | GGT | CTC | AAG | GAC | ACT | CCT | TAC | 768 |
|---|---|---|---|---|---|---|---|---|---|---|---|---|---|---|---|---|
| Ala | Ser | Pro | Ala | Val | Pro | Pro | Ile | Pro | Gly | Leu | Lys | Asp | Thr | Pro | Tyr | |
| | | | | 245 | | | | | 250 | | | | | 255 | | |

| TGG | ACT | TCC | ACT | GAA | GCT | CTT | GTG | TCT | GAG | ACC | ATT | CCA | AAG | CGT | CTT | 816 |
|---|---|---|---|---|---|---|---|---|---|---|---|---|---|---|---|---|
| Trp | Thr | Ser | Thr | Glu | Ala | Leu | Val | Ser | Glu | Thr | Ile | Pro | Lys | Arg | Leu | |
| | | | 260 | | | | | 265 | | | | | 270 | | | |

| GCA | GTC | ATT | GGC | TCC | TCT | GTG | GTG | GCT | CTT | GAA | CTT | GCC | CAG | GCC | TTT | 864 |
|---|---|---|---|---|---|---|---|---|---|---|---|---|---|---|---|---|
| Ala | Val | Ile | Gly | Ser | Ser | Val | Val | Ala | Leu | Glu | Leu | Ala | Gln | Ala | Phe | |
| | | 275 | | | | | 280 | | | | | 285 | | | | |

| GCA | CGT | CTT | GGT | GCT | AAA | GTG | ACC | ATT | CTT | GCA | CGC | TCC | ACT | CTC | TTC | 912 |
|---|---|---|---|---|---|---|---|---|---|---|---|---|---|---|---|---|
| Ala | Arg | Leu | Gly | Ala | Lys | Val | Thr | Ile | Leu | Ala | Arg | Ser | Thr | Leu | Phe | |
| | 290 | | | | | 295 | | | | | 300 | | | | | |

| TTT | CGT | GAA | GAC | CCA | GCA | ATT | GGT | GAA | GCT | GTT | ACT | GCT | GCA | TTT | CGC | 960 |
|---|---|---|---|---|---|---|---|---|---|---|---|---|---|---|---|---|

```
Phe Arg Glu Asp Pro Ala Ile Gly Glu Ala Val Thr Ala Ala Phe Arg
305                 310                 315                 320

ATG GAA GGC ATT GAA GTG CGT GAG CAT ACT CAA GCA AGC CAA GTT GCC    1008
Met Glu Gly Ile Glu Val Arg Glu His Thr Gln Ala Ser Gln Val Ala
                325                 330                 335

TAT ATC AAT GGT GAA GGT GAT GGT GAC TTT GTC CTT ACC ACT GCT CAT    1056
Tyr Ile Asn Gly Glu Gly Asp Gly Asp Phe Val Leu Thr Thr Ala His
                340                 345                 350

GGT GAA CTT CGT GCA GAC AAA CTC CTT GTT GCA ACT GGT CGT GCA CCA    1104
Gly Glu Leu Arg Ala Asp Lys Leu Leu Val Ala Thr Gly Arg Ala Pro
                355                 360                 365

AAC ACT CGC AAA CTG GCA CTT GAT GCA ACT GGT GTG ACC CTT ACT CCA    1152
Asn Thr Arg Lys Leu Ala Leu Asp Ala Thr Gly Val Thr Leu Thr Pro
                370                 375                 380

CAA GGT GCT ATT GTG ATT GAT CCA GGT ATG CGT ACC TCT GTG GAA CAC    1200
Gln Gly Ala Ile Val Ile Asp Pro Gly Met Arg Thr Ser Val Glu His
385                 390                 395                 400

ATC TAT GCA GCT GGT GAT TGC ACT GAT CAA CCA CAA TTT GTG TAT GTT    1248
Ile Tyr Ala Ala Gly Asp Cys Thr Asp Gln Pro Gln Phe Val Tyr Val
                405                 410                 415

GCT GCT GCT GCT GGT ACT CGT GCT GCT ATC AAC ATG ACT GGT GGT GAT    1296
Ala Ala Ala Ala Gly Thr Arg Ala Ala Ile Asn Met Thr Gly Gly Asp
                420                 425                 430

GCT GCC CTC AAC CTC ACT GCT ATG CCA GCT GTT GTG TTC ACT GAC CCA    1344
Ala Ala Leu Asn Leu Thr Ala Met Pro Ala Val Val Phe Thr Asp Pro
                435                 440                 445

CAA GTG GCT ACT GTG GGT TAT TCT GAA GCT GAA GCT CAT CAT GAT GGC    1392
Gln Val Ala Thr Val Gly Tyr Ser Glu Ala Glu Ala His His Asp Gly
                450                 455                 460

ATC AAG ACT GAC TCT CGC ACT CTC ACT CTT GAC AAT GTG CCA CGT GCC    1440
Ile Lys Thr Asp Ser Arg Thr Leu Thr Leu Asp Asn Val Pro Arg Ala
465                 470                 475                 480

CTG GCC AAC TTT GAT ACT CGT GGC TTT ATC AAA CTT GTG GTG GAA GAA    1488
Leu Ala Asn Phe Asp Thr Arg Gly Phe Ile Lys Leu Val Val Glu Glu
                485                 490                 495

GGC TCT GGT CGT CTT ATT GGT GTG CAA GCA GTG GCA CCA GAA GCT GGT    1536
Gly Ser Gly Arg Leu Ile Gly Val Gln Ala Val Ala Pro Glu Ala Gly
                500                 505                 510

GAA CTC ATT CAA ACT GCT GCA CTT GCT ATT CGC AAC CGT ATG ACT GTG    1584
Glu Leu Ile Gln Thr Ala Ala Leu Ala Ile Arg Asn Arg Met Thr Val
                515                 520                 525

CAA GAA CTG GCT GAT CAG CTG TTT CCA TAC CTC ACT ATG GTG GAA GGT    1632
Gln Glu Leu Ala Asp Gln Leu Phe Pro Tyr Leu Thr Met Val Glu Gly
                530                 535                 540

CTC AAG CTC GCT GCT CAA ACC TTC AAC AAG GAT GTG AAG CAG CTG AGC    1680
Leu Lys Leu Ala Ala Gln Thr Phe Asn Lys Asp Val Lys Gln Leu Ser
545                 550                 555                 560

TGC TGT GCT GGC TAA                                                  1695
Cys Cys Ala Gly *
                565
```

(2) INFORMATION FOR SEQ ID NO:32:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:32:

Met Ser Thr Leu Lys Ile Thr Gly Met Thr Cys Asp Ser Cys Ala Val

```
  1               5                    10                      15
His Val Lys Asp Ala Leu Glu Lys Val Pro Gly Val Gln Ser Ala Asp
                20                  25                  30

Val Ser Tyr Ala Lys Gly Ser Ala Lys Leu Ala Ile Glu Val Gly Thr
            35                  40                  45

Ser Pro Asp Ala Leu Thr Ala Ala Val Ala Gly Leu Gly Tyr Arg Ala
        50                  55                  60

Thr Leu Ala Asp Ala Pro Ser Val Ser Thr Pro Gly Gly Leu Leu Asp
 65                 70                  75                  80

Lys Met Arg Asp Leu Leu Gly Arg Asn Asp Lys Thr Gly Ser Ser Gly
                85                  90                  95

Ala Leu His Ile Ala Val Ile Gly Ser Gly Ala Ala Met Ala Ala
                100                 105                 110

Ala Leu Lys Ala Val Glu Gln Gly Ala Arg Val Thr Leu Ile Glu Arg
            115                 120                 125

Gly Thr Ile Gly Gly Thr Cys Val Asn Val Gly Cys Val Pro Ser Lys
        130                 135                 140

Ile Met Ile Arg Ala Ala His Ile Ala His Leu Arg Arg Glu Ser Pro
145                 150                 155                 160

Phe Asp Gly Gly Ile Ala Ala Thr Thr Pro Thr Ile Gln Arg Thr Ala
                165                 170                 175

Leu Leu Ala Gln Gln Ala Arg Val Asp Glu Leu Arg His Ala Lys
            180                 185                 190

Tyr Glu Gly Ile Leu Glu Gly Asn Pro Ala Ile Thr Val Leu His Gly
                195                 200                 205

Ser Ala Arg Phe Lys Asp Asn Arg Asn Leu Ile Val Gln Leu Asn Asp
210                 215                 220

Gly Gly Glu Arg Val Val Ala Phe Asp Arg Cys Leu Ile Ala Thr Gly
225                 230                 235                 240

Ala Ser Pro Ala Val Pro Pro Ile Pro Gly Leu Lys Asp Thr Pro Tyr
                245                 250                 255

Trp Thr Ser Thr Glu Ala Leu Val Ser Glu Thr Ile Pro Lys Arg Leu
                260                 265                 270

Ala Val Ile Gly Ser Ser Val Val Ala Leu Glu Leu Ala Gln Ala Phe
            275                 280                 285

Ala Arg Leu Gly Ala Lys Val Thr Ile Leu Ala Arg Ser Thr Leu Phe
290                 295                 300

Phe Arg Glu Asp Pro Ala Ile Gly Glu Ala Val Thr Ala Ala Phe Arg
305                 310                 315                 320

Met Glu Gly Ile Glu Val Arg Glu His Thr Gln Ala Ser Gln Val Ala
                325                 330                 335

Tyr Ile Asn Gly Glu Gly Asp Gly Asp Phe Val Leu Thr Thr Ala His
                340                 345                 350

Gly Glu Leu Arg Ala Asp Lys Leu Leu Val Ala Thr Gly Arg Ala Pro
            355                 360                 365

Asn Thr Arg Lys Leu Ala Leu Asp Ala Thr Gly Val Thr Leu Thr Pro
        370                 375                 380

Gln Gly Ala Ile Val Ile Asp Pro Gly Met Arg Thr Ser Val Glu His
385                 390                 395                 400

Ile Tyr Ala Ala Gly Asp Cys Thr Asp Gln Pro Gln Phe Val Tyr Val
                405                 410                 415

Ala Ala Ala Ala Gly Thr Arg Ala Ala Ile Asn Met Thr Gly Gly Asp
                420                 425                 430
```

```
Ala Ala Leu Asn Leu Thr Ala Met Pro Ala Val Val Phe Thr Asp Pro
        435                 440                 445

Gln Val Ala Thr Val Gly Tyr Ser Glu Ala Glu Ala His His Asp Gly
    450                 455                 460

Ile Lys Thr Asp Ser Arg Thr Leu Thr Leu Asp Asn Val Pro Arg Ala
465                 470                 475                 480

Leu Ala Asn Phe Asp Thr Arg Gly Phe Ile Lys Leu Val Val Glu Glu
                485                 490                 495

Gly Ser Gly Arg Leu Ile Gly Val Gln Ala Val Ala Pro Glu Ala Gly
            500                 505                 510

Glu Leu Ile Gln Thr Ala Ala Leu Ala Ile Arg Asn Arg Met Thr Val
        515                 520                 525

Gln Glu Leu Ala Asp Gln Leu Phe Pro Tyr Leu Thr Met Val Glu Gly
    530                 535                 540

Leu Lys Leu Ala Ala Gln Thr Phe Asn Lys Asp Val Lys Gln Leu Ser
545                 550                 555                 560

Cys Cys Ala Gly
```

(2) INFORMATION FOR SEQ ID NO:33:

(i) SEQUENCE CHARACTERISTICS:
        (A) LENGTH: 703 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (vii) IMMEDIATE SOURCE:
        (B) CLONE: merBpe (ix) FEATURE:
        (A) NAME/KEY: CDS
        (B) LOCATION: 40..678

(xi) SEQUENCE DESCRIPTION: SEQ ID NO:33:

```
GCGGTCGGAT CCGAATTCGT CGACTAAGGA GGAGCCACA ATG AAG CTC GCC CCA         54
                                           Met Lys Leu Ala Pro
                                             1               5

TAT ATT TTA GAA CTT CTC ACT TCG GTC AAT CGT ACC AAT GGT ACT GCG       102
Tyr Ile Leu Glu Leu Leu Thr Ser Val Asn Arg Thr Asn Gly Thr Ala
             10                  15                  20

GAT CTC TTG GTC CCG CTA CTG CGG GAA CTC GCC AAG GGG CGT CCG GTT       150
Asp Leu Leu Val Pro Leu Leu Arg Glu Leu Ala Lys Gly Arg Pro Val
                 25                  30                  35

TCA CGA ACG ACA CTT GCC GGG ATT CTC GAC TGG CCC GCT GAG CGA GTG       198
Ser Arg Thr Thr Leu Ala Gly Ile Leu Asp Trp Pro Ala Glu Arg Val
             40                  45                  50

GCC GCC GTA CTC GAA CAG GCC ACC AGT ACC GAA TAT GAC AAA GAT GGG       246
Ala Ala Val Leu Glu Gln Ala Thr Ser Thr Glu Tyr Asp Lys Asp Gly
 55                  60                  65

AAC ATC ATC GGC TAC GGC CTC ACC TTG CGC GAG ACT TCG TAT GTC TTT       294
Asn Ile Ile Gly Tyr Gly Leu Thr Leu Arg Glu Thr Ser Tyr Val Phe
 70                  75                  80                  85

GAA ATT GAC GAC CGC CGT CTG TAT GCC TGG TGC GCG CTG GAC ACC TTG       342
Glu Ile Asp Asp Arg Arg Leu Tyr Ala Trp Cys Ala Leu Asp Thr Leu
                 90                  95                 100

ATA TTT CCG GCG CTG ATC GGC CGT ACA GCT CGC GTC TCA TCG CAT TGC       390
Ile Phe Pro Ala Leu Ile Gly Arg Thr Ala Arg Val Ser Ser His Cys
                105                 110                 115
```

```
GCT GCA ACC GGA GCA CCG GTT TCA CTC ACG GTT TCA CCC AGC GAG ATA      438
Ala Ala Thr Gly Ala Pro Val Ser Leu Thr Val Ser Pro Ser Glu Ile
            120                 125                 130

CAG GCT GTC GAA CCT GCC GGC ATG GCG GTG TCC TTG GTA TTG CCG CAG      486
Gln Ala Val Glu Pro Ala Gly Met Ala Val Ser Leu Val Leu Pro Gln
135                 140                 145

GAA GCA GCC GAC GTT CGT CAG TCC TTC TGT TGC CAT GTA CAT TTC TTT      534
Glu Ala Ala Asp Val Arg Gln Ser Phe Cys Cys His Val His Phe Phe
150                 155                 160                 165

GCA TCT GTC CCG ACG GCG GAA GAC TGG GCC TCC AAG CAT CAA GGA TTG      582
Ala Ser Val Pro Thr Ala Glu Asp Trp Ala Ser Lys His Gln Gly Leu
            170                 175                 180

GAA GGA TTG GCG ATC GTC AGT GTC CAC GAG GCT TTC GGC TTG GGC CAG      630
Glu Gly Leu Ala Ile Val Ser Val His Glu Ala Phe Gly Leu Gly Gln
                185                 190                 195

GAG TTT AAT CGA CAT CTG TTG CAG ACC ATG TCA TCT AGG ACA CCG TGA      678
Glu Phe Asn Arg His Leu Leu Gln Thr Met Ser Ser Arg Thr Pro  *
            200                 205                 210

TAAGCTTGAA TTCGGATCCG ATACG                                          703

(2) INFORMATION FOR SEQ ID NO:34:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO:34:

Met Lys Leu Ala Pro Tyr Ile Leu Glu Leu Leu Thr Ser Val Asn Arg
 1               5                  10                  15

Thr Asn Gly Thr Ala Asp Leu Leu Val Pro Leu Leu Arg Glu Leu Ala
            20                  25                  30

Lys Gly Arg Pro Val Ser Arg Thr Leu Ala Gly Ile Leu Asp Trp
        35                  40                  45

Pro Ala Glu Arg Val Ala Ala Val Leu Glu Gln Ala Thr Ser Thr Glu
    50                  55                  60

Tyr Asp Lys Asp Gly Asn Ile Ile Gly Tyr Gly Leu Thr Leu Arg Glu
65                  70                  75                  80

Thr Ser Tyr Val Phe Glu Ile Asp Asp Arg Arg Leu Tyr Ala Trp Cys
                85                  90                  95

Ala Leu Asp Thr Leu Ile Phe Pro Ala Leu Ile Gly Arg Thr Ala Arg
            100                 105                 110

Val Ser Ser His Cys Ala Ala Thr Gly Ala Pro Val Ser Leu Thr Val
        115                 120                 125

Ser Pro Ser Glu Ile Gln Ala Val Glu Pro Ala Gly Met Ala Val Ser
130                 135                 140

Leu Val Leu Pro Gln Glu Ala Ala Asp Val Arg Gln Ser Phe Cys Cys
145                 150                 155                 160

His Val His Phe Phe Ala Ser Val Pro Thr Ala Glu Asp Trp Ala Ser
                165                 170                 175

Lys His Gln Gly Leu Glu Gly Leu Ala Ile Val Ser Val His Glu Ala
            180                 185                 190

Phe Gly Leu Gly Gln Glu Phe Asn Arg His Leu Leu Gln Thr Met Ser
        195                 200                 205

Ser Arg Thr Pro
    210
```

We claim:

1. A nucleic acid molecule comprising a coding sequence for an organometal resistance protein, wherein said coding sequence is operably linked downstream of and under the regulatory control of a plant-expressible transcription and translation regulatory sequence.

2. The nucleic acid molecule of claim 1 wherein said organometal resistance protein is a MerB protein.

3. The nucleic acid molecule of claim 2 wherein said organometal protein is a MerB protein having an amino acid sequence as given in SEQ ID NO:34.

4. The nucleic acid molecule of claim 3 wherein said coding sequence is as given in SEQ ID NO:33, nucleotides 40–678.

5. A method of using a DNA molecule comprising a plant-expressible nucleotide sequence encoding an organomercury lyase protein operably linked to and expressed under the regulatory control of transcription regulatory sequences to produce a transgenic plant, plant cell or plant tissue with greater resistance to organomercurials than a parental plant, plant cell or plant tissue, said method comprising the steps of:

a) cloning a plant expressible sequence encoding an organomercury lyase operably linked to transcription regulatory sequences functional in a plant cell to produce an organomercurial resistance expression construct;

b) cloning the metal resistance expression construct of step (a) into a plasmid vector adapted for use in a plant cell to produce an organomercurial resistance expression vector; and c) introducing said organomercurial resistance expression vector of step (b) into a plant cell or plant tissue to produce transgenic plant tissue;

whereby said organomercurial lyase is expressed in said transgenic plant, plant cell or plant tissue, thereby increasing the resistance of said plant to organic mercury compounds.

6. The method of claim 5, further comprising after step (c) the step of:

d) regenerating said transgenic plant cell or tissue to produce a transgenic plant.

7. The method of claim 5 wherein said organomercurial resistance protein has an amino acid sequence as given in SEQ ID NO:34.

8. The method of claim 5 wherein said sequence encoding an organometal resistance protein has a nucleotide sequence as given in SEQ ID NO:33 from nucleotide 40 to nucleotide 678.

9. The method of claim 6, wherein said transgenic plant is a dicotyledonous plant.

10. The method of claim 9 wherein said transgenic plant is a member of the Solanaceae.

11. The method of claim 9 wherein said transgenic plant is Arabidopsis.

12. The method of claim 6 wherein said transgenic plant is a monocotyledonous plant.

13. The method of claim 6 wherein said transgenic plant is a gymnosperm.

14. The method of claim 13 wherein said transgenic plant is a member of the Coniferae.

15. The method of claim 5 wherein said transgenic plant, cell or tissue further contains and expresses a plant-expressible mercury ion reductase coding sequence.

16. The method of claim 15 wherein said plant-expressible mercury ion reductase coding sequence is merApe9, SEQ ID NO:15; merApe20, SEQ ID NO:27; merApe29, SEQ ID NO:29; merApe38, SEQ ID NO:13; merApe47, SEQ ID NO:19 or merApe100 SEQ ID NO:31.

17. A transgenic plant, a transgenic plant cell or transgenic plant tissue comprising a sequence encoding an organometal resistance protein, said coding sequence being operably linked to transcriptional regulatory sequences functional in a plant, wherein said plant, transgenic cell or tissue expresses said organometal resistance coding sequence.

18. The transgenic plant of claim 17 wherein said coding sequence is as given in SEQ ID NO:33, nucleotides 40–678.

19. The transgenic plant of claim 17 wherein said plant is a dicotyledonous plant.

20. The transgenic plant of claim 19 wherein said plant is a member of the Solanaceae.

21. The transgenic plant of claim 19 wherein said plant is yellow poplar.

22. The transgenic plant of claim 19 wherein said plant is a monocotyledonous plant.

23. The transgenic plant of claim 19 wherein said plant is a gymnosperm.

24. The transgenic plant of claim 23 wherein said plant is a member of the Coniferae.

25. The transgenic plant of claim 19 which also contains and expresses a plant-expressible mercuric ion reductase gene.

26. The transgenic plant of claim 25 wherein said plant-expressible mercury ion reductase coding sequence is merApe9, SEQ ID NO:15; merApe20, SEQ ID NO:27; merApe29, SEQ ID NO:29; merApe38, SEQ ID NO:13; merApe47, SEQ ID NO:19 or merApe100, SEQ ID NO:31.

27. A method of producing a transgenic plant, transgenic plant cell or transgenic plant tissue, having greater resistance to organometal compounds than a corresponding parental plant, and/or capable of detoxifying organometal compounds, said method comprising the steps of:

a) introducing the plant-expressible organomercurial lyase coding sequence into a plant cell or plant tissue to produce a transgenic plant cell or transgenic plant tissue;

b) regenerating a transgenic plant from the transgenic plant cell or transgenic plant tissue of step (a); and c) growing the transgenic plant, plant cell or plant tissue, under conditions which allow the expression of said construct, whereby the expression of said organometal resistance protein has the result that resistance is expressed and or that the transgenic plant detoxifies at least one organometal compound.

28. The method of claim 27 wherein said transgenic plant is resistant to and/or detoxifies organometal compounds including but not limited to alkyl mercury, alkenyl mercury, alkynyl mercury, aromatic mercury compounds, alkyl lead compounds, alkyl arsenic compounds and alkyl cadmium compounds.

29. The method of claim 28 wherein said transgenic plant also contains and expresses a plant-expressible mercuric ion reductase coding sequence.

30. The method of claim 29 wherein said plant-expressible mercury ion reductase coding sequence is merApe9, SEQ ID NO:15; merApe20, SEQ ID NO:27; merApe29, SEQ ID NO:29; merApe38, SEQ ID NO:13; merApe47, SEQ ID NO:19 or merApe100, SEQ ID NO:31.

* * * * *

UNITED STATES PATENT AND TRADEMARK OFFICE
CERTIFICATE OF CORRECTION

PATENT NO.    : 5,965,796

DATED         : October 12, 1999

INVENTOR(S)   : Meagher et al.

It is certified that error appears in the above-identified patent and that said Letters Patent is hereby corrected as shown below:

On the Title Page, under "Other Publications", under "Meagher, R.B. (1994)", please delete "Phyto-remediadtion" and replace with --Phyto-remediation--.
On "FIG. 1D", under the first bar, please delete "282-312N" and replace with --282-312A--.
In Column 5, line 1, please delete "Table 2" and replace with --FIG. 1B--.
In Column 5, line 19, please delete "Table 2" and replace with --FIG. 1B--.
In Column 5, line 32, please delete "□-transgenic" and replace with --▣-transgenic--.
In Column 5, line 48, please delete "FIG. 5" and replace with --FIG. 5A-5D--.
In Column 5, line 48, please delete "illustrates" and replace with --illustrate--.
In Column 6, line 1, please delete "FIG. 6" and replace with --FIG. 6A-6B--.
In Column 6, line 1, please delete "shows" and replace with --show--.
In Column 6, lines 5-6, please delete "materials and methods)" and replace with --Examples--.
In Column 6, line 17, please delete "Left" and replace with --Right--.
In Column 6, line 19, please delete "Right" and replace with --Left--.
In Column 10, line 49, please delete "NO:15" and replace with --NO:33--.
In Column 11, line 63, please delete "FIG. 6" and replace with --FIG. 6A-6B--.
In Column 17, please rewrite the first line from "CAAATCAC-3'" to --CAAAATCAC-3'--.
In Column 17, please rewrite the first section of SEQ ID NO:21 from "AAGAAGGAC" to --AAGAAGAAC--.
In Column 17, please rewrite the last section of SEQ ID NO:11 from "AGGCAACTTA" to --AGGCAACTTG--.
In Column 20, line 45, please insert --, SEQ ID:13-- after "FIG. 2".
In Column 20, line 56, please delete "MGSO$_4$," and replace with --MgSO$_4$,--.
In Column 24, line 6, please delete "MerB3'A" and replace with --MerB3'N--.
In Column 24, line 28, please insert --SD (Shine Delgarno)-- after "signal".
In Column 24, line 29, please delete "merA" and replace with --merB--.
In Column 24, line 30, please insert --and animal-- after "plant".
In Column 24, line 30, please insert --(PT/AT)-- after "translation".

UNITED STATES PATENT AND TRADEMARK OFFICE
CERTIFICATE OF CORRECTION

PATENT NO. : 5,965,796

DATED : October 12, 1999

INVENTOR(S) : Meagher et al.

It is certified that error appears in the above-identified patent and that said Letters Patent is hereby corrected as shown below:

In Column 26, line 9, please delete "Table 2" and replace with --Table 1--.
In Column 26, line 42, please delete "(20µ)" and replace with --(20 µl)--.
In Column 124, line 57, please delete "28" and replace with --27--.

Signed and Sealed this

Twelfth Day of September, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO. : 5,965,796

DATED : October 12, 1999

INVENTOR(S) : Meagher et al.

It is certified that error appears in the above-identified patent and that said Letters Patent is hereby corrected as shown below:

In Column 1, line 14, please insert --(Contract No. DE-FG07-96ER20257)-- between "funding" and "from".

Signed and Sealed this

Twenty-fourth Day of October, 2000

Attest:

Q. TODD DICKINSON

*Attesting Officer*    *Director of Patents and Trademarks*